United States Patent
Chaikind et al.

(10) Patent No.: US 11,884,924 B2
(45) Date of Patent: Jan. 30, 2024

(54) DUAL STRAND NUCLEIC ACID-GUIDED NICKASE EDITING

(71) Applicant: Inscripta, Inc., Boulder, CO (US)

(72) Inventors: Brian Chaikind, Boulder, CO (US); Aamir Mir, Boulder, CO (US)

(73) Assignee: Inscripta, Inc., Pleasanton, CA (US)

( * ) Notice: Subject to any disclaimer, the term of this patent is extended or adjusted under 35 U.S.C. 154(b) by 0 days.

(21) Appl. No.: 17/671,571

(22) Filed: Feb. 14, 2022

(65) Prior Publication Data
US 2022/0275377 A1 Sep. 1, 2022

Related U.S. Application Data

(60) Provisional application No. 63/231,229, filed on Aug. 9, 2021, provisional application No. 63/150,060, filed on Feb. 16, 2021.

(51) Int. Cl.
| | | |
|---|---|---|
| *C12N 15/62* | (2006.01) | |
| *C12N 5/071* | (2010.01) | |
| *C12N 9/22* | (2006.01) | |
| *C12N 15/11* | (2006.01) | |
| *C12N 15/90* | (2006.01) | |
| *C12N 15/86* | (2006.01) | |

(52) U.S. Cl.
CPC .......... *C12N 15/62* (2013.01); *C12N 5/0687* (2013.01); *C12N 9/22* (2013.01); *C12N 15/11* (2013.01); *C12N 15/86* (2013.01); *C12N 15/907* (2013.01); *C12Y 301/21004* (2013.01); *C12N 2310/20* (2017.05); *C12N 2740/15043* (2013.01); *C12N 2800/40* (2013.01); *C12N 2800/80* (2013.01)

(58) Field of Classification Search
CPC .................................................... C12N 15/62
See application file for complete search history.

(56) References Cited

U.S. PATENT DOCUMENTS

| | | |
|---|---|---|
| 6,365,373 B2 | 4/2002 | Presta et al. |
| 6,391,582 B2 | 5/2002 | Ying et al. |
| 6,837,995 B1 | 1/2005 | Vassarotti et al. |
| 7,166,443 B2 | 1/2007 | Walker et al. |
| 8,332,160 B1 | 12/2012 | Platt et al. |
| 8,697,359 B1 | 4/2014 | Zhang et al. |
| 8,926,977 B2 | 1/2015 | Miller et al. |
| 9,175,259 B2 | 11/2015 | Nankervis |
| 9,260,505 B2 | 2/2016 | Weir et al. |
| 9,361,427 B2 | 6/2016 | Hillson |
| 9,499,855 B2 | 11/2016 | Hyde et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,278 B2 | 5/2018 | Gill et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,179,898 B2 | 1/2019 | Khan |
| 10,227,576 B1 | 3/2019 | Cameron et al. |
| 10,240,117 B2 | 3/2019 | Dahlberg et al. |
| 10,240,167 B2 | 3/2019 | Gill et al. |
| 10,253,316 B2 | 4/2019 | Masquelier et al. |
| 10,256,316 B1 | 4/2019 | Frougier et al. |
| 10,266,849 B2 | 4/2019 | Gill et al. |
| 10,266,851 B2 | 4/2019 | Chen |
| 10,294,447 B2 | 5/2019 | Reif et al. |
| 10,323,242 B1 | 6/2019 | Masquelier et al. |
| 10,329,559 B1 | 6/2019 | Masquelier et al. |
| 10,337,028 B2 | 7/2019 | Gill et al. |
| 10,351,877 B2 | 7/2019 | Gill et al. |
| 10,364,442 B2 | 7/2019 | Gill et al. |
| 10,370,629 B2 | 8/2019 | Mietzner et al. |
| 10,376,889 B1 | 8/2019 | Masquelier et al. |
| 10,406,525 B1 | 9/2019 | Masquelier et al. |
| 10,421,959 B1 | 9/2019 | Masquelier et al. |
| 10,433,031 B1 | 9/2019 | Hudgens et al. |
| 10,435,662 B1 | 10/2019 | Masquelier et al. |
| 10,435,713 B2 | 10/2019 | Bernate et al. |
| 10,435,715 B2 | 10/2019 | Gill et al. |
| 10,465,185 B1 | 11/2019 | Masquelier et al. |
| 10,465,207 B2 | 11/2019 | Garst et al. |
| 10,478,822 B1 | 11/2019 | Masquelier et al. |
| 10,519,437 B1 | 12/2019 | Masquelier et al. |
| 10,532,324 B1 | 1/2020 | Masquelier et al. |
| 10,533,152 B1 | 1/2020 | Belgrader et al. |

(Continued)

FOREIGN PATENT DOCUMENTS

| | | |
|---|---|---|
| EP | 2395087 | 12/2011 |
| EP | 3199632 | 8/2017 |

(Continued)

OTHER PUBLICATIONS

International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.

(Continued)

*Primary Examiner* — Anoop K Singh
*Assistant Examiner* — David A Montanari
(74) *Attorney, Agent, or Firm* — Arnold & Porter Kaye Scholer LLP

(57) ABSTRACT

The present disclosure provides compositions of matter, methods and instruments for nucleic acid-guided nickase/reverse transcriptase fusion enzyme editing of nucleic acids in live mammalian cells.

17 Claims, 46 Drawing Sheets
Specification includes a Sequence Listing.

(56) References Cited

U.S. PATENT DOCUMENTS

| | | |
|---|---|---|
| 10,576,474 B2 | 3/2020 | Masquelier et al. |
| 10,577,576 B2 | 3/2020 | Nankervis |
| 10,584,333 B1 | 3/2020 | Masquelier et al. |
| 10,584,334 B1 | 3/2020 | Masquelier et al. |
| 10,590,375 B2 | 3/2020 | Masquelier et al. |
| 10,625,212 B2 | 4/2020 | Masquelier et al. |
| 10,633,625 B2 | 4/2020 | Nankervis et al. |
| 10,633,626 B2 | 4/2020 | Garst et al. |
| 10,633,627 B2 | 4/2020 | Garst et al. |
| 10,639,637 B1 | 5/2020 | Van Hatten et al. |
| 10,647,958 B2 | 5/2020 | Belgrader et al. |
| 10,647,982 B1 | 5/2020 | Masquelier et al. |
| 10,669,559 B2 | 6/2020 | Garst et al. |
| 10,689,645 B1 | 6/2020 | Belgrader et al. |
| 10,689,669 B1 | 6/2020 | Feldman et al. |
| 10,699,519 B2 | 6/2020 | Oyama et al. |
| 10,704,033 B1 | 7/2020 | Kim et al. |
| 10,711,284 B2 | 7/2020 | Garst et al. |
| 10,717,959 B2 | 7/2020 | Belgrader et al. |
| 10,723,995 B1 | 7/2020 | Belgrader et al. |
| 10,724,021 B1 | 7/2020 | Kim et al. |
| 10,731,180 B2 | 8/2020 | Garst et al. |
| 10,738,271 B2 | 8/2020 | Baker, Jr. et al. |
| 10,738,301 B1 | 8/2020 | Belgrader et al. |
| 10,738,663 B2 | 8/2020 | Jang et al. |
| 10,745,678 B1 | 8/2020 | Kim et al. |
| 10,767,169 B1 | 9/2020 | Kim et al. |
| 10,774,462 B2 | 9/2020 | Ayers et al. |
| 10,799,868 B1 | 10/2020 | Bernate et al. |
| 10,801,008 B1 | 10/2020 | Belgrader et al. |
| 10,835,869 B1 | 11/2020 | Belgrader et al. |
| 10,837,021 B1 | 11/2020 | Tian et al. |
| 10,851,339 B1 | 12/2020 | Belgrader et al. |
| 10,851,389 B2 | 12/2020 | Bernate et al. |
| 10,883,095 B1 * | 1/2021 | Mijts .................. C12N 15/113 |
| 10,894,958 B1 | 1/2021 | Ness et al. |
| 10,927,385 B2 | 2/2021 | Kannan et al. |
| 10,947,532 B2 | 3/2021 | Masquelier et al. |
| 10,954,485 B1 | 3/2021 | Belgrader et al. |
| 10,954,512 B1 | 3/2021 | Bernate et al. |
| 11,034,953 B1 | 6/2021 | Bernate et al. |
| 11,053,485 B2 | 7/2021 | Mijts et al. |
| 11,078,498 B2 | 8/2021 | Garst et al. |
| 11,204,032 B2 | 12/2021 | Meyer et al. |
| 2002/0139741 A1 | 10/2002 | Kopf |
| 2004/0110253 A1 | 6/2004 | Kappler et al. |
| 2006/0014137 A1 | 1/2006 | Ghosh et al. |
| 2007/0020761 A1 | 1/2007 | Yu et al. |
| 2010/0076057 A1 | 3/2010 | Sontheimer et al. |
| 2011/0294217 A1 | 12/2011 | McConnell-Smith et al. |
| 2013/0236970 A1 | 9/2013 | Anneren et al. |
| 2014/0068797 A1 | 3/2014 | Doudna et al. |
| 2014/0199767 A1 | 7/2014 | Barrangou et al. |
| 2014/0242033 A1 | 8/2014 | Gruber et al. |
| 2014/0273226 A1 | 9/2014 | Wu et al. |
| 2015/0024464 A1 | 1/2015 | Lippow et al. |
| 2015/0071898 A1 | 3/2015 | Liu et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0344549 A1 | 12/2015 | Muir et al. |
| 2016/0018427 A1 | 1/2016 | Streibl et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0130608 A1 | 5/2016 | Doudna et al. |
| 2016/0168592 A1 | 6/2016 | Church et al. |
| 2016/0264981 A1 | 9/2016 | Yang et al. |
| 2016/0281053 A1 | 9/2016 | Sorek et al. |
| 2016/0289673 A1 | 10/2016 | Huang et al. |
| 2016/0298134 A1 | 10/2016 | Chen et al. |
| 2016/0354487 A1 | 12/2016 | Zhang et al. |
| 2017/0002339 A1 | 1/2017 | Barrngou et al. |
| 2017/0022499 A1 | 1/2017 | Lu et al. |
| 2017/0044525 A1 | 2/2017 | Kaper et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0369870 A1 | 12/2017 | Gill et al. |
| 2018/0028567 A1 | 2/2018 | Li et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0187149 A1 | 7/2018 | Ma et al. |
| 2018/0200342 A1 | 7/2018 | Bikard et al. |
| 2018/0230460 A1 | 8/2018 | Gill et al. |
| 2018/0230461 A1 | 8/2018 | Gill et al. |
| 2018/0284125 A1 | 10/2018 | Gordon et al. |
| 2018/0327761 A1 | 11/2018 | Duchateau et al. |
| 2018/0371498 A1 | 12/2018 | Gill et al. |
| 2019/0017072 A1 | 1/2019 | Ditommaso et al. |
| 2019/0085324 A1 | 3/2019 | Regev et al. |
| 2019/0136230 A1 | 5/2019 | Sather et al. |
| 2019/0169605 A1 | 6/2019 | Masquelier et al. |
| 2019/0194650 A1 | 6/2019 | Gill et al. |
| 2019/0225928 A1 | 7/2019 | Masquelier et al. |
| 2019/0270987 A1 | 9/2019 | Masquelier et al. |
| 2020/0071660 A1 | 3/2020 | Spindler et al. |
| 2020/0095533 A1 | 3/2020 | Garst et al. |
| 2020/0109398 A1 | 4/2020 | Rubens et al. |
| 2020/0190461 A1 | 6/2020 | Bernate et al. |
| 2020/0216794 A1 | 7/2020 | Belgrader et al. |
| 2020/0263197 A1 | 8/2020 | Cheng et al. |
| 2020/0270632 A1 | 8/2020 | Roy et al. |
| 2021/0332388 A1 | 10/2021 | Belgrader et al. |
| 2021/0332389 A1 | 10/2021 | Belgrader et al. |

FOREIGN PATENT DOCUMENTS

| | | |
|---|---|---|
| WO | WO2002/010183 | 2/2002 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO2014/143381 | 9/2014 |
| WO | WO 2014/144495 | 9/2014 |
| WO | WO 2016/110453 | 7/2016 |
| WO | WO 2017/053902 | 3/2017 |
| WO | WO2017/075265 | 5/2017 |
| WO | WO 2017/078631 | 5/2017 |
| WO | WO 2017/083722 | 5/2017 |
| WO | WO 2017/106414 | 6/2017 |
| WO | WO2017/106414 | 6/2017 |
| WO | WO 2017/161371 | 9/2017 |
| WO | WO 2017/174329 | 10/2017 |
| WO | WO 2017/186718 | 11/2017 |
| WO | WO2017/212400 | 12/2017 |
| WO | WO 2017/216392 | 12/2017 |
| WO | WO 2017/223330 | 12/2017 |
| WO | WO 2018/015544 A1 | 1/2018 |
| WO | WO 2018/031950 | 2/2018 |
| WO | WO 2018/071672 | 4/2018 |
| WO | WO 2018/083339 | 5/2018 |
| WO | WO2018/152325 | 8/2018 |
| WO | WO2018/172556 | 9/2018 |
| WO | WO 2018/191715 | 10/2018 |
| WO | WO2019/006436 | 1/2019 |
| WO | WO 2019/046766 A1 | 3/2019 |
| WO | WO2019/055878 | 3/2019 |
| WO | WO2019/200004 | 10/2019 |
| WO | WO2019/209926 | 10/2019 |
| WO | WO2020/005383 | 1/2020 |
| WO | WO2020/021045 | 1/2020 |
| WO | WO2020/074906 | 4/2020 |
| WO | WO2020/191102 | 9/2020 |

(56) References Cited

FOREIGN PATENT DOCUMENTS

| | | | |
|---|---|---|---|
| WO | WO2020/191153 | 9/2020 | |
| WO | WO-2020191153 A2 * | 9/2020 | ............ C12N 15/102 |
| WO | WO2020/217057 | 10/2020 | |
| WO | WO 2021/138469 A1 | 7/2021 | |
| WO | WO2021/207541 | 10/2021 | |
| WO | WO 2021/226558 A1 | 11/2021 | |

OTHER PUBLICATIONS

Anzalone et al., "Search-and-replace genome editing without doubles-strand breaks or donor DNA," Nature, Oct. 21, 2019, vol. 576, No. 7785, pp. 149-157.

Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.

International Search Report and Written Opinion for International Application No. PCT/US20/65168, dated Mar. 17, 2021, p. 1-15.

International Search Report and Written Opinion for International Application No. PCT/US2020/038345, dated Nov. 23, 2020, p. 1-13.

International Search Report and Written Opinion for International Application No. PCT/US21/12867, dated May 12, 2021, p. 1-17.

International Search Report and Written Opinion for International Application No. PCT/US2020/064727, dated Apr. 28, 2021, p. 1-13.

International Search Report and Written Opinion for International Application No. PCT/US21/29008, dated Aug. 24, 2021, p. 1-19.

International Search Report and Written Opinion for International Application No. PCT/US21/29011, dated Aug. 24, 2021, p. 1-20.

Bauer, et al., "Cell-microcarrier Adhesion to Gas-Liquid Interfaces and Foam", Biotechnol. Prog. 2000, 16, 125-132, Oct. 19, 1999.

Datlinger, et al., "Pooled CRISPR screening with single-cell transcriptome readout", Nature Methods, Jan. 10, 2017; p. 1-10, doi:10.1038/nmeth.4177.

Dixit, et al., "Perturb-Seq: Dissecting Molecular Circuits with Scalable Single-Cell RNA Profiling of Pooled Genetic Screens", Cell 167, p. 1853-1866, Dec. 15, 2016.

GE Healthcare Life Sciences, "Microcarrier Cell Culture Principles and Methods", 18-1140-62 AC, p. 1-23, Nov. 2013.

Jacobi, et al., "Simplified CRISPR tools for efficient genome editing and streamlined protocols for their delivery into mammalian cells and mouse zygotes", Methods 121-122, p. 16-28, Mar. 23, 2017.

Jaitin, et al., "Dissecting Immune Circuits by Linking CRISPR-Pooled Screens with Single-Cell RNA-Seq", Cell 167, p. 1883-1896, Dec. 15, 2016.

Kim, et al., "Formation of Thermoresponsive Poly(N-isopropylacrylamide)/Dextran Particles by Atom Transfer Radical Polymerization", Macromol. Rapid Commun., 24, p. 517-521, 2003.

Kimple, et al., "Overview of Affinity Tags for Protein Purification", Curr Protoc Protein Sci.; 73: Unit-9-9. Doi:10.1002/0471140864. ps0909s73, p. 1-26, Aug. 6, 2015.

Nienow, et al., "A potentially scalable method for the harvesting of hMSCs from microcarriers", Biochemical Engineering Journal 85, p. 79-88, Feb. 4, 2014.

Replogle, et al., "Direct capture of CRISPR quides enables scalable, multiplexed, and multi-omic Perturb-Seq", bioRxiv; doi:http://dx.doi.org/10.1101/503367, p. 1-26, Dec. 21, 2018.

Sivalingam, et al., "Superior Red Blood Cell Generation from Human Pluripotent Stem Cells Through a Novel Microcarrier-Based Embryoid Body Platform", Tissue Engineering: Part C, vol. 22, No. 8, p. 765-780, Jun. 9, 2016.

International Search Report and Written Opinion for International Application No. PCT/US21/35807, dated Nov. 24, 2021, p. 1-21.

International Search Report and Written Opinion for International Application No. PCT/US21/50338, dated Dec. 10, 2021, p. 1-17.

International Search Report and Written Opinion for International Application No. PCT/US21/43097, dated Nov. 19, 2021, p. 1-12.

International Search Report and Written Opinion for International Application No. PCT/US21/39872, dated Oct. 27, 2021, p. 1-14.

International Search Report and Written Opinion for International Application No. PCT/US21/48566, dated Dec. 10, 2021, p. 1-10.

Filsinger, et al., "Characterizing the portability of RecT-mediated oligonucleotide recombination", bioRxiv, Apr. 15, 2020, doi:org/10.1101/2020.04.14.041095, p. 1-25.

Nelson, et al., "Engineered pegRNAs improve prime editing efficiency", Nature Biotechnology, Jul. 25, 2021, doi.org/10.1038/s41587-021-01039-7, p. 1-14.

Yu, et al., "Improved delivery of Cas9 protein/gRNA complexes using lipofectamine CRISPRMAX", Biotechnol Ltt, Feb. 18, 2016, doi 10.1007/s10529-016-2064-9, p. 919-929.

Bengali, et al., "Gene Delivery Through Cell Culture Substrate Adsorbed DNA Complexes", Biotechnol Bioeng., May 5, 2005, doi:10.1002/bit.20393, p. 1-23.

Segura, et al., "Substrate-mediated DNA delivery: role of the cationic polymer structure and extent of modification", Journal of Controlled Release, Aug. 9, 2003, doi:10.1016/j.jconrel.2003.08.003, p. 69-84.

Takahashi, et al., "Integration of CpG-free DNA induces de novo methylation of CpG islands in pluripotent stem cells," Science, May 5, 2017, vol. 356, No. 6337, pp. 1-7.

Chen, et al., "Human Pluripotent Stem Cell Culture: Considerations for Maintenance, Expansion, and Therapeutics", Cell Stem Cell, Jan. 2, 2014, doi.org/10.1016/j.stem.2013.12.005, p. 13-26.

Fayazpour, F., "Exploring New Applications for Photophysically Encoded Mircrocarriers", Ghent University Faculty of Pharmaceutical Sciences, Thesis Submission, Sep. 2008, 169 pages.

Chueng, et al., "Unlinking the methylome pattern from nucleotide sequence, revealed by large-scale in vivo genome engineering and methylome editing in medaka fish," PLoS Genetics, Dec. 21, 2017, vol. 13, No. 12, pp. 1-25.

Elvin, et al., "Modified bacteriophage lambda promoter vectors for overproduction of proteins in *Escherichia coli*", Gene, 87, Sep. 15, 1989, p. 123-126.

Segall-Shapiro, et al., "Engineered promoters enable constant gene expression at any copy number in bacteria", Nature Biotechnology, vol. 36, No. 4, Mar. 19, 2018, p. 352-363.

Xing, et al., "A CRISPR/Cas9 toolkit for multiplex genome editing in plants", BMC Plant Biology, 2014, p. 1-12.

Sun, et al., "A Single Multiplex crRNA Array for FnCpf1-Mediated Human Genome Editing," Molecular Therapy, Aug. 1, 2018, vol. 26, No. 8, pp. 2070-2076.

Kurata, et al., "Highly multiplexed genome engineering using CRISPR/Cas9 gRNA arrays," PLoS One, Sep. 17, 2018, vol. 13, No. 9, pp. 1-17.

Hubmann, et al., "Natural and Modified Promoters for Tailored Metabolic Engineering of the Yeast *Saccharomyces cerevisiae*", Methods in Molecular Biology, vol. 1152, doi10.1007/978-1-4939-0563-8_2, p. 17-42.

Unciti-Broceta, et al., "Combining Nebulization-Mediated Transfection and Polymer Microarrays for the Rapid Determination of Optimal Transfection Substrates", Journal of Combinatorial Chemistry, vol. 10, No. 2, Feb. 5, 2008, p. 179-184.

Fayazpour, et al., "Evaluation of Digitally Encoded Layer-by-layer Coated Microparticles as Cell Carriers", Advanced Functional Materials, Sep. 1, 2008, p. 2716-2723.

UniProtKB/TrEMBL, "A0A1G4WF58_9FIRM", Nov. 22, 2017, rerieved from Internet: https://www.uniprot.org/uniprot/A0A_1G4WF58.txt, pp. 1-3.

Natsume, et al., "Conditional Degrons for Controlling Protein Expression at the Protein Level", Annual Review of Genetics, vol. 51, 2017, doi.org/10.1146/annurev-genet-120116-024656, p. 83-104.

Chen, et al., "Enhancing the copy number of episomal plasmids in *Saccharomyces cerevisiae* for improved protein production", FEMS Yeast Research, Apr. 25, 2012, doi:10.1111/j.1567-1364.2012.00809.x; p. 598-607.

Price, et al., "Expanding and understanding the CRISPR toolbox for Bacillus subtilis with MAD7 and dMAD7", Biotechnology and Bioengineering, Feb. 19, 2020, doi:10.1002/bit.27312 p. 1805-1816.

International Search Report and Written Opinion for International Application No. PCT/US21/43534, dated Nov. 10, 2021, p. 1-16.

(56) References Cited

OTHER PUBLICATIONS

International Search Report and Written Opinion for International Application No. PCT/US20/26095, dated Jul. 17, 2020, p. 1-10.
Anzalone, et al., "Programmable large DNA deletion, replacement, integration, and inversion with twin prime editing and site-specific recombinases", bioRxiv, Nov. 2, 2021, doi:10.1101/2021.11.01. 466790, p. 1-51.
Horwitz, et al., "Efficient Multiplexed Integration of Synergistic Alleles and Metabolic Pathways in Yeasts via CRISPR-Cas", Cell Systems 1, Jul. 29, 2015, doi:10.1016/j.cels.2015.02.001, p. 88-96.
Jillette, et al., "Split Selectable Markers", Nature Communications, Oct. 31, 2019, doi:10.1038/s41467-019-12891-2, p. 1-8.
Pavankumar, "Inteins: Localized Distribution, Gene Regulation, and Protein Engineering for Biological Applications", Microorganisms, Feb. 28, 2018, doi:10.3390/microorganisms6010019, p. 1-15.
Choi, et al., "Precise genomic deletions using paired prime editing", bioRxiv, Jan. 2, 2021, doi:10.1101/2020.12.30.424891, p. 1-32.
Lin, et al., "High-efficiency prime editing with optimized, paired pegRNAs in plants", Nature Biotechnology, Mar. 25, 2021, doi:10. 1038/s41587-021-00868-w, p. 1-12.
Bolukbasi, et al., "Orthogonal Cas9-Cas9 chimeras provide a versatile platform for genome editing", Nature Communications, Nov. 19, 2018, doi:10.1038/s41467-018-07310-x, p. 1-12.
Kweon, et al., "Fusion guide RNAs for orthogonal gene manipulation with Cas9 and Cpf1", Nature Communications, Nov. 23, 2017, doi:10.1038/s41467-017-01650-w, p. 1-6.
International Search Report and Written Opinion for International Application No. PCT/US21/48578, dated Feb. 15, 2022, p. 1-12.
International Search Report and Written Opinion for International Application No. PCT/US21/61156, dated Mar. 3, 2022, p. 1-13.
Bao, et al., "Genome-scale engineering of *Saccharomyces cerevisiae* with single-nucleotide precision", Nature Biotechnology, doi:10. 1038/nbt.4132, pp. 1-6 (May 7, 2018).
Dicarlo, et al., "Genome engineering in *Saccharomyces cervisiae* using CRISPR-Case systems", Nucleic Acids Research, 41(7):4336-43 (2013).
Garst, et al., "Genome-wide mapping of mutations at single-nucleotide resolution for protein, metabolic and genome engineering", Nature Biotechnology, 35(1):48-59 (2017).
Hsu, et al., "DNA targeting specificity of RNA-guided Cas9 nucleases", Nature Biotechnology, 31(9):827-32 (2013).
Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Verwaal, et al., "CRISPR/Cpf1 enables fast and simple genome editing of *Saccharamyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt. 4137, pp. 1-16 (2018).
Dong, "Establishment of a highly efficient virus-inducible CRISPR/Cas9 system in insect cells," Antiviral Res., 130:50-7(2016).
Epinat et al., "A novel engineered meganuclease induces homologous recombination in eukaryotic cells, e.g., yeast and mammalian cells", Nucleic Acids Research, 31(11): 2952-2962.
Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).

Boles, et al., "Digital-to-biological converter for on-demand production of biologics", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Durai et al., "Zinc finger nucleases: custom-designed molecular scissors for genome engineering of plant and mammalian cells", Nucleic Acids Res., 33(18):5978-90 (2005).
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1): 81-9 (2009).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.

(56) References Cited

OTHER PUBLICATIONS

International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US19/47135, dated Jun. 11, 2020, p. 1-15.
U.S. Appl. No. 16/740,421, filed Jan. 11, 2020.
Landy, "Mechanistic and structural complexity in the site-specific recombination pathways of Int and FLP," *Current Opinion in Genetics and Development*, vol. 3, pp. 699-707 (1993) (Cambridge, MA).
Sauer, "Site-specific recombination: developments and applications," *Current Opinion in Biotechnology*, vol. 5; pp. 521-527 (1994) (Cambridge, MA).

\* cited by examiner

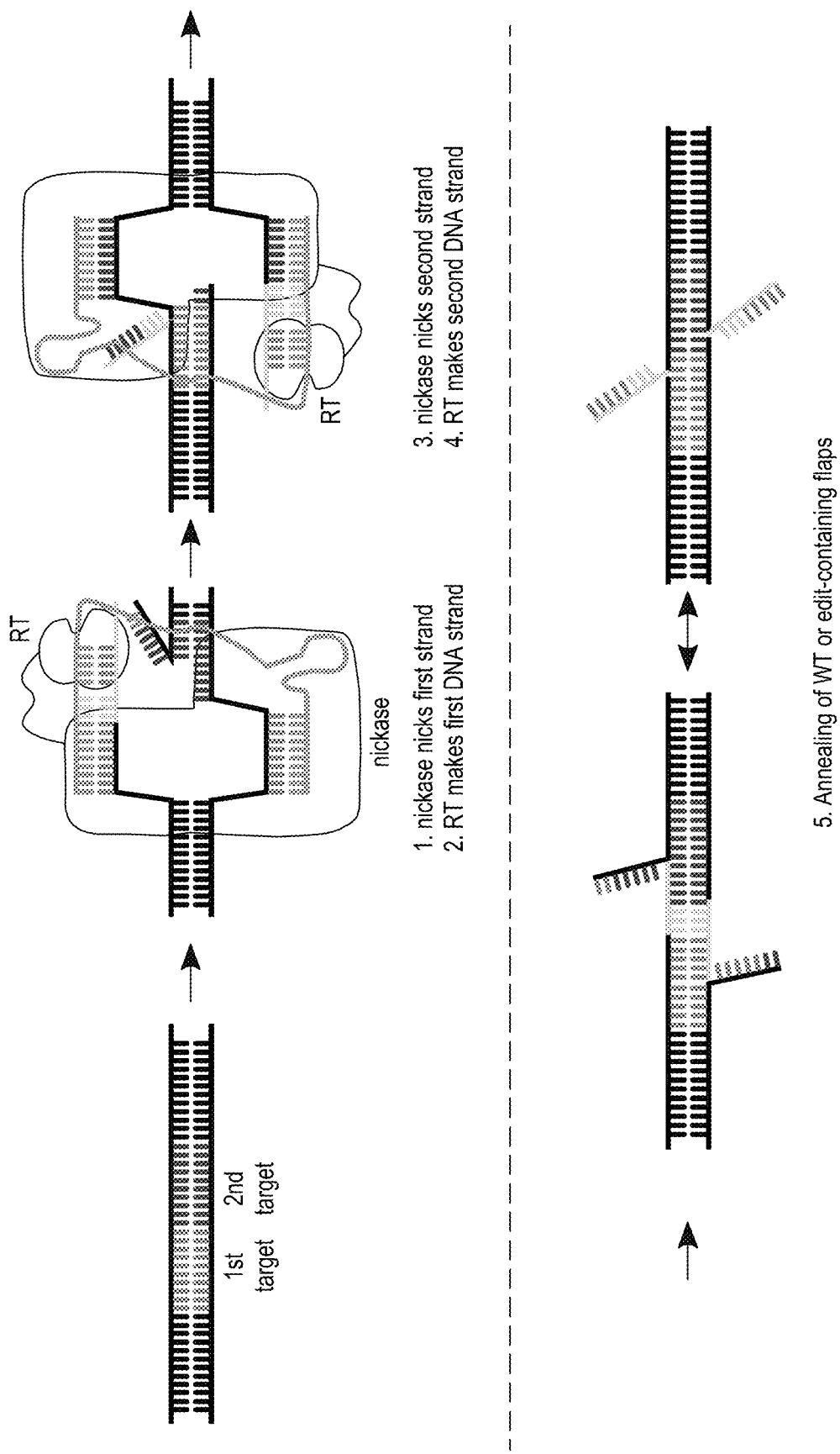

| Name | Spacer | Scaffold | Post Edit Homology | Edit | Mid-to-Edit | Primer Binding Region |
|---|---|---|---|---|---|---|
| C5-25 (SEQ ID No 4) | GGTGCTG CTTCATGT GGTCG (SEQ ID No 5) | GTTTTAGAGCTAG AATAGCAAGTTAA AATAAGGCTAGTC CGTTATCAACTTGA AAAGTGGGACCG AGTCGGTCC (SEQ ID No 6) | CCTGGCCCA CTTTGGTGA CCACCCT (SEQ ID No 7) | cagcc | ACGGCGTGCAGTGCTT CAGCCGCTACCCGA CGCTATCCGGA (SEQ ID No 8) | CCACATGAAGCAG (SEQ ID No 9) |
| 13-8 (SEQ ID No 10) | GGCGAGG GCGATGC CACCTA (SEQ ID No 11) | GTTTAGAGCTAG AATAGCAAGTTAA AATAAGGCTAGTC CGTTATCAACTTGA AAAGTGGGACCG AGTCGGTCC (SEQ ID No 12) | CACGCCGT | ggctg | AGGGTGGTCACCAAAG TGGGCCAGGGCACGG GCAGTTTGCCGGTGGT GCAGATGAACTTCAGG GTCAGCTTGCCGTAt (SEQ ID No 13) | GTGGCATCGCCCT (SEQ ID No 14) |
| 19-8 (SEQ ID No 15) | GACGTAG CCTTCGG GCATGG (SEQ ID No 16) | GTTTTAGAGCTAG AATAGCAAGTTAA AATAAGGCTAGTC CGTTATCAACTTGA AAAGTGGGACCG AGTCGGTCC (SEQ ID No 17) | ACCACCCT | cagcc | ACGGCGTGCAGTGCTT CAGCCGCTACCCCGAC CACATGAAGCAGACG ACTTCTTCAAGTCTGCCA (SEQ ID No 18) | TGCCCGAAGGCTA (SEQ ID No 19) |

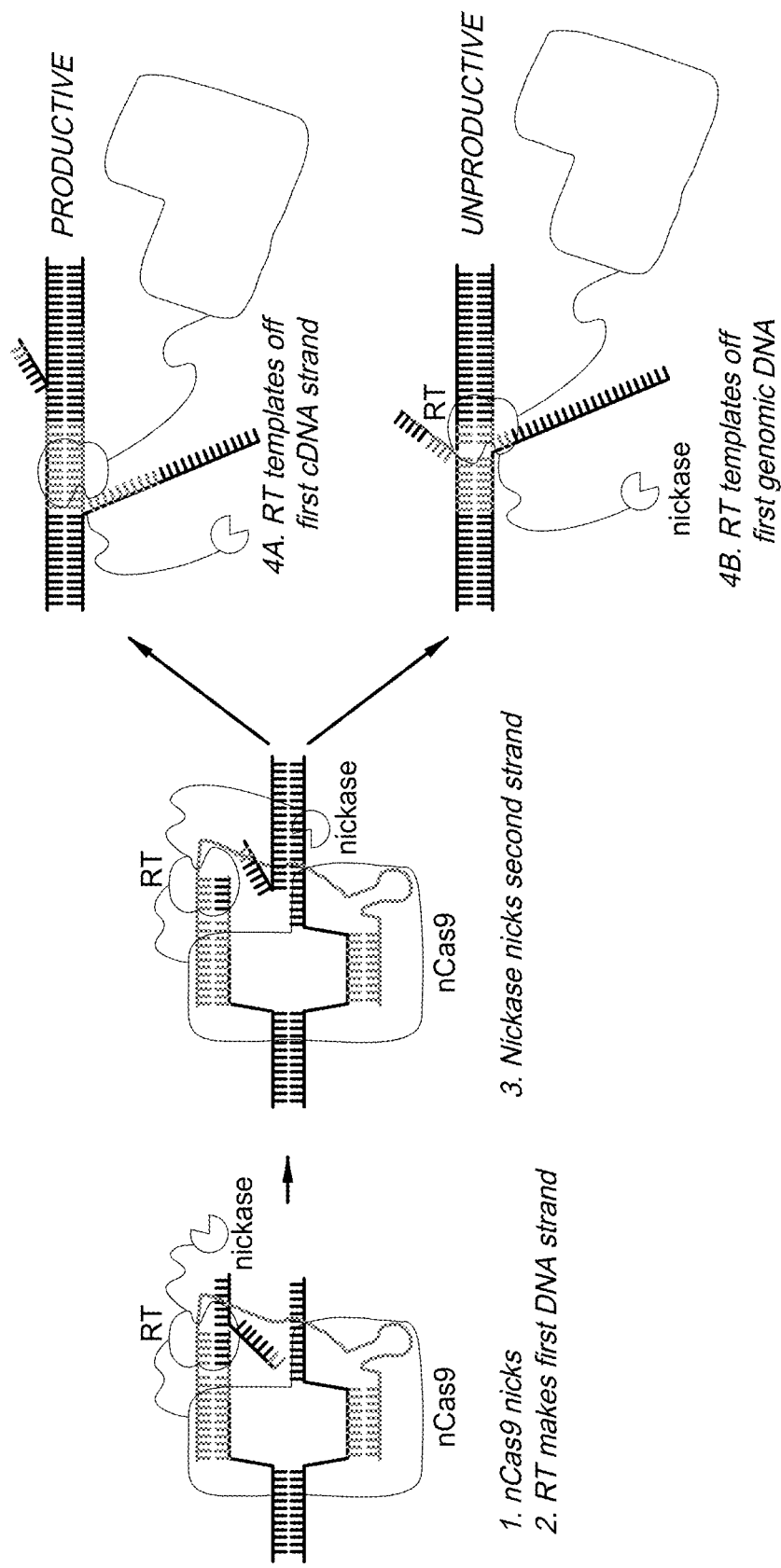

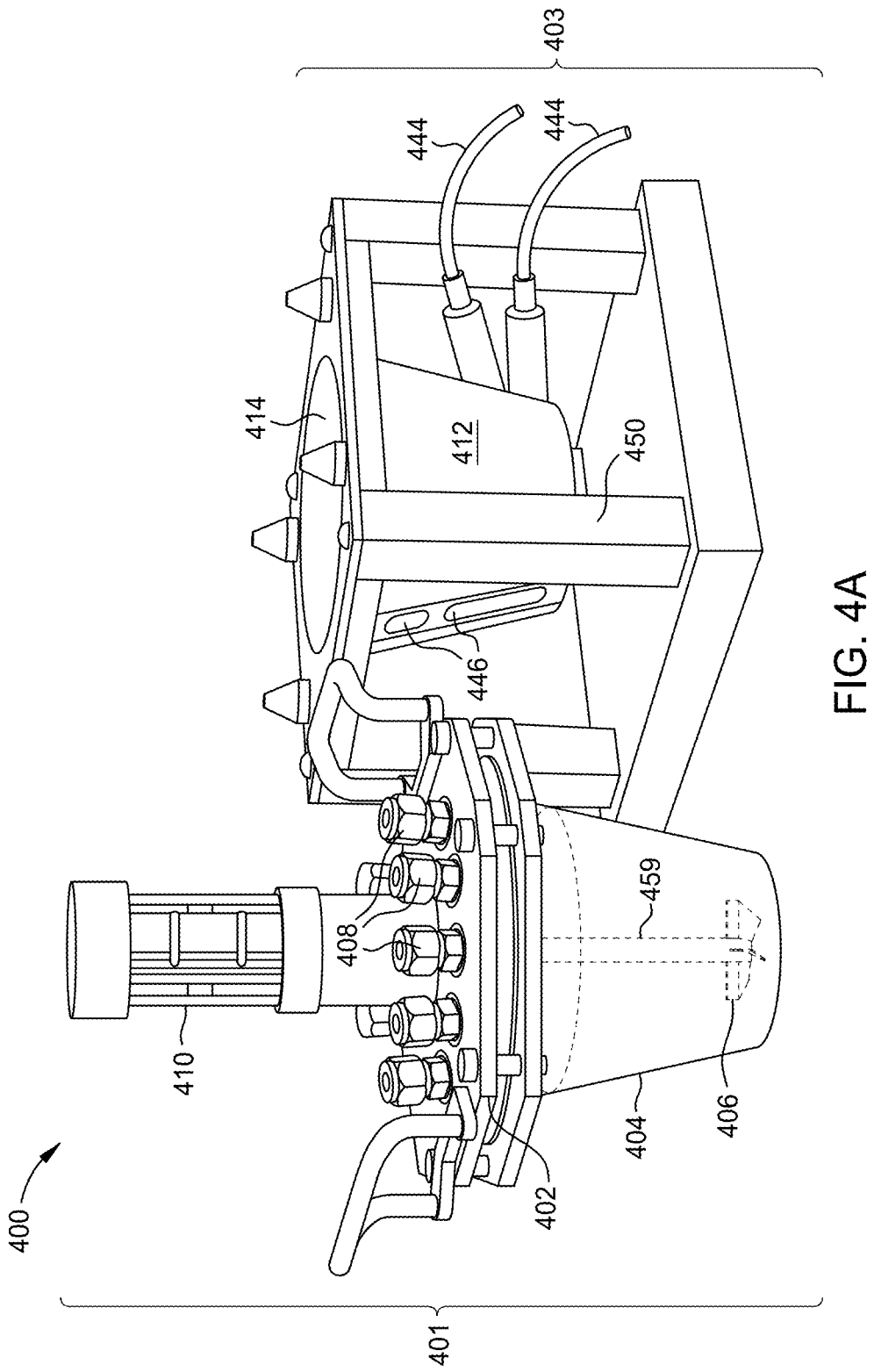

DUAL STRAND NUCLEIC ACID-GUIDED NICKASE EDITING

RELATED CASES

This application claims priority to U.S. Ser. No. 63/231,229, filed Aug. 9, 2021, entitled "Dual Strand Nucleic Acid-Guided Nickase Editing," and U.S. Ser. No. 63/150,060, filed Feb. 16, 2021, entitled "Dual Strand Nucleic Acid-Guided Nickase Editing," which are incorporated herein in their entirety.

INCORPORATION OF SEQUENCE LISTING

A sequence listing contained in the file named "17671571_ST25 Sequence Listing," which is 4,369 bytes (measured in MS-Windows®) and created Apr. 18, 2022, is filed electronically herewith and incorporated by reference in its entirety.

FIELD OF THE INVENTION

This invention relates to compositions of matter, methods and instruments for dual strand nucleic acid-guided nickase editing of live cells, particularly mammalian cells.

BACKGROUND OF THE INVENTION

In the following discussion, certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently various nucleases have been identified that allow manipulation of gene sequence, and hence gene function. The nucleases include nucleic acid-guided nucleases, which enable researchers to generate permanent edits in live cells. Of course, it is desirable to attain the highest editing rates possible in a cell population; however, in many instances the percentage of edited cells resulting from nucleic acid-guided nuclease editing can be in the single digits.

There is thus a need in the art of nucleic acid-guided nuclease editing for improved methods, compositions, modules and instruments for increasing the efficiency of editing, particularly in mammalian cells. The present disclosure addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure relates to methods and compositions for improved nucleic acid-guided nickase editing utilizing gRNAs and/or CFgRNAs to facilitate editing of opposite strands of a target locus. With the present compositions and methods, editing efficiency is improved using fusion proteins—i.e., a nickase/reverse transcriptase ("nickase-RT fusion")—that retains certain characteristics of nucleic acid-directed nucleases (e.g., the binding specificity and ability to cleave one or more DNA strands in a targeted manner) combined with another enzymatic activity, namely, reverse transcriptase activity. In some embodiments, the nickase-RT fusion includes two nickases or nucleases fused to a single reverse transcriptase. In some embodiments, the nickase-RT fusion may be introduced into the cells using a DNA molecule coding for the nickase-RT fusion separately or covalently-linked to one or more CF editing cassettes (i.e., editing cassettes comprising one or more CFgRNAs (defined infra), wherein the CFgRNAs are covalently linked to a repair template sequence) or the nickase-RT fusion may be introduced separately in protein form or as part of a complex. In addition to the nickase-RT fusion, the CF editing cassettes designed to edit opposite DNA strands in a target locus are utilized. The reverse transcriptase portion of the nickase-RT fusion uses the repair template(s) of each CF editing cassette to synthesize and edit at nicks created by the nickase(s) on opposite DNA strands of the target locus, thereby creating two complementary edit-containing flaps that circumvent the need for endogenous mismatch repair systems to resolve the edit.

Thus, some embodiments of the methods provide a method for performing nucleic acid-guided nickase/reverse transcriptase fusion editing in a target locus in a genome of a live cell utilizing two CF editing cassettes comprising: providing a cell with the target locus; providing a nucleic acid-guided nuclease/reverse transcriptase fusion enzyme; providing first and second CF editing cassettes, wherein the first and second CF editing cassettes have regions of complementarity to opposite strands of the target locus; wherein the first CF editing cassette comprises from 5' to 3': (1) a first CFgRNA comprising a spacer region and a scaffold region recognized by a corresponding nuclease or nickase (i.e., a scaffold); and (2) a first repair template comprising an optional post-edit homology region, an edit, a nick-to-edit region, and a primer binding site (PBS), with complementarity to a reverse transcribed DNA encoded by the second CF editing cassette; and wherein the second CF editing cassette comprises from 5' to 3': (1) a second CFgRNA comprising spacer region and a scaffold region; and (2) a second repair template comprising an optional post-edit homology region, an edit, a nick-to-edit region, and a PBS, with complementarity to a reverse transcribed DNA encoded by the first CF editing cassette; providing conditions to allow the nucleic acid-guided nuclease/reverse transcriptase fusion enzyme and CF editing cassettes to bind to the opposite strands of the target locus; and allowing the nucleic acid-guided nuclease/reverse transcriptase fusion enzyme and CF editing cassettes to edit the target locus.

In some aspects of this method, the CF editing cassettes further comprise an edit (e.g., on the repair template) to immunize the target locus to prevent re-nicking. As discussed herein, in some aspects, an edit to immunize the target locus to prevent re-nicking is one that alters the proto-spacer adjacent motif (or other element) such that binding or nicking at the edited target site by the nucleic acid-guided polypeptide (e.g., nuclease, nickase, inactive nuclease or inactive nickase) is impaired or prevented.

In some aspects of this method, the nick-to-edit region of at least one of the first or second repair templates is from 2-250 nucleotides in length, or from 5-150 nucleotides in length, or from 0-150 nucleotides in length. In some aspects of this method, the nick-to-edit region of at least one of the first or second repair templates is up to 10,000 nucleotides in length, or up to 3,000 nucleotides in length.

In some aspects, the region of complementarity between the first and second CF editing cassettes is from 4-120 nucleotides in length, or from 5-80 nucleotides in length, or from 6-60 nucleotides in length. In some aspects, the region of complementarity is from 1-120 nucleotides in length, 1-80 nucleotides in length, or from 1-60 nucleotides in length.

In some aspects, the edit region of the first and second repair templates is from 1-750 nucleotides in length, or from 1-500 nucleotides in length, or from 1-150 nucleotides in length.

In some aspects of the method, the post-edit homology region of at least one of the first or second templates is from 2-50 nucleotides in length, from 4-40 nucleotides in length, or from 5-25 nucleotides in length.

In some aspects, the edit created in the target locus is a single base swap in the target locus.

In some aspects, the edit created in the target locus is an insertion in the target locus. For example, in some aspects, the edit created in the target locus is an insertion of up to 50,000 nucleotides or more.

In some aspects, the edit created is an insertion of recombinase sites, protein degron tags, promoters, terminators, alternative-splice sites, CpG islands, insulators, transcription factor binding sites, etc.

In some aspects, the edit created in the target locus is a deletion in the target locus. For example, in some aspects, the edit created in the target locus is a deletion of up to 50,000 nucleotides or more.

In some aspects, the edit created is a deletion of genes, introns, exons, repetitive elements, promoters, terminators, insulators, CpG islands, non-coding elements, retrotransposons, etc.

In some aspects, the edit created is a deletion of up to 50,000 nucleotides or more, with an insertion of up to 50,000 nucleotides or more.

In some aspects, the edit created in the target locus is in a coding region in the target locus.

In some aspects, the edit created in the target locus is in a noncoding region in the target locus.

In some aspects of the method, the nuclease portion of the nickase/reverse transcriptase fusion includes a MAD2007 nickase.

In some aspects of the method, the nuclease portion of the nickase/reverse transcriptase fusion includes a MAD2017 nickase.

In some aspects of the method, the nuclease portion of the nickase/reverse transcriptase fusion includes a MAD2019 nickase.

In some aspects of the method, the nuclease portion of the nickase/reverse transcriptase fusion includes a MAD297 nickase In some aspects of the method, the nuclease portion of the nickase/reverse transcriptase fusion includes a MAD298 nickase In some aspects of the method, the nuclease portion of the nickase/reverse transcriptase fusion includes a MAD299 nickase In some aspects of the method, the nuclease portion of the nickase/reverse transcriptase fusion includes a MAD7 nickase.

In some aspects of the method, the nuclease portion of the nickase/reverse transcriptase fusion includes a Cas9 nickase.

In some aspects of the method, the reverse transcriptase portion of the nickase/reverse transcriptase fusion is selected from an HIV-1 reverse transcriptase, an M-MLV reverse transcriptase, an AMV reverse transcriptase, and an RSV reverse transcriptase. In some aspects, the reverse transcriptase comprises a Tfl transcriptase, such as described in U.S. App. Ser. No. 63/306,062.

Some embodiments of the methods further provide a method for performing nucleic acid-guided nickase/reverse transcriptase fusion editing to produce an edit in a target locus in a genome of a live cell comprising: providing a cell with the target locus; providing a fusion enzyme comprising a first nickase activity, a reverse transcriptase activity, and a second nickase activity, wherein the first nickase activity is nucleic acid-guided, and wherein optionally the fusion enzyme comprises, in order from amino terminus to carboxy terminus, a nucleic acid-guided first nickase, a reverse transcriptase, and a second nickase; providing a CF editing cassette, wherein the CF editing cassettes comprises, from 5' to 3', the following regions: a CFgRNA comprising a spacer sequence and a scaffold region, an optional post-edit homology region, an edit region, a nick-to-edit region, and a PBS region; providing conditions to allow the fusion enzyme and CF editing cassette to bind to the target locus; and allowing the fusion enzyme and CF editing cassette to edit the target locus.

In some aspects of the method, the CF editing cassette further comprises an edit (e.g., 1, 2, 3, 4, 5, or up to 10 edits), e.g., on the repair template, to immunize the target locus to prevent re-nicking.

In some aspects, the nick-to-edit region is from 0-150 nucleotides in length, from 2-250 nucleotides in length, or from 5-150 nucleotides in length, e.g., from 0-10 nucleotides in length, 10-20 nucleotides in length, 20-50 nucleotides in length, or 50-100 nucleotides in length. In some aspects of this method, the nick-to-edit region is up to 10,000 nucleotides in length, or up to 3,000 nucleotides in length.

In some aspects, the edit region of the CF editing cassette is from 1-750 nucleotides in length, for example from 1-500 nucleotides in length or from 1-150 nucleotides in length, e.g., from 1-10 nucleotides in length, 10-20 nucleotides in length, 20-50 nucleotides in length, 50-100 nucleotides, 100-250 nucleotides, 250-500 nucleotides, or 500-750 nucleotides in length.

In some aspects, the CF editing cassette is designed to provide a deletion of from 1 to 750 nucleotides at the target site. In some aspects, the CF editing cassette is designed to provide a deletion of from 1 to 10 nucleotides, from 10 to 20 nucleotides, from 20 to 50 nucleotides, from 50 to 100 nucleotides, from 100 to 200 nucleotides, from 200 to 500 nucleotides or from 250 to 750 nucleotides at the target site. In some aspects, the CF editing cassette is designed to provide a deletion of at least 20,000 nucleotides, such as at least 25,000 nucleotides, such as at least 30,000 nucleotides.

In some aspects, the post-edit homology region of the repair template is from 0-50 nucleotides in length. In some aspects, the post-edit homology region of the repair template is from 2 to 50 nucleotides in length, from 4 to 40 nucleotides in length, or from 5-25 nucleotides in length. In some aspects, the post-edit homology region of the repair template is from 1 to 5 nucleotides in length, from 5 to 10 nucleotides in length, or from 10-20 nucleotides in length.

In some aspects, the edit is selected from the group consisting of a single base swap in the target locus, an insertion in the target locus, a deletion in the target locus, an edit in a coding region in the target locus, and an edit in a noncoding region in the target locus. In some aspects, the edit is a single base swap in the target locus, an insertion in the target locus, or a deletion in the target locus. In some aspects, the edit is in a coding region in the target locus or the edit is in a noncoding region in the target locus. In some aspects, the edit comprises several of these types of edits and/or comprises more than one of one or more of these types of edits. For example, in some aspects, the edit comprises two or more base swaps (e.g., 2, 3, 4, 5, or from 1 to 20 base swaps), some or all of which can be adjacent to each other or nonadjacent to each other. In some aspects, the edit comprises one or more base swaps (e.g., 2, 3, 4, 5, or from 1 to 20 base swaps) and an insertion of one or more nucleotides (e.g., 2, 3, 4, 5, or from 1 to 20 nucleotides). In some aspects, the edit comprises one or more base swaps (e.g., 2, 3, 4, 5, or from 1 to 20 base swaps) and a deletion of one or more nucleotides (e.g., 1, 2, 3, 4, 5, or from 1 to 10,000 nucleotides). In some aspects, the edit comprises one or more insertions (e.g., 2, 3, 4, 5, up to 100 bp insertions) and a deletion of one or more nucleotides (e.g., 2, 3, 4, 5, or from 1 to 10,000 nucleotides).

In some aspects, the fusion enzyme comprises, in order from amino terminus to carboxy terminus, a nucleic acid-guided first nickase, a reverse transcriptase, and a second nickase, and wherein the second nickase recognizes and nicks a single DNA sequence, a set of related DNA sequences, or all DNA sequences. In some aspects, the order of fusion enzyme components can differ from the above and can be in any amino- to carboxy-terminus order, such as, for example, a nucleic acid-guided first nickase, a second nickase, and a reverse transcriptase; a second nickase, a nucleic acid-guided first nickase, and a reverse transcriptase; or a second nickase, a reverse transcriptase, and a nucleic acid-guided first nickase.

In some aspects, the nucleic acid-guided first nickase is a Cas9 nickase, a MAD2007 nickase, a MAD2017 nickase, a MAD2019 nickase, a MAD297 nickase, a MAD298 nickase, a MAD299 nickase, or a MAD7 nickase.

In some aspects, the reverse transcriptase is selected from the group consisting of an HIV-1 reverse transcriptase, an M-MLV reverse transcriptase, an AMV reverse transcriptase, and an RSV reverse transcriptase. In some aspects, the reverse transcriptase comprises a Tfl transcriptase, such as described in U.S. App. Ser. No. 63/306,062.

Some embodiments of the methods further provide a method for performing nucleic acid-guided nickase/reverse transcriptase/nucleic acid-guided nickase fusion editing to produce an edit in a target locus in a genome of a live cell utilizing two CF editing cassettes comprising: providing a cell with the target locus; providing a fusion enzyme comprising, in order from amino terminus to carboxy terminus, a first Cas9 nickase, a reverse transcriptase, and a second Cas9 nickase, wherein the first Cas9 nickase and the second Cas9 nickase are orthologues of each other; providing first and second CF editing cassettes, wherein the first and second CF editing cassettes have regions of complementarity to opposite strands of the target locus, and wherein the first CF editing cassette can combine with the first Cas9 nickase to form a first functional Cas9 ribonucleoprotein (RNP), and the second CF editing cassette can combine with the second Cas9 nickase to form a second functional Cas9 ribonucleoprotein (RNP); and wherein: the first CF editing cassette comprises, from 5' to 3', the following regions: (1) a first CFgRNA comprising a first spacer sequence which is complementary to a first strand of the target locus and a first scaffold region; and (2) a first repair template comprising a first optional post-edit homology region, a first edit region, a first nick-to-edit region, and a first primer binding site; and the second CF editing cassette comprises, from 5' to 3', the following regions: (1) a second CFgRNA comprising a second spacer sequence which is complementary to a second strand of the target locus and a second scaffold region; and (2) a second repair template comprising a second optional post-edit homology region, a second edit region, a second nick-to-edit region, and a second primer binding site; and wherein: the first edit region is complementary to the second edit region; the method further comprising providing conditions to allow the fusion enzyme and CF editing cassettes to bind to the target locus; and allowing the fusion enzyme and CF editing cassettes to edit the target locus.

In some aspects of the method, one or both of the CF editing cassettes further comprises an edit (e.g., 1, 2, 3, 4, 5, or up to 10 edits) to immunize the target locus to prevent re-nicking.

In some aspects, the nick-to-edit region of one or both of the repair templates is from 0-150 nucleotides in length, from 2-250 nucleotides in length, or from 5-150 nucleotides in length, e.g., from 0-10 nucleotides in length, 10-20 nucleotides in length, 20-50 nucleotides in length, or 50-100 nucleotides in length. In some aspects of this method, the nick-to-edit region of at least one or both of the repair templates is up to 10,000 nucleotides in length, or up to 3,000 nucleotides in length.

In some aspects, one or both of a first region of complementarity of the first CF editing cassette and a second region of complementarity of the second CF editing cassette is from 0 to 120 nucleotides in length, such as from 4 to 120 nucleotides in length, from 5 to 80 nucleotides in length, or from 6 to 60 nucleotides in length, e.g., from 0-10 nucleotides in length, 10-20 nucleotides in length, 20-50 nucleotides in length, or 50-100 nucleotides in length.

In some aspects, the first edit region and the second edit region are from 1-750 nucleotides in length, for example from 1-500 nucleotides in length or from 1-150 nucleotides in length, e.g., from 1-10 nucleotides in length, 10-20 nucleotides in length, 20-50 nucleotides in length, or 50-100 nucleotides in length. The first edit region and the second edit region are complementary to each other and are of the same length.

In some aspects, an edit is dividedly encoded by (i.e., split between) the first and second CF editing cassettes, wherein the first edit region and the second edit region encode only portions of the edit. In such aspects, the first and second edit regions comprise an overlapping region. In such aspects, the first and second edit regions may or may not have the same length.

In some aspects, the first and second CF editing cassettes are designed to provide a deletion of from 1 to 750 nucleotides at the target site. In some aspects, the first and second CF editing cassettes are designed to provide a deletion of from 1 to 10 nucleotides, from 10 to 20 nucleotides, from 20 to 50 nucleotides, from 50 to 100 nucleotides, from 100 to 200 nucleotides, from 200 to 500 nucleotides or from 250 to 750 nucleotides at the target site. In some aspects the first and second CF editing cassettes are designed to provide a deletion of up to 20,000 nucleotides or more, such as up to 50,000 nucleotides or more.

In some aspects, one or both of the first post-edit homology region and the second post-edit homology region is/are from 0-50 nucleotides in length. In some aspects, one or both of the post-edit homology regions is/are from 2 to 50 nucleotides in length, from 4 to 40 nucleotides in length, or from 5-25 nucleotides in length. In some aspects, one or both of the post-edit homology regions is/are from 1 to 5 nucleotides in length, from 5 to 10 nucleotides in length, from 10-20 nucleotides in length, or from 20-50 nucleotides in length.

In some aspects, the edit is selected from the group consisting of a single base swap in the target locus, an insertion in the target locus, a deletion in the target locus, an edit in a coding region in the target locus, and an edit in a noncoding region in the target locus. In some aspects, the edit is a single base swap in the target locus, an insertion in the target locus, or a deletion in the target locus. In some aspects, the edit is in a coding region in the target locus or the edit is in a noncoding region in the target locus. In some aspects, the edit comprises several of these types of edits and/or comprises more than one of one or more of these types of edits. For example, in some aspects, the edit comprises two or more base swaps (e.g., 2, 3, 4, 5, or from 1 to 20 base swaps), some or all of which can be adjacent to each other or not adjacent to each other. In some aspects, the edit comprises one or more base swaps (e.g., 2, 3, 4, 5, or from 1 to 20 base swaps) and an insertion of one or more nucleotides (e.g., 2, 3, 4, 5, or from 1 to 20 nucleotides). In some aspects, the edit comprises one or more base swaps (e.g., 2, 3, 4, 5, or from 1 to 20 base swaps) and a deletion of one or more nucleotides (e.g., 2, 3, 4, 5, or from 1 to 10,000 nucleotides). In some aspect, the edit comprises one or more insertions (e.g., 2, 3, 4, 5, up to 100 bp insertions) and a deletion of one or more nucleotides (e.g., 2, 3, 4, 5, or from 1 to 10,000 nucleotides).

In some aspects, the reverse transcriptase is selected from the group consisting of an HIV-1 reverse transcriptase, an M-MLV reverse transcriptase, an AMV reverse transcriptase, and an RSV reverse transcriptase. In some aspects, the reverse transcriptase comprises a Tfl transcriptase, such as described in U.S. App. Ser. No. 63/306,062.

Some embodiments of the methods further provide a method for performing nucleic acid-guided nickase/reverse transcriptase/nucleic acid-guided nickase fusion editing to produce an edit in a target locus in a genome of a live cell utilizing two CF editing cassettes comprising: providing a cell with the target locus; providing a fusion enzyme comprising, in order from amino terminus to carboxy terminus, a first Cas9 variant, a reverse transcriptase, and a second Cas9 variant, wherein the first Cas9 variant and the second Cas9 variant are orthologues of each other; providing first and second CF editing cassettes, wherein the first CF editing cassettes comprises from 5' to 3': (1) a first CFgRNA comprising a spacer region and a scaffold region; and (2) a first repair template comprising an optional post-edit homology region, an edit region, a nick-to-edit region, and a primer binding site region; providing conditions to allow the fusion enzyme and CF editing cassettes to bind to the target locus; and allowing the fusion enzyme and CF editing cassettes to edit the target locus.

In some aspects of the method, the first CF editing cassettes further comprises an edit (e.g., 1, 2, 3, 4, 5, or up to 10 edits) to immunize the target locus to prevent re-nicking.

In some aspects, the first Cas9 variant is a catalytically active Cas9 nickase or nuclease and the second Cas9 variant is a catalytically inactive Cas9 nickase or nuclease, e.g., dCas9. In such aspects, the first and second nick are created by the catalytically active Cas9 and generate a double-stranded break (DSB), or the first nick is created by the catalytically active Cas9 and the second nick is created by an additional nickase. In some aspects, the catalytically inactive Cas9 reduces the PAM specificity of the catalytically active Cas9.

In some aspects, the nick-to-edit region of the first repair template is from 0-150 nucleotides in length, from 2-250 nucleotides in length, or from 5-150 nucleotides in length, e.g., from 0-10 nucleotides in length, 10-20 nucleotides in length, 20-50 nucleotides in length, or 50-100 nucleotides in length. In some aspects of this method, the nick-to-edit region of the first repair template is up to 10,000 nucleotides in length, or up to 3,000 nucleotides in length.

In some aspects, the edit region is from 1-750 nucleotides in length, for example from 1-500 nucleotides in length or from 1-150 nucleotides in length, e.g., from 1-10 nucleotides in length, 10-20 nucleotides in length, 20-50 nucleotides in length, or 50-100 nucleotides in length. In some aspects, the edit region is up to 3,000 nucleotides in length or more.

In some aspects, the first CF editing cassette is designed to provide a deletion of from 1 to 750 nucleotides at the target site. In some aspects, the first CF editing cassette is designed to provide a deletion of from 1 to 10 nucleotides, from 10 to 20 nucleotides, from 20 to 50 nucleotides, from 50 to 100 nucleotides, from 100 to 200 nucleotides, from 200 to 500 nucleotides or from 250 to 750 nucleotides at the target site. In some aspects, the deletion up to 20,000 nucleotides or more, such as 50,000 nucleotides or more.

In some aspects, the post-edit homology region is from 0-50 nucleotides in length. In some aspects, the post-edit homology region is from 2 to 50 nucleotides in length, from 4 to 40 nucleotides in length, or from 5-25 nucleotides in length. In some aspects, the post-edit homology regions is from 1 to 5 nucleotides in length, from 5 to 10 nucleotides in length, from 10-20 nucleotides in length, or from 20-50 nucleotides in length.

In some aspects, the edit is selected from the group consisting of a single base swap in the target locus, an insertion in the target locus, a deletion in the target locus, an edit in a coding region in the target locus, and an edit in a noncoding region in the target locus. In some aspects, the edit is a single base swap in the target locus, an insertion in the target locus, or a deletion in the target locus. In some aspects, the edit is in a coding region in the target locus or the edit is in a noncoding region in the target locus. In some aspects, the edit comprises several of these types of edits and/or comprises more than one of one or more of these types of edits. For example, in some aspects, the edit comprises two or more base swaps (e.g., 2, 3, 4, 5, or from 1 to 20 base swaps), some or all of which can be adjacent to each other or not adjacent to each other. In some aspects, the edit comprises one or more base swaps (e.g., 2, 3, 4, 5, or from 1 to 20 base swaps) and an insertion of one or more nucleotides (e.g., 2, 3, 4, 5, or from 1 to 20 nucleotides). In some aspects, the edit comprises one or more base swaps (e.g., 2, 3, 4, 5, or from 1 to 20 base swaps) and a deletion of one or more nucleotides (e.g., 2, 3, 4, 5, or from 1 to 10,000 nucleotides). In some aspects, the edit comprises one or more insertions (e.g., 2, 3, 4, 5, up to 100 bp insertions) and a deletion of one or more nucleotides (e.g., 2, 3, 4, 5, or from 1 to 10,000 nucleotides).

In some aspects, the reverse transcriptase is selected from the group consisting of an HIV-1 reverse transcriptase, an M-MLV reverse transcriptase, an AMV reverse transcriptase, and an RSV reverse transcriptase. In some aspects, the reverse transcriptase comprises a Tfl transcriptase, such as described in U.S. App. Ser. No. 63/306,062.

Some embodiments of the methods further provide a method for performing fusion protein editing to produce an edit in a target locus comprising a top DNA strand and a bottom DNA strand in a genome of a live cell comprising: providing a cell with the target locus; providing a fusion enzyme comprising, in order from amino terminus to carboxy terminus, either: a first nickase, a nucleic acid-guided second nickase, and a reverse transcriptase, or, a Cas9 nuclease and a reverse transcriptase; providing a tracrRNA, wherein the tracrRNA comprises, from 5' to 3', a scaffold compatible with the provided nucleic acid-guided second nickase or with the provided Cas9 nuclease, a region of complementarity to a crRNA, a first optional post-edit homology region, a first edit region, a first nick-to-edit region, and a first primer binding site which is complementary to and can hybridize with the target locus top strand; providing the crRNA, wherein the crRNA comprises, from 5' to 3', a spacer sequence which is complementary to and can hybridize with the bottom strand of the target locus, a region of complementarity to the tracrRNA, a second optional post-edit homology region, a second edit region, a second nick-to-edit region, and a second primer binding site; wherein: the first edit region is complementary to the second edit region; a first region of complementarity exists between the first post-edit homology region and the second nick-to-edit region; a second region of complementarity exists between the second post-edit homology region and the first nick-to-edit region; and the 3' end of the crRNA comprises a region that is complementary to and can hybridize with the 5' end of the tracrRNA such that the fusion enzyme, crRNA and tracrRNA can form a functional fusion enzyme/crRNA/tracrRNA ribonucleoprotein complex; providing conditions to allow the fusion enzyme/crRNA/tracrRNA ribonucleoprotein complex to bind to the target locus; and allowing the fusion enzyme/crRNA/tracrRNA ribonucleoprotein complex to edit the target locus.

In some aspects, the first region of complementarity and/or the second region of complementarity are optional, depending on the length of the edit.

In some aspects, the fusion enzyme comprises, in order from amino terminus to carboxy terminus, a first nickase, a nucleic acid-guided second nickase, and a reverse transcriptase, and the nucleic acid-guided second nickase is joined or tethered to the reverse transcriptase by a flexible linker (e.g., (GGGGS)n (SEQ ID No 1)), and the nucleic acid-guided second nickase is joined or tethered to the first nickase by a rigid linker (e.g., A(EAAAK)nA (SEQ ID No 2)). In some aspects, the first nickase is a non-specific nickase, i.e., it nicks DNA in a non-sequence specific fashion. In some aspects, the order of fusion enzyme components can differ from the above and can be in any amino-to carboxy-terminus order, such as, for example, a nucleic acid-guided second nickase, a first nickase, and a reverse transcriptase; a first nickase, a reverse transcriptase, and a nucleic acid-guided second nickase; a nucleic acid-guided second nickase, a reverse transcriptase, and a first nickase, etc.

In some aspects of this method, one or both of the crRNA and the tracrRNA further comprise an edit (e.g., 1, 2, 3, 4, 5, or up to 10 edits) to immunize the target locus to prevent re-nicking.

In some aspects, the nick-to-edit region of one or both of the crRNA and the tracrRNA is from 0-150 nucleotides in length, from 2-250 nucleotides in length, or from 5-150 nucleotides in length, e.g., from 0-10 nucleotides in length, 10-20 nucleotides in length, 20-50 nucleotides in length, or 50-100 nucleotides in length. In some aspects, the nick-to-edit region of one or both of the crRNA and the tracrRNA is up to 10,000 nucleotides in length, or up to 3,000 nucleotides in length.

In some aspects, one or both of the first region of complementarity and the second region of complementarity is from 0 to 120 nucleotides in length, such as from 4 to 120 nucleotides in length, from 5 to 80 nucleotides in length, or from 6 to 60 nucleotides in length, e.g., from 0-10 nucleotides in length, 10-20 nucleotides in length, 20-50 nucleotides in length, or 50-100 nucleotides in length.

In some aspects, the edit region of the crRNA and the tracrRNA is from 1-750 nucleotides in length, for example from 1-500 nucleotides in length or from 1-150 nucleotides in length, e.g., from 1-10 nucleotides in length, 10-20 nucleotides in length, 20-50 nucleotides in length, 50-100 nucleotides, 100-250 nucleotides, 250-500 nucleotides, or 500-750 nucleotides in length. In some aspects, the crRNA edit region and the tracrRNA edit region are complementary to each other and are of the same length.

In some aspects, the cRNA edit region and the tracrRNA edit region each encode only a portion of the edit. In such aspects, the cRNA edit region and the tracrRNA edit region comprise an overlapping region, wherein the overlapping region is only a portion of the cRNA edit region and/or the tracrRNA edit region.

In some aspects, the fusion enzyme comprises a first nickase, a nucleic acid-guided second nickase, and a reverse transcriptase, and the crRNA and the tracrRNA are designed to provide a deletion of from 1 to 750 nucleotides at the target site. In some aspects, the crRNA and the tracrRNA are designed to provide a deletion of from 1 to 10 nucleotides, from 10 to 20 nucleotides, from 20 to 50 nucleotides, from 50 to 100 nucleotides, from 100 to 200 nucleotides, from 200 to 500 nucleotides or from 250 to 750 nucleotides at the target site. In some aspects, the deletion is up to 20,000 nucleotides or more, such as 50,000 nucleotides or more.

In some aspects, the post-edit homology region of one or both of the crRNA and the tracrRNA is from 0-50 nucleotides in length. In some aspects, one or both of the post-edit homology regions are from 2 to 50 nucleotides in length, from 4 to 40 nucleotides in length, or from 5-25 nucleotides in length. In some aspects, one or both of the post-edit homology regions are from 1 to 5 nucleotides in length, from 5 to 10 nucleotides in length, from 10-20 nucleotides in length, or from 20-50 nucleotides in length.

In some aspects, the edit is selected from the group consisting of a single base swap in the target locus, an insertion in the target locus, a deletion in the target locus, an edit in a coding region in the target locus, and an edit in a noncoding region in the target locus. In some aspects, the edit is a single base swap in the target locus, an insertion in the target locus, or a deletion in the target locus. In some aspects, the edit is in a coding region in the target locus or the edit is in a noncoding region in the target locus. In some aspects, the edit comprises several of these types of edits and/or comprises more than one of one or more of these types of edits. For example, in some aspects, the edit comprises two or more base swaps (e.g., 2, 3, 4, 5, or from 1 to 20 base swaps), some or all of which can be adjacent to each other or not adjacent to each other. In some aspects, the edit comprises one or more base swaps (e.g., 2, 3, 4, 5, or from 1 to 20 base swaps) and an insertion of one or more nucleotides (e.g., 2, 3, 4, 5, or from 1 to 20 nucleotides). In some aspects, the edit comprises one or more base swaps (e.g., 2, 3, 4, 5, or from 1 to 20 base swaps) and a deletion of one or more nucleotides (e.g., 2, 3, 4, 5, or from 1 to 10,000 nucleotides). In some aspects, the edit comprises one or more insertions (e.g., 2, 3, 4, 5, up to 100 bp insertions) and a deletion of one or more nucleotides (e.g., 2, 3, 4, 5, or from 1 to 10,000 nucleotides).

In some aspects, the fusion enzyme comprises a first nickase, a nucleic acid-guided second nickase, and a reverse transcriptase and the edit is a deletion in the target locus.

In some aspects, the fusion enzyme comprises a first nickase, a nucleic acid-guided second nickase, and a reverse transcriptase and the first nickase recognizes and can nick only a single DNA sequence, or the first nickase recognizes and can nick a set of related DNA sequences, or the first nickase is non-specific and can nick all sequences.

In some aspects, the reverse transcriptase is selected from the group consisting of an HIV-1 reverse transcriptase, an M-MLV reverse transcriptase, an AMV reverse transcriptase, and an RSV reverse transcriptase. In some aspects, the reverse transcriptase comprises a Tfl transcriptase, such as described in U.S. App. Ser. No. 63/306,062.

In some aspects, the fusion enzyme comprises a first nickase, a nucleic acid-guided second nickase, and a reverse transcriptase and the nucleic acid-guided first nickase is a Cas9 nickase. In some aspects, the fusion enzyme comprises a first nickase, a nucleic acid-guided second nickase, and a reverse transcriptase and the nucleic acid-guided first nickase is the MAD2007 nickase, a MAD2017 nickase, a MAD2019 nickase, a MAD297 nickase, a MAD298 nickase, a MAD299 nickase, or a MAD7 nickase.

Some embodiments of the methods further provide a method for performing fusion protein editing to produce an edit in a target locus comprising a top DNA strand and a bottom DNA strand in a genome of a live cell comprising: providing a cell with the target locus; and providing a first polypeptide and a second polypeptide, wherein the first polypeptide is a first fusion enzyme that comprises a catalytically inactive type V nucleic acid guided nuclease, a first nickase and a reverse transcriptase, or the first polypeptide is a first fusion enzyme that comprises a catalytically inactive type II nucleic acid guided nickase and a reverse transcriptase, or the first polypeptide is a first fusion enzyme that comprises a catalytically active type V nucleic acid guided nickase and a reverse transcriptase, and the second polypeptide is a second fusion enzyme that comprises a catalytically inactive type II nucleic acid guided nuclease and a second nickase, or the second polypeptide comprises a catalytically active type II nucleic acid guided nickase.

In some aspects, the method further comprises: providing a dual CF editing cassette comprising, from 5' to 3': (1) a first CFgRNA comprising a first scaffold and a first guide sequence; and (2) a repair template comprising a first optional post-edit homology region, a first edit region, a first nick-to-edit region, and a first primer binding site, wherein the first scaffold is compatible with a type V nucleic acid guided nuclease, a second guide sequence, a second scaffold, a second optional post-edit homology region, a second edit region, a second nick-to-edit region, and a second primer binding site, wherein the second scaffold is compatible with a type II nucleic acid guided nuclease; wherein: the first edit region is complementary to the second edit region; a first region of complementarity exists between the first post-edit homology region, the edit region, and the second nick-to-edit region and/or second primer binding site; a second region of complementarity exists between the second post-edit homology region, the edit region, and the first nick-to-edit region and/or first primer binding site; and providing conditions to allow the first polypeptide, the second polypeptide and the dual guide RNA to associate with each other and bind to the target locus; and allowing the first polypeptide, the second polypeptide and the dual guide RNA to edit the target locus.

In some aspects, the dual CF editing cassette further comprises one or more edits (e.g., 1, 2, 3, 4, 5, or up to 10 edits) to immunize the target locus to prevent re-nicking.

In some aspects, one or both of the nick-to-edit regions is from 0-150 nucleotides in length, from 2-250 nucleotides in length, or from 5-150 nucleotides in length, e.g., from 0-10 nucleotides in length, 10-20 nucleotides in length, 20-50 nucleotides in length, or 50-100 nucleotides in length. In some aspects of this method, one or both of the nick-to-edit regions is up to 10,000 nucleotides in length, or up to 3,000 nucleotides in length.

In some aspects, one or both of the first region of complementarity and the second region of complementarity is 0 to 120 nucleotides in length, such as from 4 to 120 nucleotides in length, from 5 to 80 nucleotides in length, or from 6 to 60 nucleotides in length, e.g., from 0-10 nucleotides in length, 10-20 nucleotides in length, 20-50 nucleotides in length, or 50-100 nucleotides in length.

In some aspects, the first edit region and the second edit region are from 1-750 nucleotides in length, for example from 1-500 nucleotides in length or from 1-150 nucleotides in length, e.g., from 1-10 nucleotides in length, 10-20 nucleotides in length, 20-50 nucleotides in length, 50-100 nucleotides, 100-250 nucleotides, 250-500 nucleotides, or 500-750 nucleotides in length. In some aspects, the first edit region and the second edit region are complementary to each other and are of the same length.

In some aspects, the dual CF editing cassette is designed to provide a deletion of from 1 to 750 nucleotides at the target site. In some aspects, the dual CF editing cassette is designed to provide a deletion of from 1 to 10 nucleotides, from 10 to 20 nucleotides, from 20 to 50 nucleotides, from 50 to 100 nucleotides, from 100 to 200 nucleotides, from 200 to 500 nucleotides or from 250 to 750 nucleotides at the target site. In some aspects, the deletion is up to 20,000 nucleotides or more, such as 50,000 nucleotides or more.

In some aspects, one or both of the first post-edit homology region and the second post-edit homology region is/are from 0-50 nucleotides in length. In some aspects, one or both of the post-edit homology regions is/are from 2 to 50 nucleotides in length, from 4 to 40 nucleotides in length, or from 5-25 nucleotides in length. In some aspects, one or both of the post-edit homology regions is/are from 1 to 5 nucleotides in length, from 5 to 10 nucleotides in length, from 10-20 nucleotides in length, or from 20-50 nucleotides in length.

In some aspects, the edit is selected from the group consisting of a single base swap in the target locus, an insertion in the target locus, a deletion in the target locus, an edit in a coding region in the target locus, and an edit in a noncoding region in the target locus. In some aspects, the edit is a single base swap in the target locus, an insertion in the target locus, or a deletion in the target locus. In some aspects, the edit is in a coding region in the target locus or the edit is in a noncoding region in the target locus. In some aspects, the edit comprises several of these types of edits and/or comprises more than one of one or more of these types of edits. For example, in some aspects, the edit comprises two or more base swaps (e.g., 2, 3, 4, 5, or from 1 to 20 base swaps), some or all of which can be adjacent to each other or not adjacent to each other. In some aspects, the edit comprises one or more base swaps (e.g., 2, 3, 4, 5, or from 1 to 20 base swaps) and an insertion of one or more nucleotides (e.g., 2, 3, 4, 5, or from 1 to 20 nucleotides). In some aspects, the edit comprises one or more base swaps (e.g., 2, 3, 4, 5, or from 1 to 20 base swaps) and a deletion of one or more nucleotides (e.g., 2, 3, 4, 5, or from 1 to 10,000 nucleotides). In some aspects, the edit comprises one or more insertions (e.g., 2, 3, 4, 5, up to 100 bp insertions) and a deletion of one or more nucleotides (e.g., 2, 3, 4, 5, or from 1 to 10,000 nucleotides).

In some aspects, the reverse transcriptase is selected from the group consisting of an HIV-1 reverse transcriptase, an M-MLV reverse transcriptase, an AMV reverse transcriptase, and an RSV reverse transcriptase. In some aspects, the reverse transcriptase comprises a Tfl transcriptase, such as described in U.S. App. Ser. No. 63/306,062.

In some aspects, the first polypeptide comprises: a catalytically inactive type V nucleic acid guided nuclease, wherein the catalytically inactive type V nucleic acid guided nuclease is dMAD7, or a catalytically active type V nucleic acid guided nickase, wherein the catalytically active type V nucleic acid guided nickase is MAD7, MAD297, MAD298, or MAD299 nickase; and the second polypeptide comprises: a catalytically inactive type II nucleic acid guided nuclease, wherein the catalytically inactive type II nucleic acid guided nuclease is dMAD2007, or a catalytically active type II nucleic acid guided nickase, wherein the catalytically active type II nucleic acid guided nickase is MAD2007 or MAD 2019 nickase.

In some aspects, the reverse transcriptase is selected from the group consisting of an HIV-1 reverse transcriptase, an M-MLV reverse transcriptase, an AMV reverse transcriptase, and an RSV reverse transcriptase. In some aspects, the reverse transcriptase comprises a Tfl transcriptase, such as described in U.S. App. Ser. No. 63/306,062.

In various aspects of the various methods described herein, fusion proteins are sometimes described in certain amino to carboxy terminus sequences of their protein components. Various aspects of the methods disclosed herein employ fusion proteins that comprise the same protein components ordered in a different sequence.

In some aspects, CFgRNAs or CF editing cassettes comprise a "landing pad" sequence, or a sequence of nucleotides comprising an enzyme recognition sequence, such as a recombinase, integrase, nuclease, or meganuclease recognition sequence. The landing pad can be leveraged to insert/integrate additional, large donor nucleic acid sequences (i.e., large DNA payloads), including heterologous genes or pathways, or entire plasmids, in recursive editing operations. For example, after an initial editing operation wherein a landing pad is integrated into a genome, a subsequent editing operation utilizing a vector comprising an additional donor DNA sequence and a coding sequence for, e.g., a recombinase, integrase, nuclease, or meganuclease may be performed. Constitutive expression or induced expression of the coded enzyme may facilitate insertion of the additional donor DNA sequence into the previously-integrated landing pad.

In some aspects, the landing pad consists of two recombinase sites. Introduction of a compatible donor DNA sequence and recombinase enzyme(s) recognizing these sites may enable unidirectional integration of large donor DNA sequences in a strategy known as RMCA (recombinase mediated cassette exchange).

In some aspects, the landing pad and integration may enable the integration of a library of gRNAs, CF editing cassettes, and/or barcodes, which facilitates long-term trackability of components that edit elsewhere in the genome. For example, integration of a landing pad, followed by integration of a CF editing cassette at a safe harbor locus, will enable long-term trackability of a very DNA that works to create an edit elsewhere in the genome. This enables trackability of pool-based based editing without random integration common of lentiviral techniques.

In specific aspects, the recombinase is a cyclization recombination enzyme (Cre) and the landing pad and/or additional donor DNA sequence comprise lox recombination sites. In specific aspects, the recombinase is a flippase enzyme and the landing pad and/or additional donor DNA sequence comprise flippase recognition targets (FRTs).

In specific aspects, the vector carrying the additional donor DNA sequence comprises a coding sequence for a meganuclease, the landing pads comprise a recognition sequence for the meganuclease, and the additional donor DNA sequence comprises homologous sequences flanking the DNA payload. In some aspects, the meganuclease belongs to the LAGLIDADG (SEQ ID No 3) family of nucleases, and in some aspects, the meganuclease is I-SceI; the meganuclease is I-CreI; or the meganuclease is I-DmoI.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 1C is a simplified depiction of dual CF editing cassette nickase-RT fusion editing showing the target locus, the nickase-RT and the dual CF editing cassettes. FIG. 1D at top is a table giving the spacer, scaffold, post-edit homology, edit, nick-to-edit and primer binding sequences of three exemplary complementary CF editing cassettes used in experiments described in Example IV, and additionally FIG. 1D at bottom shows how the sequences from complementary CF editing cassettes (i.e., CF 13-8 and C5-25 as well as 13-8 and 19-8) relate to one another. CF editing cassette C5-25 (SEQ ID No 4) comprises a spacer sequence (SEQ ID No 5), a scaffold sequence (SEQ ID No 6), a post-edit homology sequence (SEQ ID No 7), an edit sequence, a nick-to-edit sequence (SEQ ID No 8), and a primer binding region sequence (SEQ ID No 9); CF editing cassette 13-8 (SEQ ID No 10) comprises a spacer sequence (SEQ ID No 11), a scaffold sequence (SEQ ID No 12), a post-edit homology sequence, an edit sequence, a nick-to-edit sequence (SEQ ID No 13), and a primer binding region sequence (SEQ ID No 14); and CF editing cassette 19-8 (SEQ ID No 15) comprises a spacer sequence (SEQ ID No 16), a scaffold sequence (SEQ ID No 17), a post-edit homology sequence, an edit sequence, a nick-to-edit sequence (SEQ ID No 18), and a primer binding region sequence (SEQ ID No 19).

FIG. 1G is a simplified depiction of nickase-RT fusion editing utilizing a nickase-RT fusion enzyme and a single CF editing cassette.

FIGS. 1O-1P are simplified depictions of an exemplary method for nickase-RT fusion editing of live cells utilizing landing bands.

FIGS. 4A-4C depict various components of exemplary embodiments of a bioreactor module included in an integrated instrument useful for growing and transfecting cells.

It should be understood that the drawings are not necessarily to scale, and that like reference numbers refer to like features.

DETAILED DESCRIPTION

Figure 1A:
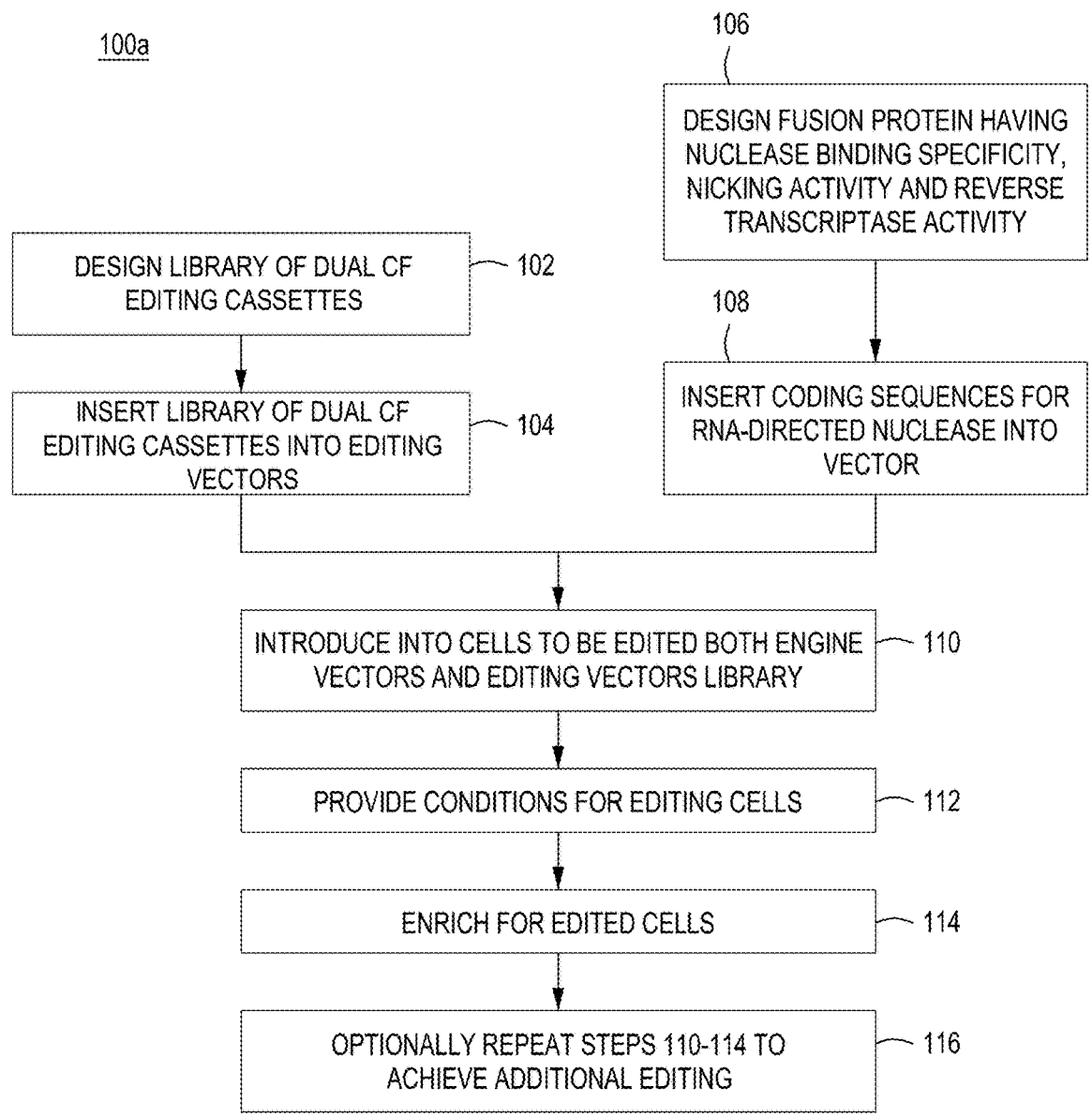
FIG. 1A is a simplified block diagram of an exemplary method for editing live cells utilizing dual CF editing cassettes and a nucleic acid-guided nickase/reverse transcriptase fusion ("nickase-RT fusion") enzyme.

All of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) Biochemistry (4th Ed.) W.H. Freeman, New York N.Y.; Gait, "*Oligonucleotide Synthesis: A Practical Approach*" 1984, IRL Press, London; Nelson and Cox (2000), Lehninger, *Principles of Biochemistry* $3^{rd}$ Ed., W. H. Freeman Pub., New York, N.Y.; Berg et al. (2002) *Biochemistry*, $5^{th}$ Ed., W.H. Freeman Pub., New York, N.Y.; all of which are herein incorporated in their entirety by reference for all purposes. CRISPR-specific techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "an oligonucleotide" refers to one or more oligonucleotides, and reference to "an automated system" includes reference to equivalent steps and methods for use with the system known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "amino acid" refers to naturally occurring and synthetic amino acids, as well as amino acid analogs that function similarly to naturally occurring amino acids.

The terms "cassette," "expression cassette," "editing cassette," "CREATE cassette," "CREATE editing cassette," "CREATE fusion editing cassette," or "CF editing cassette" in the context of the current methods and compositions refer to a nucleic acid molecule comprising a coding sequence for transcription of a guide nucleic acid (gRNA), e.g., a CFgRNA, covalently linked to a coding sequence for transcription of a repair template to effect editing in a nucleic acid-guided nickase/reverse transcriptase fusion system. In certain embodiments, "CF editing cassette" refers to a nucleic acid molecule comprising a coding sequence for transcription of two gRNAs, wherein each gRNA sequence is covalently linked to a coding sequence for transcription of a repair template, to effect editing in a nucleic acid-guided nickase/reverse transcriptase fusion system. In certain embodiments, "CF editing cassette" refers to a nucleic acid molecule comprising a guide nucleic acid or gRNA covalently linked to a repair template. The terms "complementary CF editing cassettes" refers to two CF editing cassettes engineered to bind to and edit opposite DNA strands in a target locus.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

The terms "CREATE fusion enzyme" or "CF enzyme" or the terms "nickase fusion" or "nickase fusion enzyme" refer to a nucleic acid-guided nickase fused to a reverse transcriptase where the fused enzyme both binds and nicks a target sequence in a sequence-specific manner and is capable of utilizing a repair template to incorporate nucleotides into the target sequence at the site of the nick.

The terms "CREATE fusion gRNA" or "CFgRNA" refer to a gRNA engineered to function with a nucleic acid-guided nickase/reverse transcriptase fusion enzyme (a "nickase-RT fusion") where the CFgRNA is designed to bind to and facilitate editing of opposite DNA strands in a target locus. In certain embodiments, "CREATE fusion gRNA" or "CFgRNA" refer to one of two gRNAs engineered to function with a nucleic acid-guided nickase/reverse transcriptase fusion enzyme (a "nickase-RT fusion") where the two CFgRNAs are designed to bind to and facilitate editing of opposite DNA strands in a target locus. The terms "complementary CFgRNAs" refers to two CFgRNAs engineered to bind to opposite DNA strands in a target locus, which often facilitate creation of complementary edits at a site in the target locus. Certain embodiments of the methods disclosed herein use only a single CFgRNA, in a CF editing cassette, that is designed to bind to and facilitate editing of one or both DNA strands in a target locus.

The term "donor DNA" refers to an exogenous piece of DNA with sequences that allow it to be integrated into another sequence, e.g., the cellular genome. In certain embodiments, a donor DNA may be integrated into a landing pad with an integrase or recombinase.

The term "gene" refers to a segment of DNA involved in producing a polypeptide chain. It may include regions preceding and following a coding region (leader and trailer, respectively), as well as intervening sequences (introns) between individual coding segments (exons).

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

The term "heterologous" refers to the relationship between two or more nucleic acids or protein sequences from different sources, or the relationship between a protein (or nucleic acid) and a host cell from different sources. For example, if the combination of a nucleic acid and a host cell is usually not naturally occurring, the nucleic acid is heterologous to the host cell. A particular sequence is "heterologous" to the cell or organism into which it is inserted.

"Homology" or "identity" or "similarity" refers to sequence similarity between two peptides or, more often in the context of the present disclosure, between two nucleic acid molecules. The term "homologous region" or "homology arm" refers to a region on a donor DNA with a certain degree of homology with a target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

The term "landing pad" refers to a sequence of nucleotides inserted into a genome or episome of a cell via CF editing that comprises an enzyme recognition sequence.

The term "meganuclease" refers to an endodeoxyribonuclease characterized by a large recognition site (double-stranded DNA sequences of 12 to 40 base pairs) and as a result the recognition site generally occurs only once, if at all, in any given genome.

As used herein, "nucleic acid-guided nickase/reverse transcriptase fusion" or "nickase-RT fusion" refers to a nucleic acid-guided nickase—or nucleic acid-guided nuclease or CRISPR nuclease that has been engineered to act as a nickase rather than a nuclease that initiates double-stranded DNA breaks—where the nucleic acid-guided nickase is fused to a reverse transcriptase, which is an enzyme used to generate cDNA from an RNA template, e.g., a repair template. In certain embodiments, "nucleic acid-guided nickase/reverse transcriptase fusion" or "nickase-RT fusion" refers to two or more nucleic acid-guided nickases—or nucleic acid-guided nucleases or CRISPR nucleases that have been engineered to act as nickases rather than nucleases that initiate double-stranded DNA breaks—where the nucleic acid-guided nickases are fused to a reverse transcriptase. For information regarding nickase-RT fusions see, e.g., U.S. Pat. No. 10,689,669 and U.S. Ser. No. 16/740,421.

"Nucleic acid-guided editing components," in certain embodiments, refers to one or both of a nickase-RT fusion and CREATE fusion guide nucleic acids (CFgRNAs). In certain embodiments, the term "nucleic acid-guided editing components" refers to one, some, or all of a nucleic acid-guided nuclease or nickase fusion enzyme, a guide nucleic acid or CFgRNA, and a repair template and/or donor nucleic acid.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "PAM mutation" refers to one or more edits to a target sequence that removes, mutates, or otherwise renders inactive a PAM or spacer region in the target sequence.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA.

As used herein, the terms "protein," "peptide," and "polypeptide" are used interchangeably herein and refer to a polymer of amino acid residues. Proteins may or may not be made up entirely of amino acids.

"Recognition sequences" are particular sequences of nucleotides that a protein, DNA, or RNA molecule, or combinations thereof (such as, but not limited to, a restriction endonuclease, a modification methylase or a recombinase) recognizes and binds. For example, a recognition sequence for Cre recombinase is a 34 base pair sequence containing two 13 base pair inverted repeats (serving as the recombinase binding sites) flanking an 8 base pair core and designated loxP (see, e.g., Sauer, Current Opinion in Biotechnology, 5:521-527 (1994)). Other examples of recognition sequences include, but are not limited to, attB and attP, attR and attL and others that are recognized by the recombinase enzyme bacteriophage Lambda Integrase. The recombination site designated attB is an approximately 33 base pair sequence containing two 9 base pair core-type Int binding sites and a 7 base pair overlap region; attP is an approximately 240 base pair sequence containing core-type Int binding sites and arm-type Int binding sites as well as sites for auxiliary proteins IHF, FIS, and Xis (see, e.g., Landy, Current Opinion in Biotechnology, 3:699-7071 (1993)).

A "recombinase" is an enzyme that catalyzes the exchange of DNA segments at specific recombination sites. An "integrase" refers to a recombinase that is usually derived from viruses or transposons, as well as perhaps ancient viruses and serves to insert, rather than remove or invert DNA sequences. "Recombination proteins" include excisive proteins, integrative proteins, enzymes, co-factors and associated proteins that are involved in recombination reactions using one or more recombination sites (again see, e.g., Landy, Current Opinion in Biotechnology, 3:699-707 (1993)). The recombination proteins used in the methods herein can be delivered to a cell via an editing cassette on an appropriate vector, such as a plasmid or viral vector. In other embodiments, recombination proteins can be delivered to a cell in protein form in the same reaction mixture used to deliver the desired nucleic acid(s). In yet other embodiments, the recombinase could also be encoded in the cell and expressed upon demand using a tightly controlled inducible promoter.

As used herein, the terms "repair template" or "homology arm" refer to 1) nucleic acid that is designed to facilitate introduction of a DNA sequence modification (insertion, deletion, substitution) into a locus by homologous recombination using nucleic acid-guided nucleases, or 2) a nucleic acid that serves as a template (including a desired edit) to be incorporated into target DNA by reverse transcriptase in a CREATE fusion editing (CFE) system. For homology-directed repair, a repair template or homology arm may have sufficient homology to the regions flanking the "cut site" or the site to be edited in the genomic target sequence. For template-directed repair, the repair template or homology arm has homology to the genomic target sequence except at the position of the desired edit although synonymous edits may be present in the homologous (e.g., non-edit) regions. The length of the repair template(s) or homology arm(s) will depend on, e.g., the type and size of the modification being made. In many instances and preferably, the repair template will have two regions of sequence homology (e.g., two homology arms) complementary to the genomic target locus flanking the locus of the desired edit in the genomic target locus. Typically, an "edit region" or "edit locus" or "DNA sequence modification" region—the nucleic acid modification that one desires to be introduced into a genome target locus in a cell (e.g., the desired edit)—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence, such as 10,000 or more base pairs. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence, such as 10,000 or more base pairs.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, nourseothricin N-acetyl transferase, erythromycin, tetracycline, gentamicin, bleomycin, streptomycin, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+ cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2a; detectable by Mab-FITC); Methylguanine-DNA methyltransferase (MGMT; selectable by carmustine); rhamnose; and Cytidine deaminase (CD; selectable by Ara-C). "Selective medium" as used herein refers to cell growth medium to which has been added a chemical compound or biological moiety that selects for or against selectable markers.

The term "specifically binds" as used herein includes an interaction between two molecules, e.g., an engineered peptide antigen and a binding target, with a binding affinity represented by a dissociation constant of about $10^{-7}$M, about $10^{-8}$ M, about $10^{-9}$M, about $10^{-10}$ M, about $10^{-11}$M, about $10^{-12}$M, about $10^{-13}$M, about $10^{-14}$M or about $10^{-15}$M.

The terms "target genomic DNA locus", "target locus", or "genomic target locus" refer to any locus in vitro or in vivo, or in a nucleic acid (e.g., genome or episome) of a cell or population of cells, in which a change of at least one nucleotide is desired using a nucleic acid-guided nuclease editing system. The target sequence can be a genomic locus or extrachromosomal locus.

The term "variant" may refer to a polypeptide or polynucleotide that differs from a reference polypeptide or polynucleotide but retains essential properties. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide may be a conservatively modified variant. A substituted or inserted amino acid residue may or may not be one encoded by the genetic code (e.g., a non-natural amino acid). A variant of a polypeptide may be naturally occurring, such as an allelic variant, or it may be a variant that is not known to occur naturally.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, BACs, YACs, PACs, synthetic chromosomes, and the like.

Nucleic Acid-Guided Nickase/Reverse Transcriptase Fusion Protein Genome Editing Generally The compositions and methods described herein are a "twist" on or alternative to traditional nucleic acid-guided nuclease editing (i.e., RNA-guided nuclease or CRISPR editing) used to introduce desired edits to a population of cells; that is, the compositions and methods described herein employ a nucleic acid-guided nickase/reverse transcriptase fusion enzyme ("nickase-RT fusion") as opposed to a nucleic acid-guided nuclease (i.e., a "CRISPR nuclease"). The nickase-RT fusion employed herein differs from traditional CRISPR editing in that instead of initiating double-strand breaks in the target genome and homologous recombination to effect an edit, the nickase or nickases initiate a nick in opposing strands of the target genome. The fusion of the nickase(s) to a reverse transcriptase in combination with a single CF editing cassette (comprising a CFgRNA), or complementary CF editing cassettes (each comprising a CFgRNA), eliminates the need for a donor DNA. Instead, the single CF editing cassette or complementary CF editing cassettes, cDNA reverse-transcribed from the single CF editing cassette, or genomic DNA may serve as templates for the RT portion of the fusion enzyme to add the edit to the target locus. That is, utilization of a nickase-RT fusion incorporates the edit in the target genome by copying an RNA sequence (e.g., a repair template), a cDNA sequence reverse-transcribed from an RNA sequence, or a genomic DNA sequence rather than replacing of the target locus with a donor DNA. The nickases—having the specificity of a nucleic acid-guided nuclease—engage the target locus and nick a strand of the target locus creating one or more free 3' terminal nucleotides. The reverse transcriptase utilizes the 3' terminal nucleotide of each nick and copies the repair template(s) of the single CF editing cassette or complementary CF editing cassettes, cDNA reverse-transcribed from the single CFgRNA, or genomic DNA to create a "flap" or complementary "flaps" containing the desired edit. In summary, in certain embodiments, the present methods and compositions are drawn to use the nickase-RT fusion to nick both strands of DNA in the target locus and using a single CF editing cassette, or two CF editing cassettes (one for each strand), to effect the edit on each strand via the reverse transcriptase portion of the nickase-RT fusion.

Methods described herein facilitate increased genome-wide edit rates via incorporation of complementary edits on both strands of DNA with superior efficiency and reduced error rates as compared to other editing methods, such as traditional prime editing, which may be limited by increased NHEJ rates. Further, the described methods enable creation of longer edits, as well as increased accessibility of genomic regions previously inaccessible due to the lack of available specific PAM sites in proximity to a targeted edit.

Generally, nucleic acid-guided nuclease editing begins with a nucleic acid-guided nuclease complexing with an appropriate synthetic guide nucleic acid in a cell that can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby. For some nucleic acid-guided nucleases, two separate guide nucleic acid molecules that combine to function as a guide nucleic acid are used, e.g., a CRISPR RNA (crRNA) and trans-activating CRISPR RNA (tracrRNA). For other nucleic acid-guided nucleases, the guide nucleic acid may be a single guide nucleic acid that includes both the crRNA and tracrRNA sequences.

In general, a guide nucleic acid (e.g., gRNA) complexes with a compatible nucleic acid-guided nuclease and can then hybridize with a target sequence, thereby directing the nuclease to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA may be encoded by a DNA sequence on a polynucleotide molecule such as a plasmid, linear construct, or the coding sequence may and preferably does reside within an editing cassette, e.g., a CF editing cassette. Methods and compositions for designing and synthesizing editing cassettes and libraries of editing cassettes are described in U.S. Pat. Nos. 10,240,167; 10,266,849; 9,982,278; 10,351,877; 10,364,442; 10,435,715; 10,465,207; 10,669,559; 10,711,284; 10,731,180; and 11,078,498; all of which are incorporated by reference herein. In the present methods and compositions, the guide nucleic acid is RNA.

A guide nucleic acid comprises a guide sequence, where the guide sequence (as opposed to the scaffold sequence portion of the guide nucleic acid) is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably, the guide sequence is 10-30 or 15-20 nucleotides long, or 15, 16, 17, 18, 19, or 20 nucleotides in length.

In some embodiments of the present methods and compositions, the guide nucleic acids are provided as sequences to be expressed from a plasmid or vector and comprise both the guide sequence and the scaffold sequence as a single transcript. The guide nucleic acids are engineered to target a desired target sequence by altering the guide sequence so that the guide sequence is complementary to a desired target sequence, thereby allowing hybridization between the guide sequence and the target sequence. In general, to generate an edit in the target sequence, a gRNA/nuclease complex binds to a target sequence as determined by the guide RNA, and the nuclease recognizes a protospacer adjacent motif (PAM) sequence adjacent to the target sequence. The target sequence can be any polynucleotide endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) or a non-coding sequence (e.g., a regulatory polynucleotide, an intron, a PAM, or "junk" DNA).

Traditionally, the guide nucleic acid may be and preferably is part of an editing cassette that encodes a donor nucleic acid that targets a cellular target sequence; however, in the present methods and compositions the editing cassette—here, a CF editing cassette—does not comprise a donor nucleic acid because the reverse transcriptase portion of the nucleic acid-guided nickase/reverse transcriptase fusion enzyme (nickase-RT fusion) uses the repair template covalently linked to the CFgRNA, cDNA reverse-transcribed from the repair template, or genomic DNA, as a template to incorporate the edit into the target locus rather than depending on HDR between the target genome and the donor nucleic acid.

The target sequence is associated with a proto-spacer mutation (PAM), which is a short nucleotide sequence recognized by the gRNA/nuclease complex. The precise preferred PAM sequence and length requirements for different nucleic acid-guided nucleases vary; however, PAMs typically are 2-8 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve target site recognition fidelity, decrease target site recognition fidelity, or increase the versatility of a nucleic acid-guided nuclease.

In certain embodiments, the editing of a cellular target sequence both introduces a desired DNA change to the cellular target sequence, e.g., the genomic DNA of a cell, and removes, mutates, or renders inactive a proto-spacer adjacent motif (PAM) region or spacer region in the cellular target sequence. Rendering the PAM at the cellular target sequence inactive precludes additional editing of the cell genome at that cellular target sequence, e.g., upon subsequent exposure to a nucleic acid-guided nuclease complexed with a synthetic guide nucleic acid in later rounds of editing.

The range of target sequences that nucleic acid-guided nucleases can recognize is constrained by the need for a specific PAM to be located near the desired target sequence. As a result, it often can be difficult to target edits with the precision that is necessary for genome editing. It has been found that nucleases can recognize some PAMs very well (e.g., canonical PAMs), and other PAMs less well or poorly (e.g., non-canonical PAMs).

As for the nuclease or nickase-RT fusion component of the nucleic acid-guided nuclease editing system, a polynucleotide sequence encoding the nucleic acid-guided nuclease or nickase-RT fusion can be codon optimized for expression in particular cell types, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of nucleic acid-guided nuclease or nickase-RT fusion to be employed depends on many factors, such as what type of edit is to be made in the target sequence and whether an appropriate PAM is located close to the desired target sequence. Nucleases of use in the methods described herein include but are not limited to nickases engineered from nucleic acid-guided nucleases such as Cas9, Cas12/CpfI, MAD2, MAD2007, MAD2017, MAD2019, MAD297, MAD298, MAD299, or MAD7, or other MADzymes and nuclease or nickase fusions thereof. Nickase-RT fusion enzymes typically comprise one or more CRISPR nucleic acid-guided nucleases, each engineered to nick one DNA strand in the target DNA rather than making a double-stranded cut, and the nickase portions are fused to a reverse transcriptase. In certain embodiments of the present methods, the nickase-RT fusion nicks both strands of the target locus, albeit where the two nicks are staggered rather than at the same position which would result in a double-stranded cut. As with the guide nucleic acid, the nucleases or nickases may be encoded by one or more DNA sequences on a vector (e.g., an engine vector or an engine+editing combination vector) and be under the control of a promoter—including inducible promoters—or the nickase-RT fusion may be delivered as a protein or RNA-protein complex.

In addition to a CFgRNA, a CF editing cassette may comprise and preferably does comprise one or more primer sites. The primer sites can be used to amplify the CF editing cassette by using oligonucleotide primers; for example, if the primer sites flank one or more of the other components of the CF editing cassette.

In addition, the CF editing cassette may comprise a barcode. A barcode is a unique DNA sequence that corresponds to the donor DNA sequence such that the barcode can identify the edit made to the corresponding cellular target sequence. The barcode typically comprises four or more nucleotides. In some embodiments, the CF editing cassettes comprise a collection or library of CFgRNAs or complementary CFgRNA pairs representing, e.g., gene-wide or genome-wide libraries of the CFgRNAs or CFgRNA pairs. The library of CF editing cassettes is cloned into vector backbones where, e.g., each different donor nucleic acid is associated with a different barcode.

Additionally, in some embodiments, an expression vector encoding the nickase-RT fusion enzyme or the CF editing cassette further encodes one or more nuclear localization sequences (NLSs), such as about or more than about 1, 2, 3, 4, 5, 6, 7, 8, 9, 10, or more NLSs. In some embodiments, the engineered nuclease comprises NLSs at or near the amino-terminus, NLSs at or near the carboxy-terminus, or a combination.

In certain embodiments, the CF editing cassette(s) further comprise a "landing pad" sequence, or a sequence of nucleotides comprising an enzyme recognition sequence, such as a recombinase, integrase, nuclease, or meganuclease recognition sequence. The landing pad can be leveraged to insert additional donor nucleic acid sequences, including additional plasmids, in initial, subsequent and recursive editing operations.

Improved Nucleic Acid-Guided Nickase/Reverse Transcriptase Fusion Editing Using Dual CF Editing Cassettes The present disclosure provides compositions of matter, methods and instruments for nucleic acid-guided nickase/reverse transcriptase fusion ("nickase-RT fusion") editing of live cells using two complementary CF editing cassettes, each comprising a CREATE fusion guide RNA, that are engineered to edit opposite DNA strands at a target locus. With the present compositions and methods, editing efficiency is improved by using fusion proteins (i.e., the nickase-RT fusion enzymes) that retain certain characteristics of nucleic acid-directed nucleases—the binding specificity and ability to cleave one or more DNA strands in a targeted manner—combined with another enzymatic activity such as reverse transcriptase activity, which allows an edit to be incorporated into the target locus by reverse transcription of a portion of the CF editing cassette (e.g., the repair template). The nickase-RT fusion enzyme may be introduced into the cells using a DNA molecule coding for the nickase-RT fusion enzyme separately or covalently-linked to the two CF editing cassettes or the nickase-RT fusion enzyme may be introduced separately in protein form or as part of a complex.

The nickase-RT fusion employed herein differs from traditional CRISPR editing in that instead of initiating double-strand breaks in the target genome and homologous recombination to effect an edit, the nickase initiates a nick in opposing strands of the target genome. The fusion of the nickase to a reverse transcriptase in combination with complementary CF editing cassettes eliminates the need for a donor DNA; instead, the repair templates of the CF editing cassettes serve as templates for the RT portion of the fusion enzyme to add the edit to the target locus. That is, utilization of a nickase-RT fusion incorporates the edit in the target genome by copying an RNA sequence (i.e., a portion of the CF editing cassette sequences) rather than replacing of the target locus with a donor DNA. The nickase—having the specificity of a nucleic acid-guided nuclease—engages the target locus, nicks a strand of the target locus creating a 3' terminal nucleotide. The reverse transcriptase utilizes the 3' terminal nucleotide and a repair template of a CF editing cassette to create a "flap" containing the desired edit.

FIG. 1A is a simplified block diagram of an exemplary method 100a for editing live cells via nucleic acid-guided nickase/reverse transcriptase fusion ("nickase-RT fusion") editing. Looking at FIG. 1A, method 100a begins by designing and synthesizing complementary CF editing cassettes designed to incorporate an edit into opposite DNA strands at a target locus. That is, each CF editing cassette comprises two complementary sequences to be reverse transcribed comprising desired complementary target genome edits as well as a PAM and/or spacer mutation(s). Once the CF editing cassettes have been synthesized, the individual CF editing cassettes are amplified and complementary pairs of CF editing cassettes are inserted into a vector backbone, such as a lentiviral backbone, to create editing vectors 104. In addition, a nucleic acid-guided nickase/reverse transcriptase fusion protein ("nickase-RT fusion") enzyme is designed 106. The nickase-RT fusion enzyme may be delivered to the cells as a coding sequence in a vector backbone (in some embodiments under the control of an inducible promoter) or the nickase-RT fusion enzyme may be delivered to the cells as a protein or protein complex. In method 100a, the nickase-RT fusion enzyme is delivered to the cells via a coding sequence in an engine vector 108. At step 110, the engine and editing vectors are introduced into the live cells.

A variety of delivery systems may be used to introduce (e.g., transform, transfect, or transduce) nucleic acid-guided nickase fusion editing system components into a host cell 110. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., U.S. Pat. No. 10,253,316, issued 9 Apr. 2019; U.S. Pat. No. 10,329,559, issued 25 Jun. 2019; U.S. Pat. No. 10,323,242, issued 18 Jun. 2019; U.S. Pat. No. 10,421,959, issued 24 Sep. 2019; U.S. Pat. No. 10,465,185, issued 5 Nov. 2019; U.S. Pat. No. 10,519,437, issued 31 Dec. 2019; U.S. Pat. No. 10,584,333, issued 10 Mar. 2020; U.S. Pat. No. 10,584,334, issued 10 Mar. 2020; U.S. Pat. No. 10,647,982, issued 12 May 2020; U.S. Pat. No. 10,689,645, issued 23 Jun. 2020; U.S. Pat. No. 10,738,301, issued 11 Aug. 2020; U.S. Pat. No. 10,738,663, issued 29 Sep. 2020; and U.S. Pat. No. 10,894,958, issued 19 Jan. 2021 all of which are herein incorporated by reference in their entirety.

Once transformed 110, the next step in method 100a is to provide conditions for nucleic acid-guided nuclease editing 112. "Providing conditions" includes incubation of the cells in appropriate medium and may also include providing conditions to induce transcription of an inducible promoter (e.g., adding antibiotics, adding inducers, increasing temperature) for transcription of both of the CF editing cassettes (e.g., CFgRNA and repair template pairs) and/or the nickase-RT fusion. Once editing is complete, the cells are allowed to recover and are preferably enriched for cells that have edited 114. Enrichment can be performed directly, such as via cells from the population that express a selectable marker, or by using surrogates, e.g., cell surface handles co-introduced with one or more components of the editing components. At this point in method 100a, the cells can be characterized phenotypically or genotypically or optionally steps 110-114 may be repeated to make additional edits 116. As described above, the nickase-RT fusion enzyme may be delivered to the cells as a coding sequence in a vector backbone or the nickase-RT fusion enzyme may be delivered to the cells as a protein or as a protein-RNA complex. The coding sequence for the nickase-RT fusion enzyme may be in a combined engine+editing vector or on a separate vector. In some embodiments, the CF editing cassettes are delivered to the cells via a viral vector where the CFgRNAs and/or repair templates are integrated into the cellular genome. Subsequently, the nickase-RT fusion enzyme is delivered to the cells as a protein.

Figure 1B:
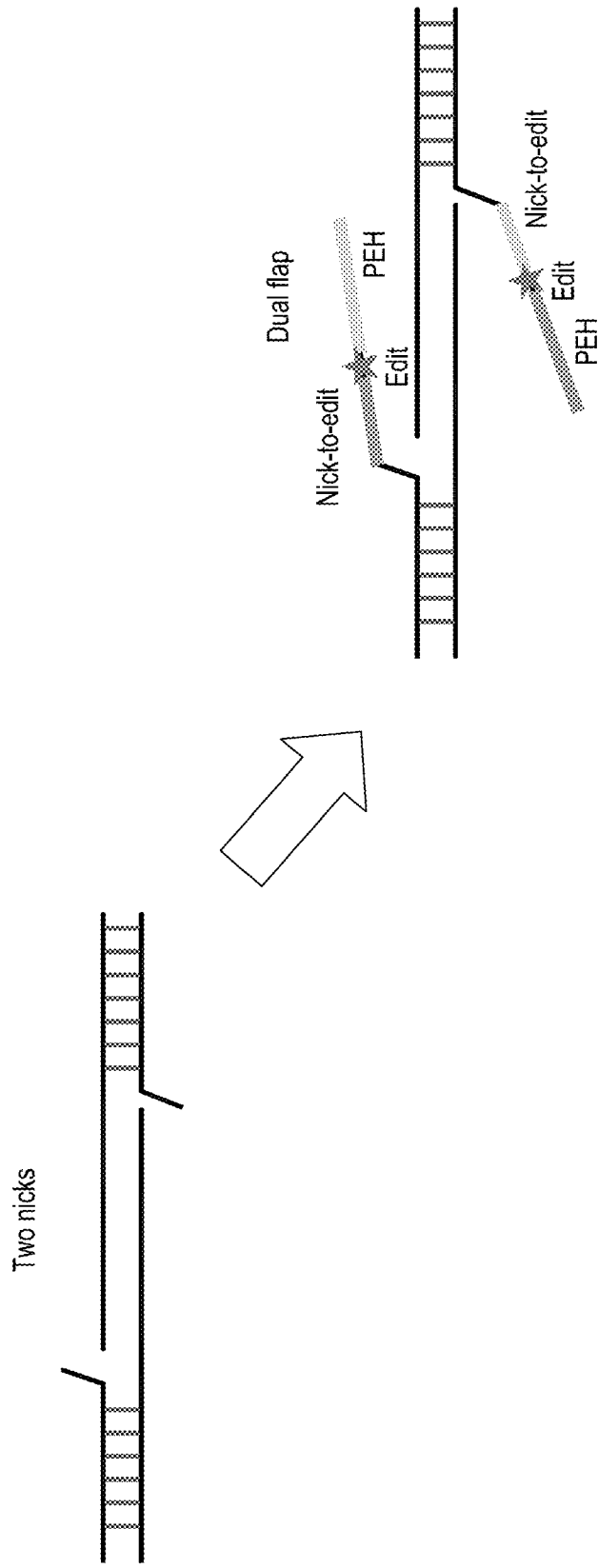
FIG. 1B is a simplified graphic depiction of the mechanism of a dual CF editing cassette nucleic acid-guided nickase/reverse transcriptase fusion enzyme edit.

FIG. 1B a simplified graphic depiction of the mechanism of a dual CF editing cassette nucleic acid-guided nickase enzyme/reverse transcriptase fusion enzyme edit. At left in FIG. 1B shows a target locus, where a target locus in the context of the methods and compositions herein is a locus of approximately 8 to 500 nucleotides in length, or 10 to 400 nucleotides in length, or 10 to 300 nucleotides in length. Note that both DNA strands of the target locus are nicked, but that the nicks are staggered. In order for the nickase-RT fusion enzyme and the first CF editing cassette to bind to the first strand and the nickase-RT fusion enzyme and the second CF editing cassette to bind to the second strand, there must be a protospacer adjacent motif (PAM) appropriately located on both the first and second strand. The first CF editing cassette must be complementary to a region of the first strand and the second CF editing cassette must be complementary to a region of the second strand. The first and second CF editing cassettes must be designed to edit opposite DNA strands in the target locus and must include the same desired edit, albeit where the sequence of the desired edit on the first and second CF editing cassette would be complementary to one another (see FIG. 1D and the description thereof).

At right in FIG. 1B shows the nick-to-edit for each flap, where the reverse transcriptase (RT) portion of the nickase-RT fusion enzyme has added nucleotides to the 3' end of each nicked strand using the repair template of the first CF editing cassette as a template for the first (here, top) strand and the repair template of the second CF editing cassette as a template for the second (here, bottom) stand. The regions of the DNA strands that are synthesized by the RT includes a nick-to-edit region, an edit region, and a post-edit homology (PEH) region. Because the first and second CF editing cassettes are complementary in part, the nick-to-edit region, the edit region and the post-edit homology (PEH) regions, respectively, of the first strand added by the reverse transcriptase are complementary to the post-edit homology (PEH), the edit region and the nick-to-edit region, respectively, of the second strand. Note that the edit is incorporated on both strands of the target locus.

Although described in reference to dual CF editing cassette nickase-RT fusion editing, the mechanisms depicted in FIG. 1B further apply to nickase-RT fusion editing utilizing only a single CF editing cassette and/or a single nickase-RT fusion enzyme (described below).

FIG. 1C is a simplified depiction of dual CF editing cassette nickase-RT fusion editing showing the target locus, nickase-RT, the CF editing cassettes and two different annealing products prior to flap removal/edit incorporation. At left in FIG. 1C is a target locus with a "first target" and a "second target." Note that the first target and the second target are both part of the target locus and the target locus is not a single nucleotide but is a region of approximately 10 to 300 nucleotides as described supra. In this depiction, the first target is located on the top strand of the target locus and the second target is located on the bottom strand of the target locus. As described in relation to FIG. 1B above, in order for the nickase-RT and CF editing cassette to bind to the target locus and to edit at the first target and the second target, an appropriate PAM must be located on both the first target and the second target in the target locus.

In one step, the nickase-RT and first CF editing cassette bind to the target locus and the nickase nicks the first strand creating a 3' end (see, e.g., FIG. 1B). The RT component of the nickase-RT fusion uses the first CF editing cassette as a template to add nucleotides to the 3' end of the top DNA strand including the desired edit, making a "flap." In another step, which may be concurrent or sequential with the first step, the nickase-RT and second CF editing cassette bind to the target locus and the nickase nicks the second stand also creating a 3' free end. The RT component of the nickase-RT fusion uses the second CF editing cassette as a template to add nucleotides to the 3' end of the bottom DNA strand including the desired edit, where, as described in relation to FIG. 1B, the nucleotides added to the top and bottom DNA strands are complementary to one another. After addition of the nucleotides to the 3' ends of both DNA strands, the target locus resolves into either wildtype (WT), where the desired edit is not incorporated, or into an edited target locus.

In traditional CREATE-fusion editing, once a single DNA flap containing the edit is synthesized, an equilibrium is established between annealing of the newly synthesized 3' flap and the wild-type 5' flap to the unedited strand of genomic DNA (not shown). The equilibrium can be affected by the length of the edit, nick-to-edit distance, and/or post-edit homology region. In order for the newly synthesized flap to be incorporated into the genome, the WT 5' flap is likely degraded by an exonuclease. The 3' flap, containing the edit, anneals to the DNA, and then a polymerase likely fills in any missing nucleotides and a DNA ligase seals the nick. Additionally, in conventional CREATE-fusion editing, only one DNA strand contains the edit while the second DNA strand does not. Mismatch repair or DNA replication is likely responsible for incorporating the edit into both strands. Note that while annealing of the WT flap, DNA replication and mismatch repair can also favor the WT sequence as opposed to the edited sequence. If the flap equilibration favors the WT 5' flap, the newly synthesized flap is likely degraded and sealed in the same manner described above, resulting in a WT, unedited genome. In contrast, incorporation of two complementary flaps pushes the equilibrium away from annealing of the WT flap and toward annealing of the two, complementary, newly-synthesized edits. Further, the newly-synthesized edits may not rely on endogenous mismatch repair mechanisms nor creation of an additional strand containing the edit.

Figure 1D:
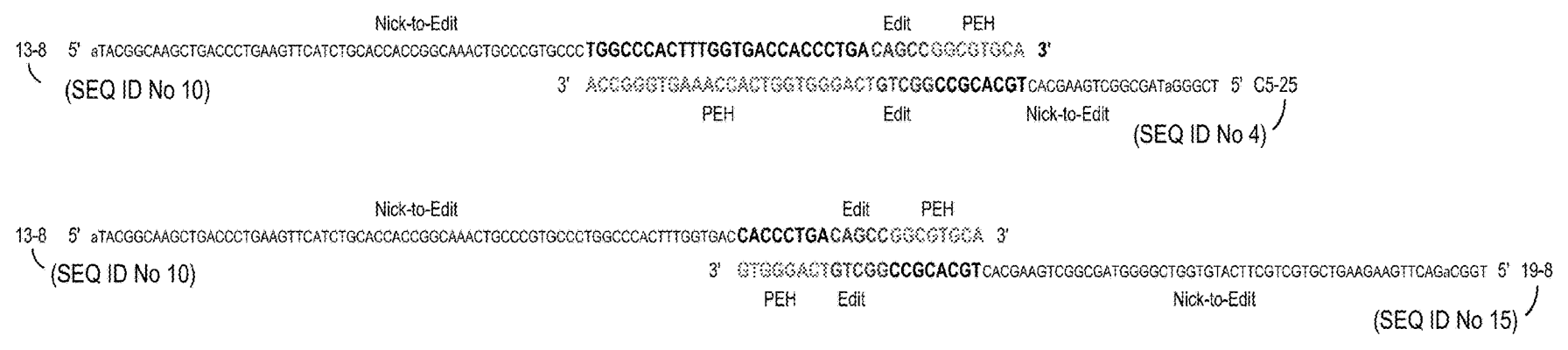
Figure 7:
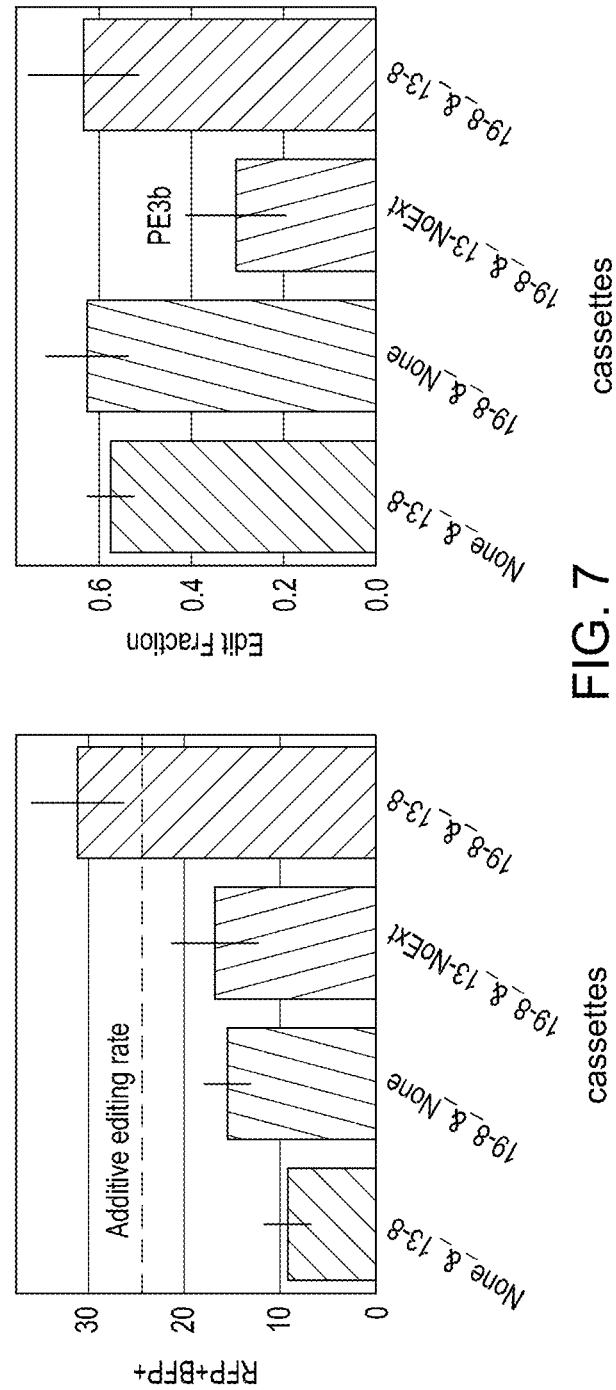
FIG. 7 comprises two a bar graphs where the first bar graph demonstrates that the editing rate is increased when utilizing a nickase-RT fusion enzyme and both a 19-8 CF editing cassette ("CFg") and a 13-8 CF editing cassette ("CFg"). The second bar graph demonstrates that the edit fraction obtained with a nickase-RT fusion enzyme and either or both a 19-8 CF editing cassette ("CFg") and a 13-8 CF editing cassette ("CFg") is greater than the edit fraction obtained with prime editing or prime editing with an additional nick (PE3b). Edit fraction is defined as the fraction of the desired edit over all observed edits or HR/(NHEJ+HR). HR is measured by observing measuring the change in fluorescence (GFP>BFP) for transfected cells. NHEJ is measured by measuring a loss in GFP fluorescence for transfected cells.
Figure 8:
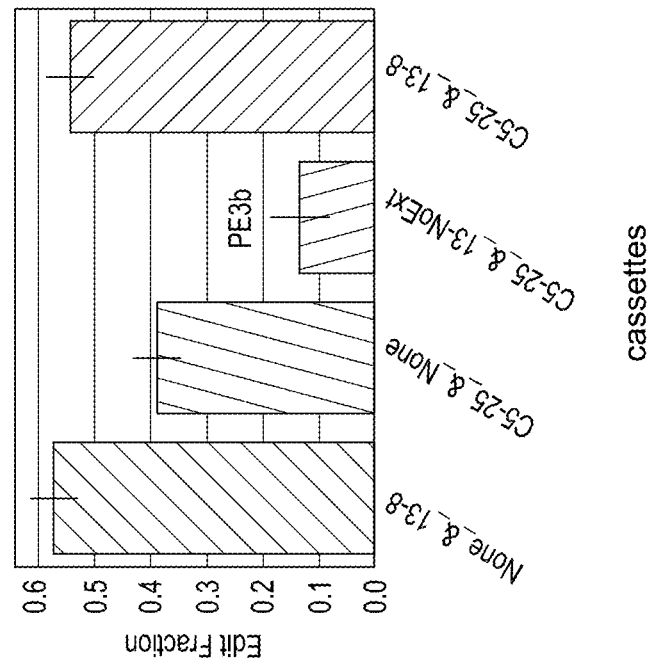
FIG. 8 comprises two a bar graphs where the first bar graph demonstrates that the editing rate is increased when utilizing a nickase-RT fusion enzyme and both a C5-25 CF editing cassette and a 13-8 CF editing cassette. The second bar graph demonstrates that the edit fraction obtained with a nickase-RT fusion enzyme and either or both a C5-25 CF editing cassette and a 13-8 CF editing cassette is greater than the edit fraction obtained with prime editing or prime editing with an additional nick (PE3b). Edit fraction is defined as the fraction of the desired edit over all observed edits or HR/(NHEJ+HR). HR is measured by observing measuring the change in fluorescence (GFP>BFP) for transfected cells. NHEJ is measured by measuring a loss in GFP fluorescence for transfected cells.
Figure 8:
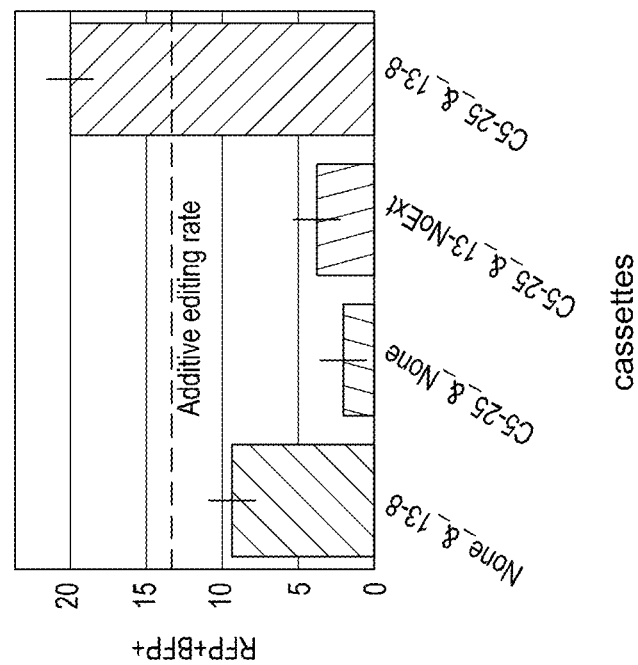

FIG. 1D at top is a table giving the spacer, scaffold, post-edit homology, edit, nick-to-edit, and primer binding sequences of three exemplary complementary CF editing cassettes used in experiments described in FIGS. 7-8, and additionally FIG. 1D at bottom shows how the sequences from complementary CF editing cassettes (i.e., CF 13-8 and C5-25 as well we 13-8 and 19-8) relate to one another. In the two matched complementary CF editing cassettes at bottom, the regions that anneal are depicted in bold black font, the post-edit homology regions are depicted in bold red font, the edit regions are depicted in bold purple font, the nick-to-edit regions are depicted in black regular font, and synonymous mutations, i.e., immunizing mutations to prevent re-nicking are depicted in lower case in the nick-to-edit regions. The 3' extension on each CF editing cassette (e.g., the repair template) provides a template for the reverse transcriptase to synthesize the complementary DNA sequence. Typically, the length of the regions that anneal are from 4 to 120 nucleotides in length, or from 5 to 80 nucleotides in length, or from 6 to 60 nucleotides in length. The length of the regions of post-edit homology are from 2 to 50 nucleotides in length, or from 4 to 40 nucleotides in length, or from 5 to 25 nucleotides in length. The length of the edit region is from 1 to 750 nucleotides in length, or from 1 to 500 nucleotides in length, or from 1 to 250 nucleotides in length. The length of the nick-to-edit regions are from 0 to 250 nucleotides in length, or from 5 to 150 nucleotides in length, or from 0 to 150 nucleotides in length.

Figure 1E:
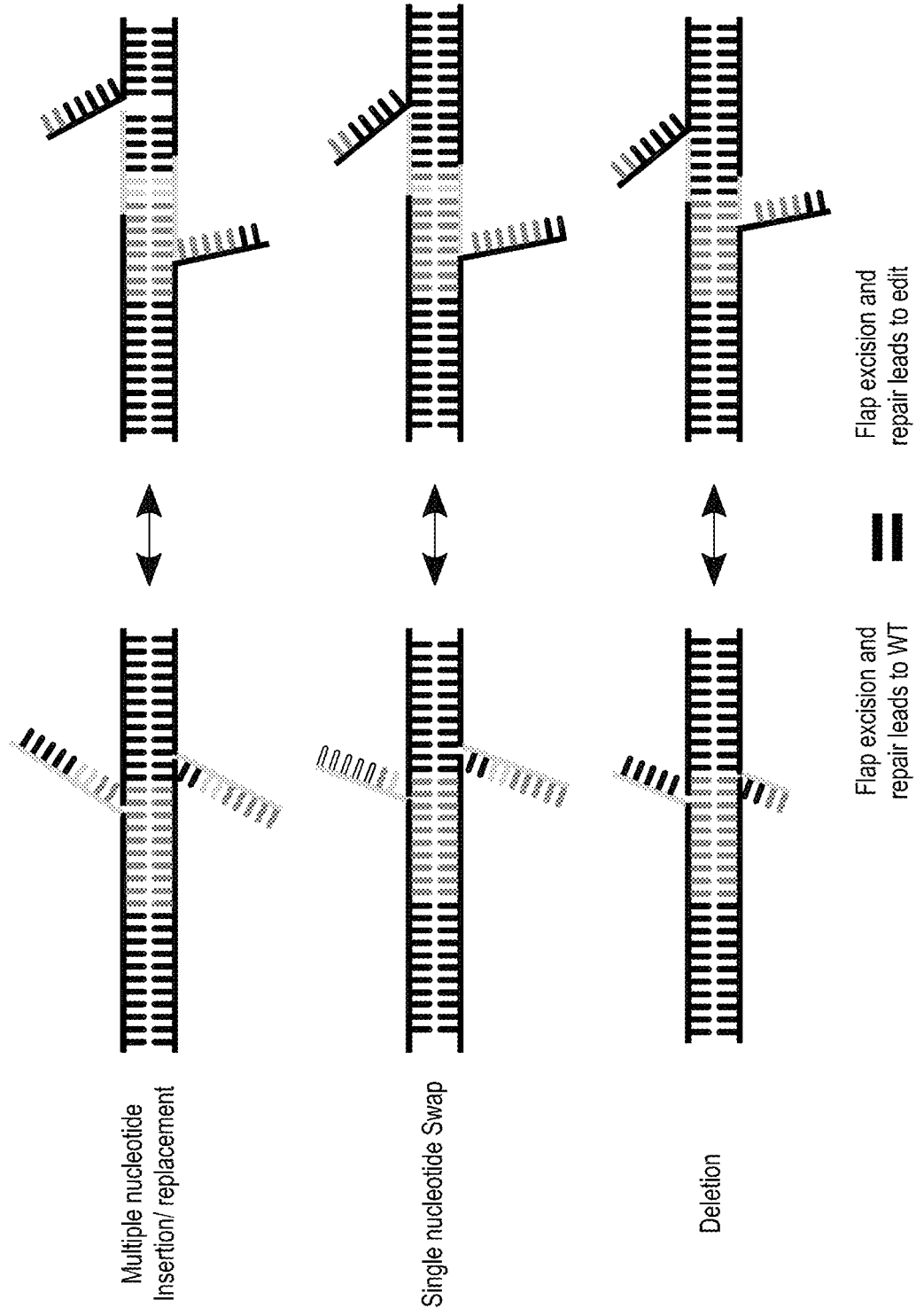
FIG. 1E is a simplified graphic depiction of the mechanism of a dual CF editing cassette nucleic acid-guided nickase/reverse transcriptase fusion protein editing to effect a multiple nucleotide insert, a single nucleotide swap and a deletion.

FIG. 1E is a simplified graphic depiction of the mechanism of a dual CF editing cassette nucleic acid-guided nickase/reverse transcriptase fusion protein editing to effect a multiple nucleotide insert, a single nucleotide swap and a deletion.

Improved Nucleic Acid-Guided Nickase/Reverse Transcriptase Fusion Editing Using a Nickase-RT Fusion Enzyme and a Single CF Editing Cassette The present disclosure further provides compositions of matter, methods, and instruments for nickase-RT fusion editing of live cells using a single nickase-RT fusion enzyme and a single CF editing cassette encoding a single "flap" of a desired edit to facilitate editing of opposite DNA strands at a target locus, as opposed to utilizing two fusion enzymes and dual complementary CF editing cassettes. Such embodiments take advantage of the ability of many RTs, such as Murine Leukemia Virus (MLV) RT, to template from cDNA as well as RNA. Accordingly, a single CF editing cassette may serve as a template for the RT portion of a single fusion enzyme to add an edit to a target locus of a target genome, thereby reducing the number of components necessary to perform nickase-RT fusion editing. That is, utilization of a nickase-RT fusion protein with an RNA- and cDNA-templating RT may incorporate the edit in the target genome by first copying, e.g., reverse-transcribing into cDNA, the single CF editing cassette for a first strand, and then utilizing the newly reverse-transcribed cDNA as a template for the second strand. In such embodiments, in order to create nicks on opposing strands of the target genome at the target locus, an additional, e.g., second, nickase is utilized, which may or may not be a component of the nickase-RT fusion protein, and thus, fused therewith, e.g., nickase-RT-nickase. Because such embodiments require fewer components to assemble at a target locus to create desired edits, more efficient creation of the two flaps for nickase-RT fusion editing may be enabled.

Figure 1F:
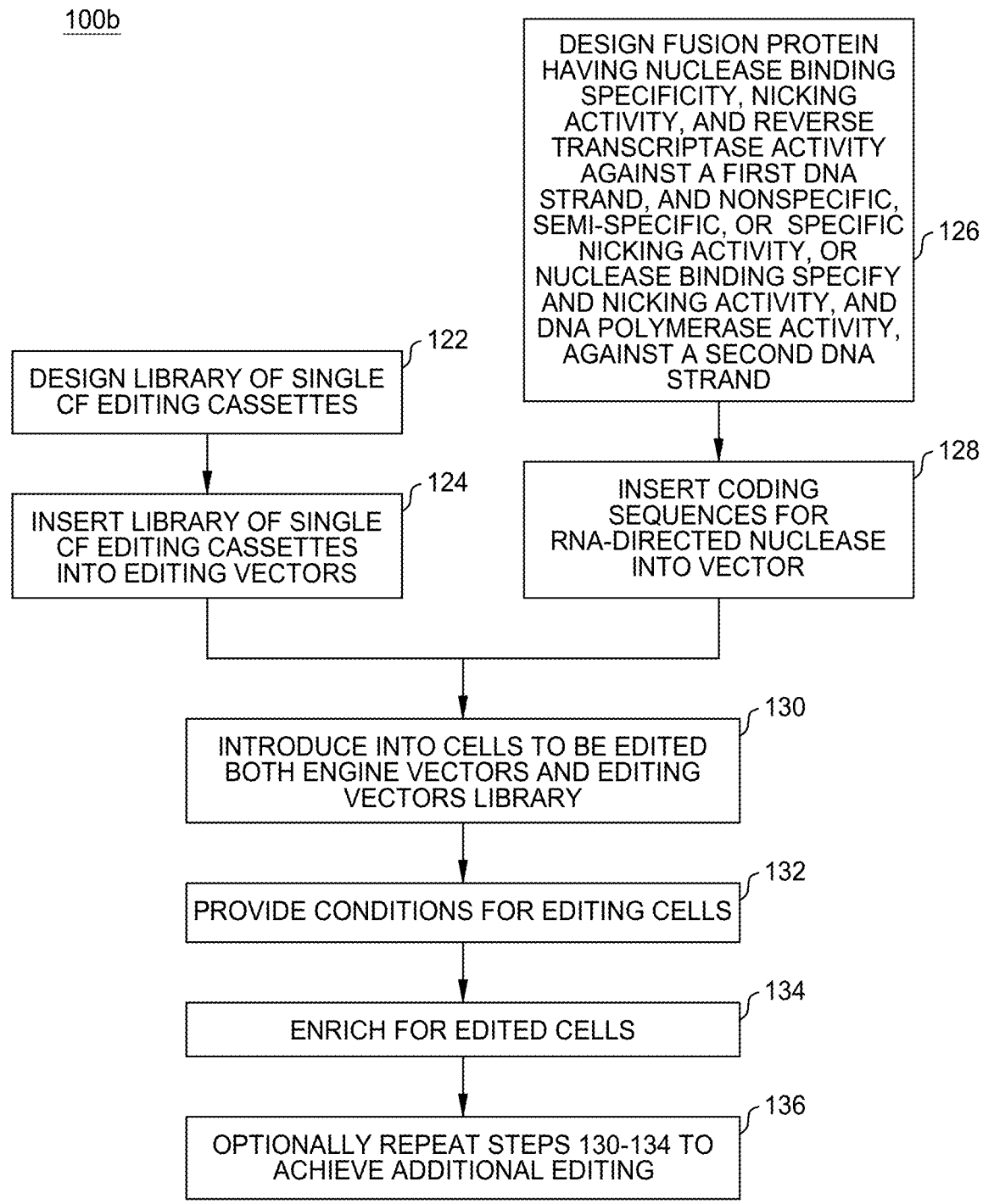
FIG. 1F is a simplified block diagram of an exemplary method for nickase-RT fusion editing of live cells utilizing a nickase-RT fusion enzyme and a single CF editing cassette.

FIG. 1F is a simplified block diagram of an exemplary method 100b for editing live cells via nickase-RT fusion editing utilizing a single nickase-RT fusion enzyme and a single CF editing cassette. The method 100b is substantially similar to the method 100a described above. Looking at FIG. 1F, method 100b begins by designing and synthesizing CF editing cassettes 122 designed to facilitate incorporation of an edit into a DNA strand at a target locus. That is, each CF editing cassette comprises a CFgRNA sequence covalently linked to a repair template sequence, wherein the repair template comprises one or more desired target genome edits as well as a PAM or spacer mutation. The CF editing cassette, like a gRNA in typical CRISPR editing, may be partially complementary to a region of either the first or second strand of genomic DNA. Once the CF editing cassettes have been synthesized, the individual CF editing cassettes are amplified and inserted into a vector backbone, such as a lentiviral backbone, to create editing vectors 124.

In addition, a nickase-RT fusion enzyme is designed 126 to have nuclease binding specificity, nicking activity, and reverse transcriptase activity against one strand of the genomic DNA, and nonspecific, semi-specific, or specific nicking activity, or nuclease binding specify and nicking activity, and DNA polymerase activity, against a second strand of the genomic DNA. In certain embodiments, the nickase-RT fusion enzyme includes a first nickase and a second, exogenous nickase fused to an RT component (e.g., nickase-RT-nickase), wherein the first nickase is a nickase that recognizes a specific sequence of DNA and the second nickase is a promiscuous nickase (that nicks related sequences) or a nonspecific nickase (that nicks all sequences), or vice versa. In certain embodiments, the second nickase may also be semi-specific, specific, or nucleic acid-guided. Utilization of a promiscuous or non-specific second nickase reduces the requirements for the two PAM sites needed for two CRISPR-DNA-type recognition events, thus enabling more efficient creation of the two flaps for nickase-RT fusion editing and increasing the range of target sites accessible by the dual flap strategy. Generally, the first and second nickases may be fused to the RT component in any arrangement. For example, the RT component may be located at the C terminus of the nickase-RT fusion, the N terminus of the nickase-RT fusion, or the RT component may be fused between the first and second nickases (shown in FIG. 1G). In certain other embodiments, the nickase-RT fusion protein includes only the first nickase, and the second nickase is an isolated nickase separately recruited during editing.

The nickase-RT fusion enzyme may be delivered to the cells as a coding sequence in a vector backbone (in some embodiments under the control of an inducible promoter) or the nickase-RT fusion enzyme may be delivered to the cells as a protein or protein complex. The coding sequence for the nickase-RT fusion enzyme may be in a combined engine+editing vector or on a separate vector. In some embodiments, the CF editing cassette is delivered to the cells via a viral vector where the CF editing cassette is integrated into the cellular genome. Subsequently, the nickase-RT fusion enzyme is delivered to the cells as a protein.

In embodiments where the second nickase is an isolated nickase, the second nickase is delivered to the cells as a separate coding sequence in the vector backbone, or as a separate protein or protein complex. In method 100b, the nickase-RT fusion enzyme includes both the first and second nickase fused to an RT, and is delivered to the cells via a coding sequence in an engine vector 128. At step 130, the engine and editing vectors are introduced into the live cells.

As described with reference to method 100a, a variety of delivery systems may be used to introduce (e.g., transform, transfect, or transduce) nucleic acid-guided nickase fusion editing system components into a host cell 130. These delivery systems include the use of yeast systems, lipofection systems, microinjection systems, biolistic systems, virosomes, liposomes, immunoliposomes, polycations, lipid: nucleic acid conjugates, virions, artificial virions, viral vectors, electroporation, cell permeable peptides, nanoparticles, nanowires, exosomes, molecular troj an horse liposomes, and electroporation systems. Once transformed 130, the next step in method 100b is to provide conditions for nucleic acid-guided nuclease editing 132. As described above, "providing conditions" includes incubation of the cells in appropriate medium and may also include providing conditions to induce transcription of an inducible promoter (e.g., adding antibiotics, adding chemical inducers, or increasing temperature) for transcription of the CF editing cassette and/or the nickase-RT fusion. Once editing is complete, the cells are allowed to recover and are preferably enriched for cells that have edited 134. At this point in method 100b, the cells can be characterized phenotypically or genotypically or optionally steps 130-134 may be repeated to make additional edits 136.

FIG. 1G is a simplified depiction of nickase-RT fusion editing utilizing a single nickase-RT fusion enzyme and a single CF editing cassette. FIG. 1G depicts the nickase-RT, which has a first nickase and second, additional nickase, the CF editing cassette, and the mechanism of repair. The target locus is generally a region of approximately 10 to 300 nucleotides as described supra. As described in relation to FIGS. 1B-1C above, in order for the nickase-RT fusion enzyme and CF editing cassette to bind to the target locus and to edit at the target locus, an appropriate PAM must be located in or adjacent to the target locus. In one step, the nickase-RT and CFgRNA of the CF editing cassette bind to the target locus and the first nickase, e.g., a Cas9 nickase, nicks the first (top) strand creating a first flap having a 3' end. The RT component of the single nickase-RT fusion uses the repair template of the CF editing cassette as a template to add nucleotides to the 3' end of the top DNA strand including the desired edit, resulting in a complementary DNA (cDNA) strand. The region of the top DNA strand that is synthesized by the RT component includes a nick-to-edit region, an edit region, and a post-edit homology (PEH) region.

In another step, the second nickase, which may be fused to the nickase-RT as shown in FIG. 1G or a separate protein or protein complex, nicks the second (bottom) strand and creates a second free 3' end. As described above, in certain embodiments, the second nickase may be a nickase that recognizes a specific sequence of DNA, a promiscuous nickase that nicks related sequences, or a nonspecific nickase that nicks all sequences. For example, in certain embodiments, the second nickase may naturally lack or be engineered to lack a DNA binding domain (such as FokI), and may depend on the first nickase for localization to the DNA, thus constraining the second nicking event to the target site. Upon forming the second nick, the RT component of the nickase-RT fusion uses as a template either the previously-synthesized cDNA strand, or the first (top) genomic DNA strand for adding nucleotides to the 3' end of the bottom DNA strand. When the previously-synthesized cDNA strand is utilized as a template for the bottom strand (similar to a behavior found in most native non-long terminal repeat (non-LTR) retrotransposons and known as "template switching"), the region of the bottom DNA strand that is synthesized by the RT component includes a PEH region, an edit region, and a nick-to-edit region that are complementary to the nick-to-edit region, edit region, and PEH region, respectively, of the top strand. In such embodiments, the edit is incorporated on both strands of the target locus, and the target locus may resolve into an edited target locus with productive edits. When the first genomic DNA strand is utilized as a template for the second strand, however, the desired edit is not incorporated into the second strand, and the second strand may resolve with the first genomic strand to reform a target locus with unproductive edits (i.e., without the desired edit, but comprising a new region of cDNA).

Improved Nucleic Acid-Guided Nickase/Reverse Transcriptase Fusion Editing using a Nickase-RT Fusion Enzyme Having Two Cas Orthologues Fused in Series Embodiments of the present disclosure also provide compositions of matter, methods, and instruments for nickase-RT fusion editing of live cells using a nickase-RT fusion enzyme comprising orthogonal Cas nickase orthologues (e.g., variants) fused in series with an RT component. Such embodiments take advantage of the ability of different Cas variants, when fused together, to remain functional. Because such embodiments require only a single nickase-RT fusion enzyme to assemble at a target locus and create desired edits, more efficient creation of the two flaps for nickase-RT fusion editing may be enabled. Additionally, a single binding event of one of the fused Cas variants to their respective target may greatly reduce the PAM-binding requirements of the second Cas variant, thus increasing the range of genomic target sites accessible by nickase-RT fusion editing.

Figure 1H:
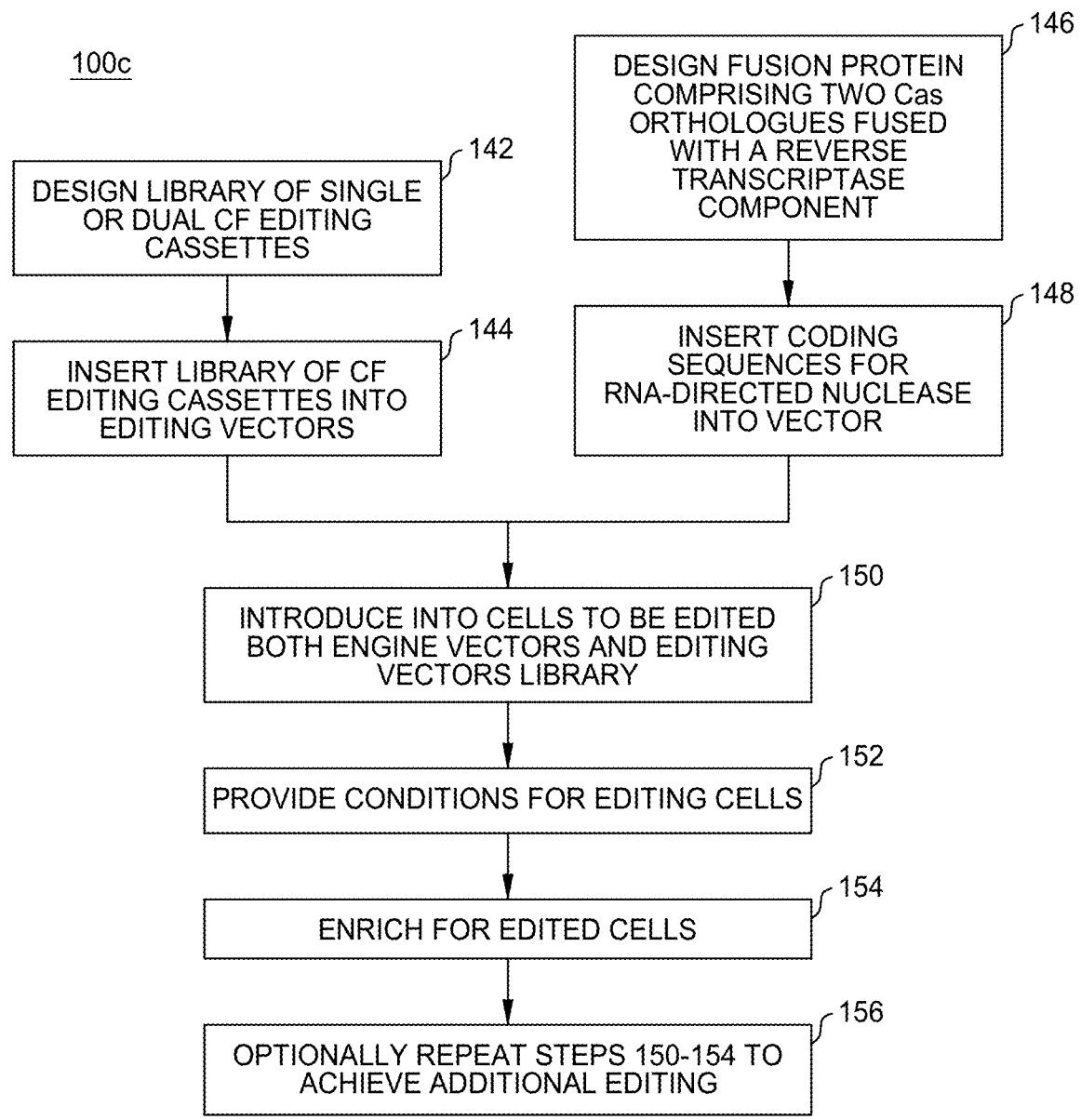
FIG. 1H is a simplified block diagram of an exemplary method for nickase-RT fusion editing of live cells utilizing a nickase-RT fusion enzyme comprising two Cas orthologues fused in series.

FIG. 1H is a simplified block diagram of an exemplary method 100c for editing live cells via nickase-RT fusion editing utilizing a nickase-RT fusion enzyme having two Cas variants fused in series. The method 100c is substantially similar to the methods 100a-b described above. Looking at FIG. 1H, method 100c begins by designing and synthesizing CF editing cassettes 142. In certain embodiments, the CF editing cassettes at 142 comprise pairwise orthogonal and complementary CF editing cassettes, wherein each cassette of a pair is designed to incorporate an edit into an opposite DNA strand at a target locus. That is, each CF editing cassette in a pair comprises a region within the repair template with complementary to the other pairwise cassette for reverse transcription, as well as orthogonal CFgRNA structural elements that are recognized only by their corresponding Cas proteins. These CF editing cassettes transcribe target genome edits, as well as PAM and/or spacer mutations. In certain other embodiments, however, CF editing cassettes may be designed to include both complementary sequences in a single cassette (with, e.g., two CFgRNAs) for editing opposite DNA strands at a target locus with the single cassette. In still other embodiments, single CF editing cassettes may be designed to work in tandem with more conventional gRNAs, wherein structural components of the CFgRNA in the CF editing cassette and the gRNA are orthogonal (i.e., only recognized by a respective Cas protein; see FIG. 1J). Once the CF editing cassettes have been synthesized, the individual CF editing cassettes are amplified and the coded RNA transcript sequence is inserted into a vector backbone, such as a lentiviral backbone, to create editing vectors 144.

Figure 1I:
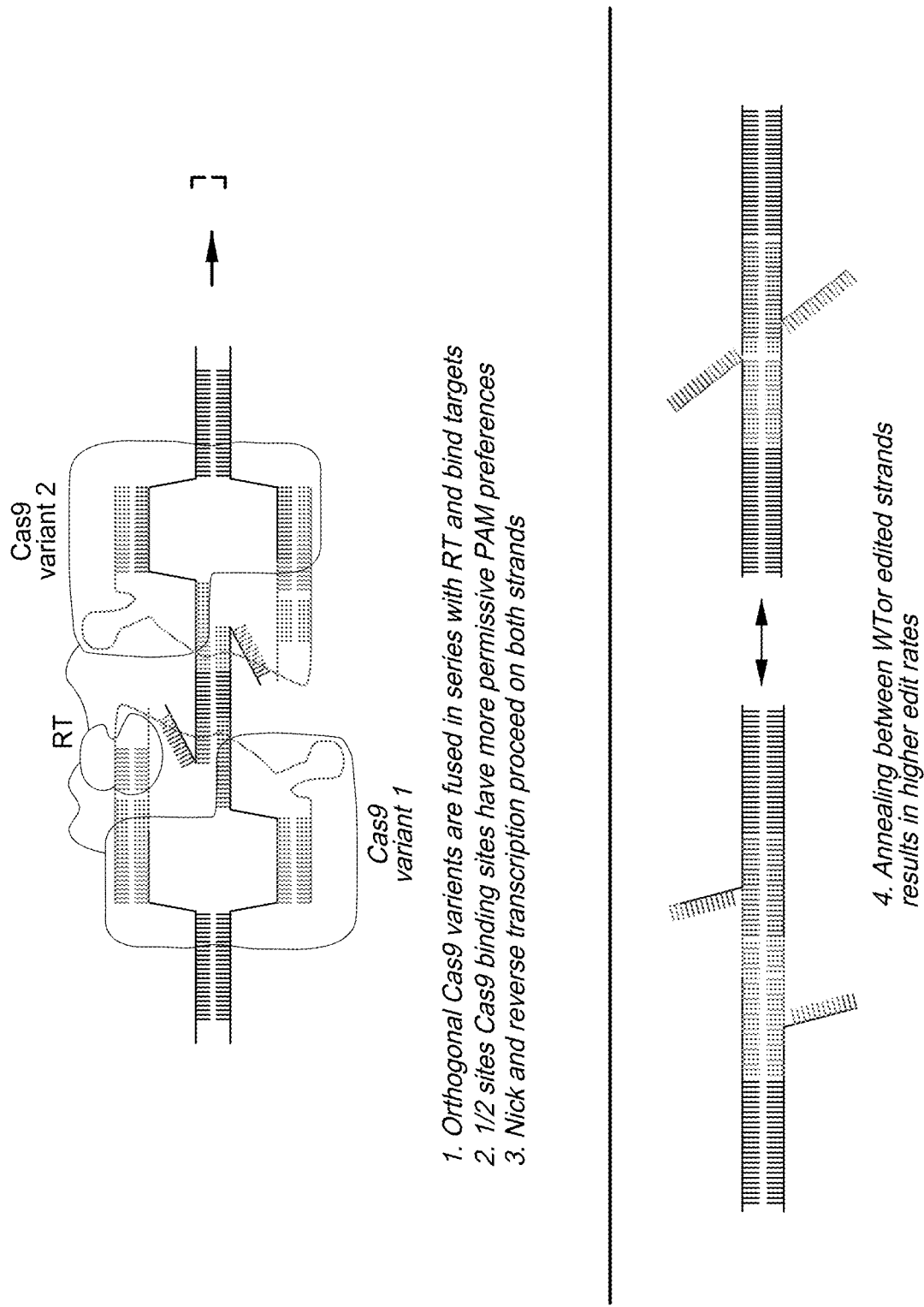
FIG. 1I is a simplified depiction of nickase-RT fusion editing utilizing a nickase-RT fusion enzyme comprising two Cas orthologues fused in series.

In addition, a nuclease or nickase-RT fusion enzyme is designed 146 which includes two orthogonal Cas nuclease or nickase variants fused in series with an RT component, wherein the Cas nuclease or nickase variants may still recognize and cleave at respective target sites. In such embodiments, the orthogonal Cas nuclease or nickase variants may be different Cas nuclease or nickase variants (as shown in FIG. 1I), and the RT component may comprise MLV. Generally, the two orthogonal Cas nuclease or nickase variants may be fused to the RT component in any arrangement. For example, the RT component may be located at the C terminus of the nuclease or nickase-RT fusion enzyme, the N terminus of the nuclease or nickase-RT fusion enzyme, or the RT component may be fused between the first two orthogonal Cas nuclease or nickase variants (shown in FIG. 1I).

The nickase-RT fusion enzyme may be delivered to the cells as a coding sequence in a vector backbone (in some embodiments under the control of an inducible promoter) or the nickase-RT fusion enzyme may be delivered to the cells as a protein or protein complex. The coding sequence for the nickase-RT fusion enzyme may be in a combined engine+editing vector or on a separate vector. In some embodiments, the complementary CF editing cassettes are delivered to the cells via a viral vector where the CF editing cassettes are integrated into the cellular genome. Subsequently, the nickase-RT fusion enzyme is delivered to the cells as a protein. In method 100c, the nickase-RT fusion enzyme is delivered to the cells via a coding sequence in an engine vector 148. At step 150, the engine and editing vectors are introduced into the live cells.

As described with reference to methods 100a-b, a variety of delivery systems may be used to introduce (e.g., transform, transfect or transduce) nucleic acid-guided nickase fusion editing system components into a host cell 150. These delivery systems include the use of yeast systems, lipofection systems, microinjection systems, biolistic systems, virosomes, liposomes, immunoliposomes, polycations, lipid: nucleic acid conjugates, virions, artificial virions, viral vectors, electroporation, cell permeable peptides, nanoparticles, nanowires, exosomes, molecular trojan horse liposomes, and electroporation systems.

Once transformed 150, the next step in method 100c is to provide conditions for nucleic acid-guided nuclease editing 152, which may include incubation of the cells in appropriate medium, and may also include providing conditions to induce transcription of an inducible promoter (e.g., adding antibiotics, chemical inducers, or increasing temperature) for transcription of the coded RNA transcript sequence and/or the nickase-RT fusion enzyme. Once editing is complete, the cells are allowed to recover and are preferably enriched for cells that have edited 154. At this point in method 100e, the cells can be characterized phenotypically or genotypically or optionally steps 150-154 may be repeated to make additional edits 156.

FIG. 1I is a simplified depiction of nickase-RT fusion editing utilizing dual CFgRNAs and a nickase-RT fusion enzyme comprising two Cas nickase variants fused in series. FIG. 1I further depicts the target locus with a first target (pink) and a second target (blue), and the mechanism of repair. The target locus is generally a region of approximately 10 to 300 nucleotides as described supra. The Cas nickase variants in FIG. 1I include Cas9 nickase variants which may each recognize a different PAM site and bind a separate CFgRNA encoding one of two complementary flaps of the same edit (green). As described above, the binding event of one of the two fused Cas nickase variants may greatly reduce the PAM-binding requirements of the second Cas nickase variant, and thus, the second Cas nickase variant may recognize and bind adjacent to a non-canonical PAM site as opposed to a canonical PAM site. Accordingly, in certain embodiments, only one of the first and second targets in the target locus must have a canonical PAM located therein to be bound by one of the two Cas nickase variants of the nickase-RT fusion enzyme, as the second Cas nickase variant may recognize and bind a non-canonical PAM at the other target. As a result of the decreased requirements for the two PAM sites needed for two CRISPR-DNA-type recognition events, the range of target sites accessible by the dual flap strategy is increased.

In one step, the first Cas nickase variant of the nickase-RT fusion enzyme and a corresponding first CF editing cassette bind to the target locus and the Cas nicks the first (top) DNA strand, creating a 3' end. The RT component of the nickase-RT fusion enzyme uses the repair template of the first CF editing cassette as a template to add a first flap of nucleotides to the 3' end of the top DNA strand including the desired edit. In another step, the second Cas nickase variant of the nickase-RT fusion enzyme and the corresponding second CF editing cassette bind to the target locus and the Cas nicks the second (bottom) DNA strand creating a 3' end. The RT component of the nickase-RT fusion enzyme uses the repair template of the second CF editing cassette as a template to add a second flap of nucleotides to the 3' end of the bottom DNA strand including the desired edit, where, the nucleotides added to the top and bottom DNA strands may be complementary to one another. (Note that in embodiments where pairwise cassettes comprise a CFgRNA in a first cassette and a single gRNA in a second cassette (not shown), the first cassette may template the reverse transcription of the first DNA strand to create the first flap, and may then be duplicated by RT-catalyzed DNA polymerase of the newly-made cDNA to template the second flap.) Because the Cas nickase variants remain tightly bound to their respective targets after nicking/cleavage, the effector complex formed by the nickase-RT fusion enzyme and CF editing cassettes may hold the double-stranded DNA break together until the edits are synthesized, which may decrease error-prone repair and/or increase edit rates. After addition of the nucleotides to the 3' ends of both DNA strands, the target locus resolves into either wildtype, where the desired edit is not incorporated (e.g., unproductive resolution), or into an edited target locus.

Figure 1J:
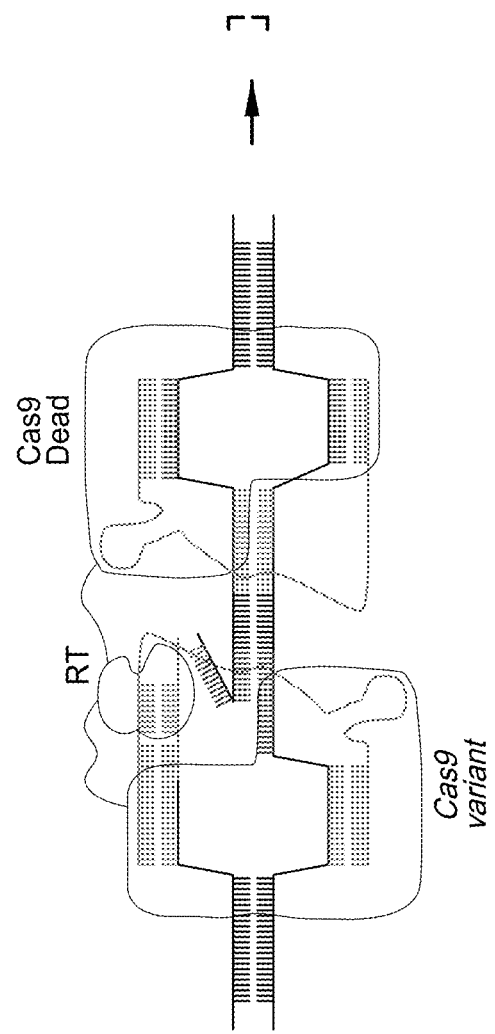
FIG. 1J is another simplified depiction of nickase-RT fusion editing utilizing a nickase-RT fusion enzyme comprising an active Cas orthologue and an inactive Cas orthologue fused in series.

FIG. 1J is a simplified depiction of nickase-RT fusion editing utilizing a nickase-RT fusion enzyme comprising two Cas variants fused in series, wherein one of the two Cas variants is a catalytically active Cas nickase, and the other is a catalytically inactive ("dead") Cas, e.g., dCas9, that still recognizes and binds to a respective target site but does not cleave. The active Cas variant and inactive Cas variant each recognize a different PAM site, and the active Cas variant binds a CF editing cassette while the inactive Cas variant may bind a more conventional CRISPR gRNA.

In such embodiments, only a single flap is formed during editing. However, due to the utilization of a catalytically inactive Cas in combination with an active Cas nickase, a greater range of target sites is accessible to the active Cas nickase for similar reasons as described above with reference to FIG. 1H. That is, the binding event of the catalytically inactive Cas to a site with a canonical site may greatly reduce the PAM-binding requirements of the active Cas nickase, and as a result, the active Cas nickase may become more promiscuous and recognize/bind with non-canonical PAM sites. Accordingly, in certain embodiments, only one of the first and second targets in the target locus must have a canonical PAM site located therein to bind the catalytically inactive Cas variant of the RT-fusion enzyme, as the active Cas variant may recognize and bind a non-canonical PAM site at the other target.

Improved Nucleic Acid-Guided Nickase/Reverse Transcriptase Fusion Editing Using crRNA- and tracrRNA-Encoded Edits The present disclosure further provides compositions of matter, methods, and instruments for nickase-RT fusion editing of live cells using a single CFgRNA and single nickase-RT fusion enzyme, wherein separate components of the CFgRNA are engineered to encode complementary flaps of the desired edit to the target genome (instead of the repair template(s)), thus facilitating editing of opposite DNA strands at a target locus thereof. Such embodiments take advantage of the two-part structure of some guide nucleic acids, such as native type II CRISPR system gRNAs, which generally includes a trans-activating CRISPR RNA (tracrRNA) encoding most of the structural elements recognized by endonucleases, and the CRISPR RNA (crRNA), which binds to the tracrRNA (e.g., via a linker sequence) and encodes a DNA targeting spacer. Accordingly, the two flaps of the desired edit may be encoded on the tracrRNA and crRNA, respectively, and the desired edit may be incorporated in the target genome by utilizing each of the tracrRNA and crRNA as templates for reverse transcription by the RT component of the single nickase-RT fusion. Similar to the embodiments described with reference to FIGS. 1F-1G, in order to create nicks on opposing strands of the target genome at the target locus, an additional, e.g., second, nickase is utilized, which may or may not be a component of the nickase-RT fusion protein, and thus, fused therewith. Because such embodiments require fewer components to assemble at a target locus to create desired edits, more efficient creation of the two flaps for nickase-RT fusion editing may be enabled.

Figure 1K:
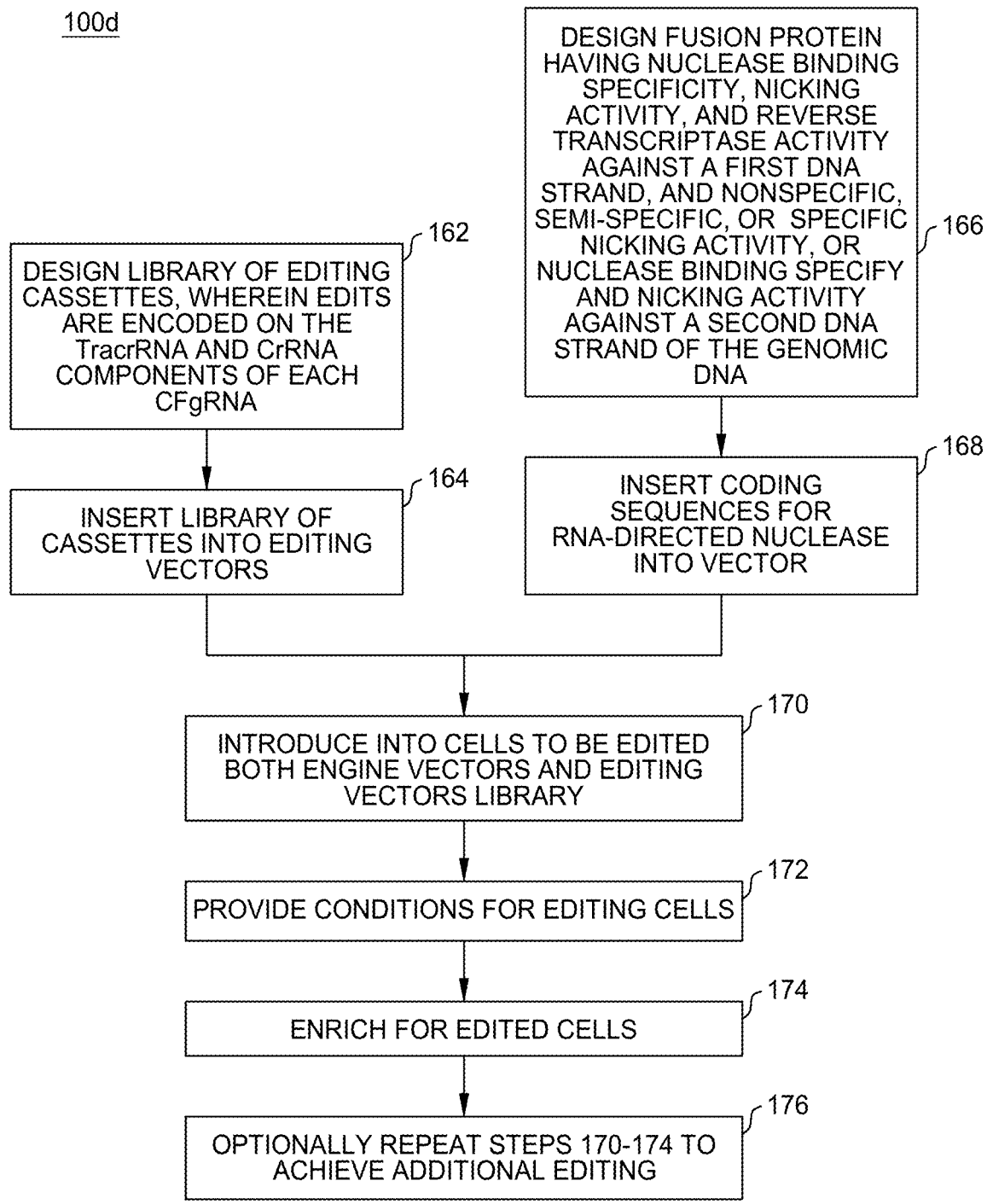
FIG. 1K is a simplified block diagram of an exemplary method for nickase-RT fusion editing of live cells utilizing a CFgRNA with tracrRNA and crRNA components each encoding complementary flaps of a desired edit.

FIG. 1K is a simplified block diagram of an exemplary method 100d for editing live cells via nickase-RT fusion editing utilizing a CFgRNA with tracrRNA and crRNA components each encoding complementary flaps of a desired edit. The method 100d is substantially similar to the methods 100a-100c described above. Looking at FIG. 1K, method 100d begins by designing and synthesizing editing cassettes 162 that comprise a single CFgRNA having a tracrRNA and crRNA annealed to one another and designed to facilitate incorporation of an edit into opposite DNA strands at a target locus. That is, each editing cassette comprises a CFgRNA with a tracrRNA sequence and a crRNA sequence to be transcribed, as well as a PAM or spacer mutation. An additional sequence encoding one or more desired target genome edits is fused to the 3' end of each of the tracrRNA and the crRNA sequence, respectively. In particular, the additional sequence fused to the tracrRNA includes, from 5' to 3', a structural region (e.g., scaffold) recognized by a Cas protein, a region of complementarity to the crRNA, an optional post-edit homology region, an edit region, a nick to edit region, and a PBS region, and the additional sequence fused to the crRNA includes, from 5' to 3', a region of complementarity to the genomic target, a region of complementarity to the tracrRNA, an optional post-edit homology region, an edit region, a nick-to-edit region, and a PBS region. Once the editing cassette or cassettes have been synthesized, the individual editing cassette or cassettes are amplified and the CFgRNA with edit-encoding tracrRNA and crRNA sequences is inserted into a vector backbone, such as a lentiviral backbone, to create editing vectors 164.

In addition, a nickase-RT fusion enzyme is designed 166 to have nuclease binding specificity, specific nicking activity, and reverse transcriptase activity against one strand of the genomic DNA, and nonspecific, semi-specific, or specific nicking activity, or nuclease binding specificity and nicking activity, against a second strand of the genomic DNA. In certain embodiments, the nickase-RT fusion includes a first nickase and a second, additional nickase fused to an RT component, wherein the first nickase is a nickase that recognizes a specific sequence of DNA and the second nickase is a gRNA-guided nickase, a sequence specific nickase, a promiscuous nickase, or a nonspecific nickase. Utilization of a promiscuous or non-specific second nickase reduces the requirements for the two PAM sites needed for two CRISPR-DNA-type recognition events, thus enabling more efficient creation of the two flaps for nickase-RT fusion editing and increasing the range of target sites accessible by the dual flap strategy. Generally, the first and second nickases may be fused to the RT component in any arrangement. For example, the RT component may be located at the C terminus of the nickase-RT fusion, the N terminus of the nickase-RT fusion, or the RT component may be fused between the first and second nickases (shown in FIG. 1L). In certain other embodiments, the nickase-RT fusion protein includes only the first nickase, and the second nickase is an isolated nickase separately recruited during editing.

The nickase-RT fusion enzyme may be delivered to the cells as a coding sequence in a vector backbone (in some embodiments under the control of an inducible promoter) or the nickase-RT fusion enzyme may be delivered to the cells as a protein or protein complex. The coding sequence for the nickase-RT fusion enzyme may be in a combined engine+editing vector or on a separate vector. In some embodiments, the CFgRNA with edit-encoding tracrRNA and crRNA sequences is delivered to the cells via a viral vector where the CFgRNA is integrated into the cellular genome. Subsequently, the nickase-RT fusion enzyme is delivered to the cells as a protein.

In embodiments where the second nickase is an isolated nickase, the second nickase is delivered to the cells as a separate coding sequence in the vector backbone, or as a separate protein or protein complex. In method 100d, the nickase-RT fusion enzyme includes both the first and second nickase fused together with an RT, and is delivered to the cells via a coding sequence in an engine vector 168. At step 170, the engine and editing vectors are introduced into the live cells.

As described with reference to methods 100a-100c, a variety of delivery systems may be used to introduce (e.g., transform, transfect or transduce) nucleic acid-guided nickase fusion editing system components into a host cell 170. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes, molecular trojan horse liposomes, and electroporation systems. Once transformed 170, the next step in method 100d is to provide conditions for nucleic acid-guided nuclease editing 172, which may include incubation of the cells in appropriate medium, and may also include providing conditions to induce transcription of an inducible promoter (e.g., adding antibiotics, adding a chemical inducer, or increasing temperature) for transcription of the CFgRNA with edit-encoding tracrRNA and crRNA sequences and/or the nickase-RT fusion. Once editing is complete, the cells are allowed to recover and are preferably enriched for cells that have edited 174. At this point in method 100d, the cells can be characterized phenotypically or genotypically or optionally steps 170-174 may be repeated to make additional edits 176.

Figure 1L:
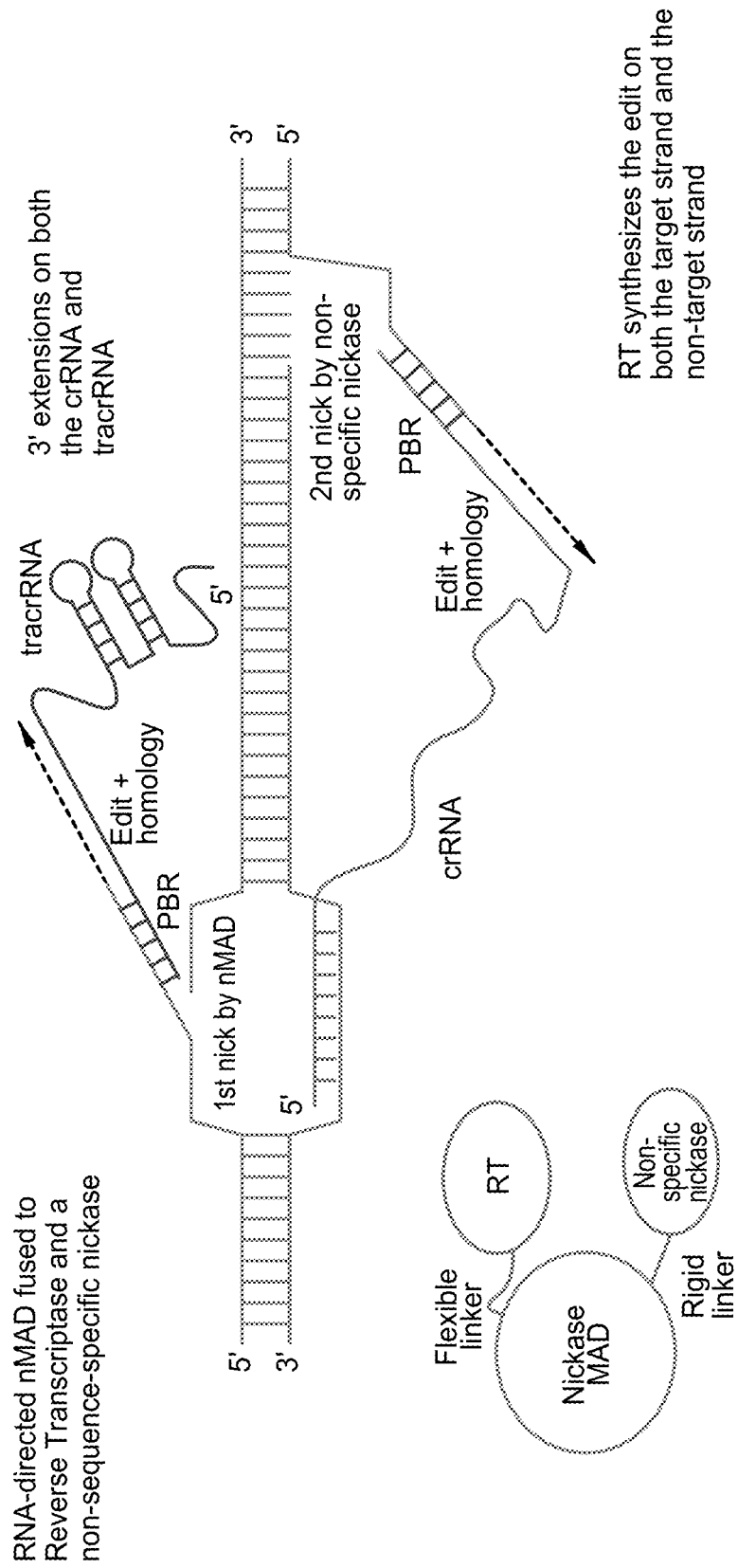
FIG. 1L is a simplified depiction of nickase-RT fusion editing utilizing a single CFgRNA with complementary edits encoded on the tracrRNA and crRNA components.

FIG. 1L is a simplified depiction of nickase-RT fusion editing utilizing a single CFgRNA with edit-encoding tracrRNA and crRNA components showing the nickase-RT with a first nickase and a second, additional nickase, as well as the tracrRNA and crRNA of the CFgRNA. The target locus is generally a region of approximately 10 to 300 nucleotides as described supra. As described above, in order for the nickase-RT and CFgRNA to bind to the target locus and to edit at the target locus, an appropriate PAM must be located in or adjacent to the target locus. In one step, the nickase-RT and CFgRNA bind to the target locus and the first nickase, e.g., a MAD nickase fused to the RT component by a flexible linker, nicks the first (top) strand creating a 3' end. The RT component of the nickase-RT fusion uses the edit fused to the tracrRNA of the CFgRNA as a first template to add nucleotides to the 3' end of the top DNA strand. The region of the top DNA strand that is synthesized by the RT component includes a nick-to-edit region, an edit region, and an optional PEH region.

In another step, the second nickase, which may be, e.g., a specific, promiscuous, or non-specific nickase fused to the first nickase as shown in FIG. 1L by, e.g., a rigid linker, or as an isolated protein or protein complex, nicks the second (bottom) strand and creates a 3' end. Upon forming the second nick, the RT component of the nickase-RT fusion uses the edit fused to the crRNA of the CFgRNA, which is complementary to the edit fused to the tracrRNA, as a second template for adding nucleotides to the 3' end of the bottom DNA strand. Thus, the region of the bottom DNA strand that is synthesized by the RT component includes an optional PEH region, an edit region, and a nick-to-edit region that are at least partially complementary to the PEH, nick-to-edit region, edit region, and a PBS region, respectively, of the top strand. After addition of the nucleotides to the 3' ends of both DNA strands, the target locus resolves into either wildtype, where the desired edit is not incorporated, or into an edited target locus.

Although the first and second nicking events above are described as being initiated by separate nickases, a single wildtype Cas9 or other nuclease may be utilized to form both nicks certain embodiments. In such embodiments, however, only an insertion edit is possible as the desired edit.

Improved Nucleic Acid-Guided Nickase/Reverse Transcriptase Fusion Editing Using an RNA Bridge Embodiments of the present disclosure further provide compositions of matter, methods, and instruments for nickase-RT fusion editing of live cells using a single RNA transcript comprising both a type V Cas gRNA and a type II Cas gRNA, or two type II Cas gRNAs, connected by a nucleic acid linker sequence. The type V and/or type II gRNAs recruit corresponding proteins, which recognize their respective motifs within the single RNA transcript and form a complex therewith that binds with a target site. In such embodiments, both flaps of a desired edit to the target genome are encoded on the single RNA transcript along with the type V and/or type II Cas gRNAs, thus facilitating simultaneous editing of opposite DNA strands at a target locus, or editing of both DNA strands in quick succession, by ensuring all of the necessary components are present at the same time and in the same complex.

Figure 1M:
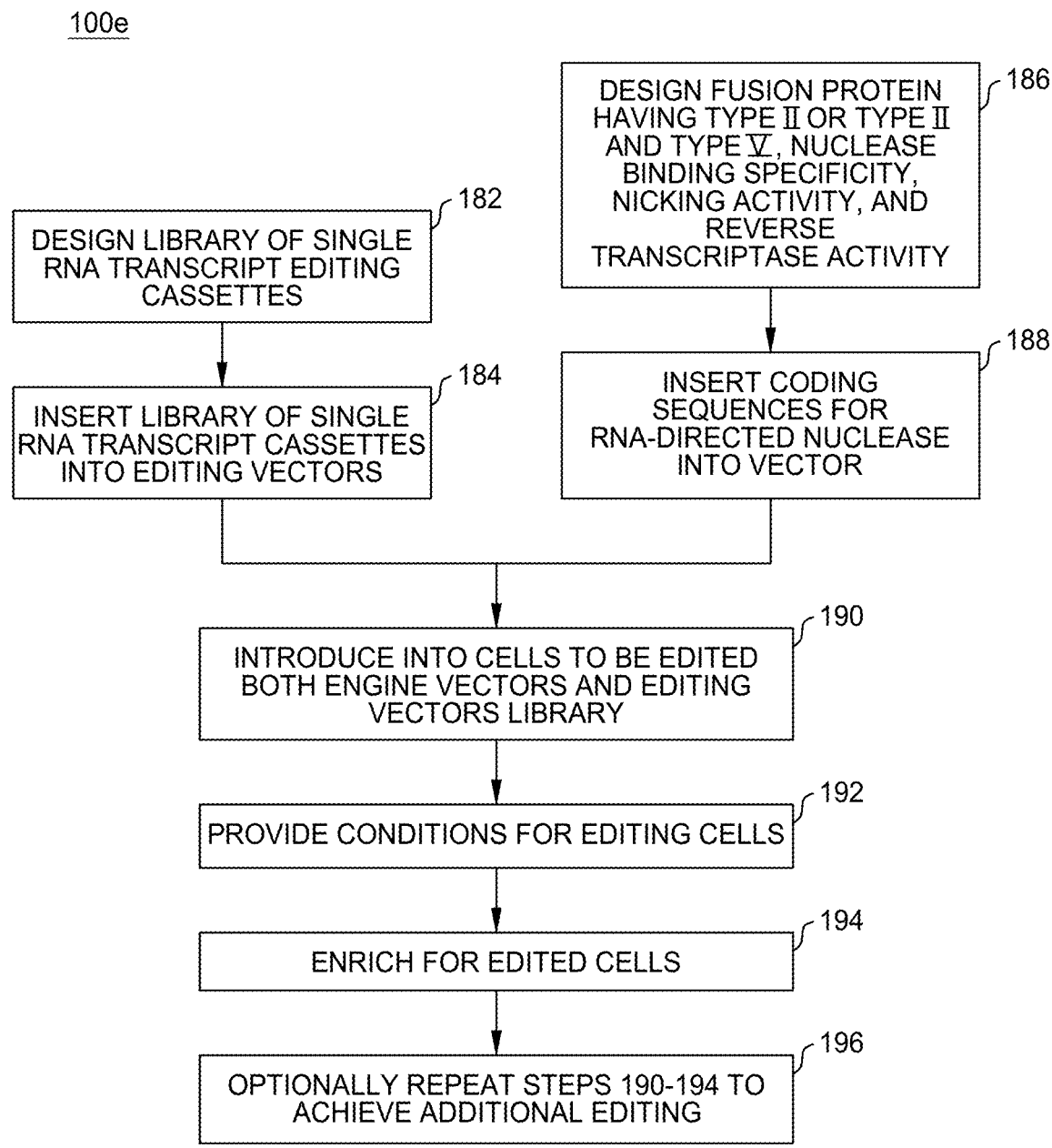
FIG. 1M is a simplified block diagram of an exemplary method for nickase-RT fusion editing of live cells utilizing an RNA bridge.

FIG. 1M is a simplified block diagram of an exemplary method 100e for editing live cells via nickase-RT fusion editing utilizing an RNA bridge. The method 100e is substantially similar to the methods 100a-d described above. Looking at FIG. 1M, method 100e begins by designing and synthesizing editing cassettes 182 that encode for a single RNA transcript including both a type V Cas gRNA and a type II Cas gRNA, or two type II Cas gRNAs, connected by a linker sequence and designed to facilitate incorporation of an edit into opposite DNA strands at a target locus. That is, each editing cassette comprises a sequence encoding a single RNA transcript with a type II Cas gRNA sequence linked to a type V or type II Cas gRNA sequence and one or more desired genome edits to be transcribed, as well as a PAM or spacer mutation. Complementary desired genome edits (i.e., complementary flaps) may be encoded in, e.g., the linker sequence between the gRNA sequences and at the 3' end of the RNA transcript. Once the editing cassettes have been synthesized, the individual editing cassettes are amplified and the coded RNA transcript sequence is inserted into a vector backbone, such as a lentiviral backbone, to create editing vectors 184.

Additionally, two or more nickase fusion enzymes, at least one of which is fused to an RT, are also designed 186 to bind with the type V and/or type II Cas gRNAs during editing. In certain embodiments, the nickase-RT fusion enzymes may each include a Cas variant fused to an additional nickase (e.g., Cas-nickase-RT), wherein the Cas variant is a catalytically inactive variant, e.g., catalytically inactive ("dead") Cas9, that still recognizes a respective motif within the RNA transcript and binds to targets specified by spacers within the RNA transcript, but does not cleave at a respective target site. In such embodiments, the nickase fused thereto may be a specific, promiscuous, or nonspecific nickases or nucleases. Generally, the Cas variants and nickases may be fused to the RT components in any arrangement. For example, the RT component may be located at the C terminus of the nickase-RT fusion, the N terminus of the nickase-RT fusion, or the RT component may be fused between the Cas variant and nickases. In certain other embodiments, the Cas variant is an active nickase or nuclease rather than a catalytically inactive mutant, and thus, the Cas variant is not bound to a nickase. In further embodiments, the nickase-RT fusion enzymes include MLV as the RT component.

The nickase-RT fusion enzymes may be delivered to the cells as coding sequences in a vector backbone (in some embodiments under the control of an inducible promoter) or the nickase-RT fusion enzymes may be delivered to the cells as proteins or protein complexes. The coding sequences for the nickase-RT fusion enzymes may be in a combined engine+editing vector or on a separate vector. In some embodiments, the coded RNA transcript sequence is delivered to the cells via a viral vector where the coded RNA transcript sequence is integrated into the cellular genome. Subsequently, the nickase-RT fusion enzymes are delivered to the cells as a protein. In method 100e, the nickase-RT fusion enzymes include catalytically inactive Cas variants (e.g., dCas9) and/or catalytically inactive MAD variants (e.g., dMAD7, dMAD2007, dMAD2011, dMAD2017, dMAD2019, dMAD297, dMAD298, dMAD299) and nickases fused together with an RT, and are delivered to the cells via a coding sequence in an engine vector 188. At step 190, the engine and editing vectors are introduced into the live cells.

As described with reference to methods 100a-d, a variety of delivery systems may be used to introduce (e.g., transform, transfect, or transduce) nucleic acid-guided nickase fusion editing system components into a host cell 190. These delivery systems include the use of yeast systems, lipofection systems, microinjection systems, biolistic systems, virosomes, liposomes, immunoliposomes, polycations, lipid: nucleic acid conjugates, virions, artificial virions, viral vectors, electroporation, cell permeable peptides, nanoparticles, nanowires, exosomes, molecular trojan horse liposomes, and electroporation systems. Once transformed 190, the next step in method 100e is to provide conditions for nucleic acid-guided nuclease editing 192, which may include incubation of the cells in appropriate medium, and may also include providing conditions to induce transcription of an inducible promoter (e.g., adding antibiotics, chemical inducers, or increasing temperature) for transcription of the coded RNA transcript sequence and/or the nickase-RT fusion. Once editing is complete, the cells are allowed to recover and are preferably enriched for cells that have edited 194. At this point in method 100e, the cells can be characterized phenotypically or genotypically or optionally steps 190-194 may be repeated to make additional edits 196.

Figure 1N:
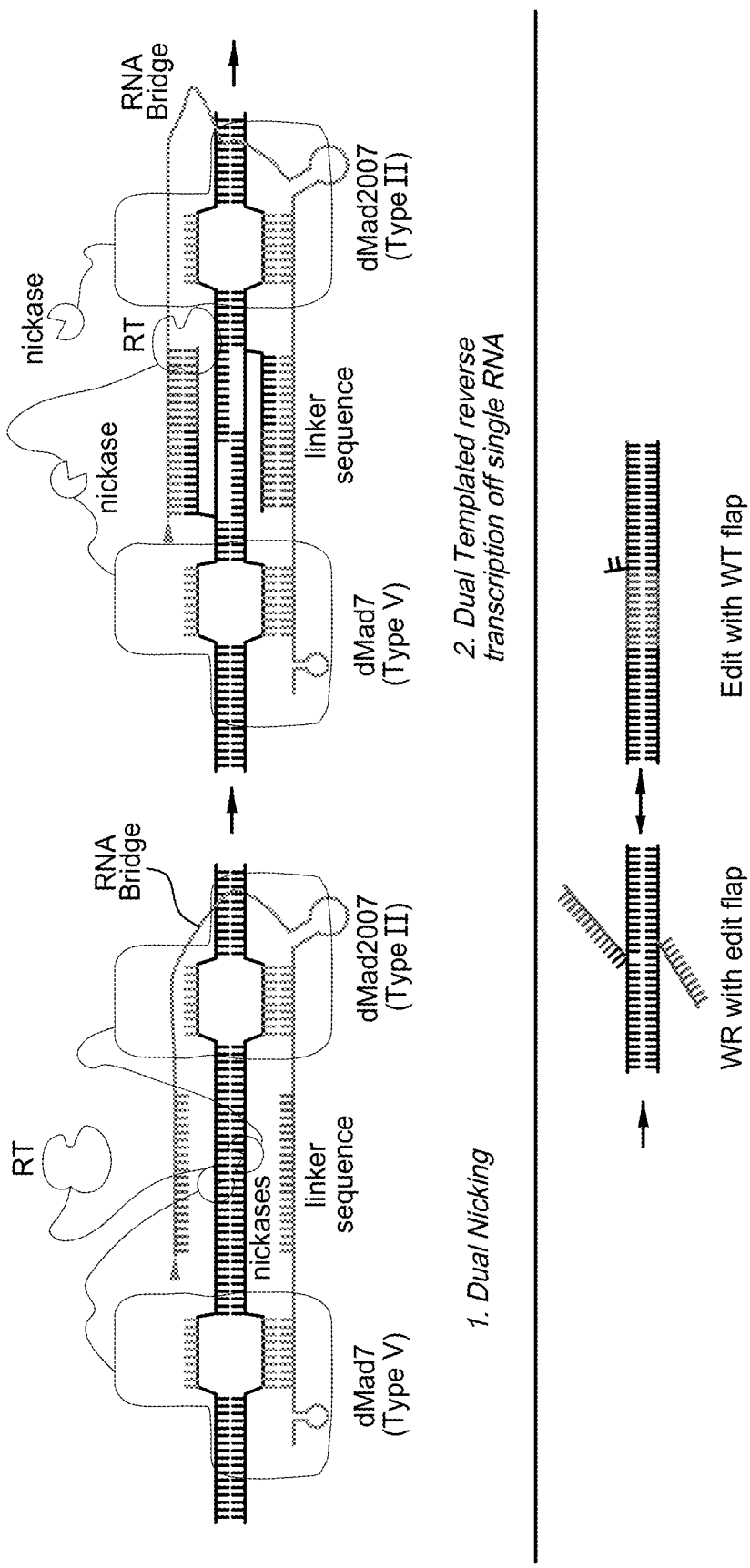
FIG. 1N is a simplified depiction of nickase-RT fusion editing utilizing an RNA bridge.
Figure 10:
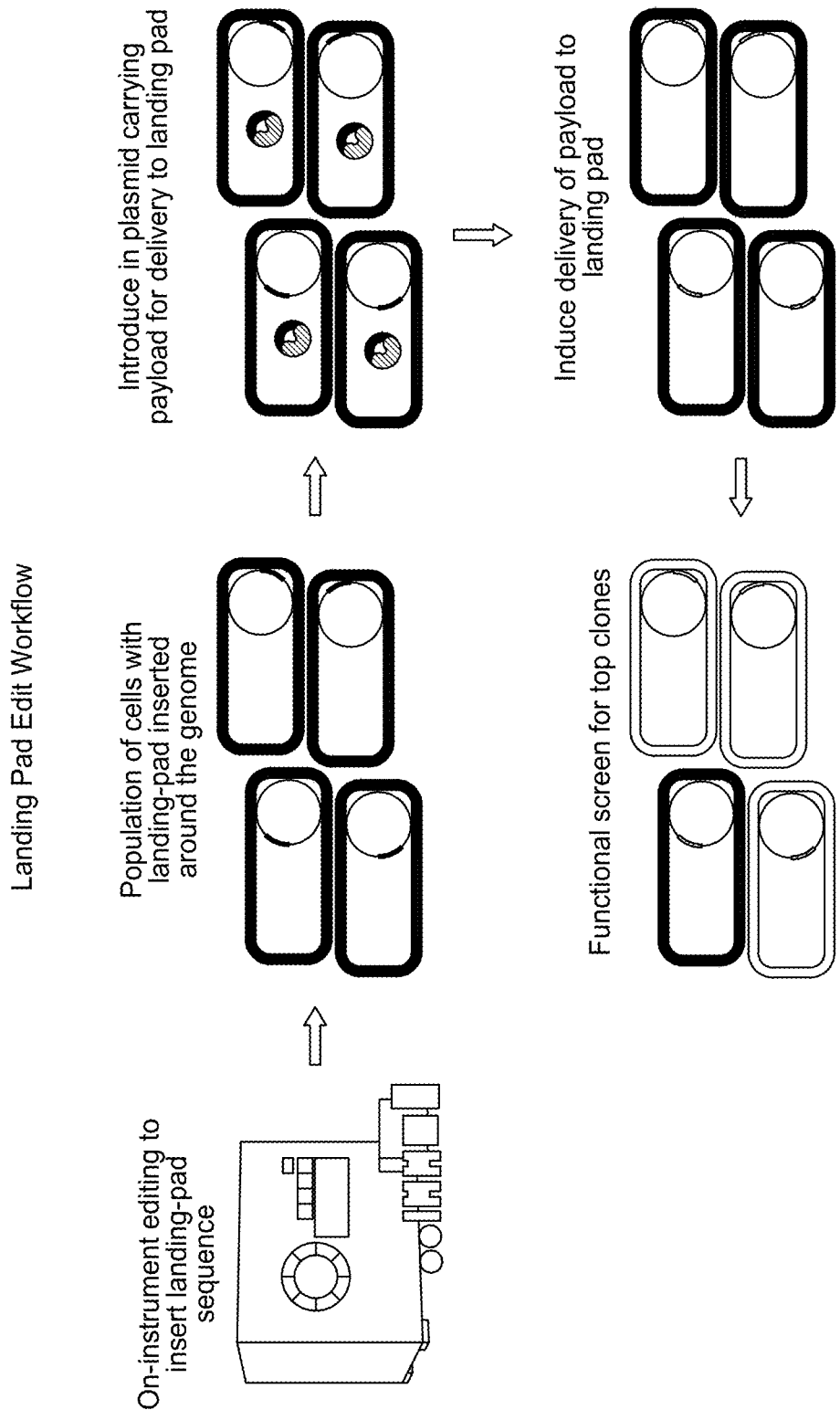
FIGS. 10A-10D schematically illustrate CF editing cassette design for various CF editing cassettes used in nickase-RT fusion editing insertion studies.

FIG. 1N is a simplified depiction of nickase-RT fusion editing utilizing an RNA bridge (i.e., transcript) comprising both type V and type II Cas gRNAs connected by a linker, as well as both edit flaps (green). In addition to the RNA transcript, FIG. 1N depicts a first and a second nickase-RT enzyme recruited by the type V and type II Cas gRNAs to the target locus, and the mechanism of repair. Each of the first and second nickase-RT enzymes in FIG. 1N includes a catalytically inactive Cas9 variant (dMAD7 and dMAD2007 are shown) and a nickase fused therewith. However, in certain other embodiments, active Cas9 nucleases or nickases may be utilized, therefore not requiring fusion to an additional nickase. The target locus is generally a region of approximately 10 to 300 nucleotides as described supra. As described in relation to FIGS. 1B-1C above, in order for the nickase-RT enzymes and RNA transcript to bind to the target locus and to edit at the target locus, an appropriate PAM must be located in or adjacent to the target locus.

In one step, or multiple steps in quick succession, the multiple Cas RNA complex binds to both strands of the genomic DNA at the target locus and the nickases of each nickase-RT fusion enzymes nick opposite strands thereof, creating a 3' end on the first (top) strand and a 3' end on the second (bottom) strand. The single RNA transcript and Cas proteins, while bound to both strands of the genomic DNA, creates a non-covalent bridging of the genomic DNA after the nicking, holding the entire complex in place for incorporation of the desired edits. The RT component of one or both nickase-RT fusion enzymes then uses the RNA transcript as a template to add nucleotides to the 3' ends of the top and bottom DNA strands, including the encoded desired edit(s), which may be encoded as complementary sequences in the linker sequence (green) between gRNAs and at the 3' end of the RNA transcript (green). The region of the top DNA strand that is synthesized by the RT component includes an optional post-edit homology region, a nick-to-edit region, an edit region, and a PBS region, while the region of the bottom DNA strand that is synthesized by the RT component includes an optional PEH region, an edit region, and a nick-to-edit region that are complementary to the nick-to-edit region, edit region, and a PBS region, respectively, of the top strand. After addition of the nucleotides to the 3' ends of both DNA strands, the target locus resolves into either wildtype, where the desired edit is not incorporated, or into an edited target locus toward which resolution is biased.

FIG. 1O is a simplified diagram of a process for utilizing and leveraging nickase/RT fusion editing to integrate landing pads into genomic DNA for subsequent donor DNA insertion in recursive rounds of editing. Note that while FIG. 1O depicts circular genomes for purposes of clarity and illustration, the illustrated process is amenable to mammalian cells, as well as other types of cells.

The method begins with editing of a cell population to integrate a landing pad sequence into the cellular genome (e.g., utilizing Methods 100a, 100b, 100c, 100d, or 100e described above). In certain embodiments, editing is carried out via dual CF editing cassette nickase/RT fusion editing, preferably in an automated manner using an instrument (depicted at left in FIG. 1O) such as described U.S. Pat. Nos. 10,253,316; 10,329,559; 10,323,242; 10,421,959; 10,465, 185; 10,519,437; 10,584,333; 10,584,334; 10,647,982; 10,689,645; 10,738,301; 10,738,663; 10,947,532; 10,894, 958; 10,954,512; and 11,034,953; and U.S. Ser. No. 17/239, 540. After editing, the population of cells comprise a genome with an integrated landing pad sequence, which may in certain embodiments be integrated into different loci around the genome, depicted as a black bar on a circular genome in the cell.

In certain embodiments, following insertion of the landing pad sequence the genome, the cells are then transformed, transfected (e.g., via electroporation), or transduced with a plasmid or other vector carrying a donor DNA sequence to be delivered to the landing pad (depicted as striped bars on the vectors in the cells). In certain embodiments, however, integration of the landing pad and integration of the plasmids is carried out in a single transfection. Generally, each plasmid or vector may comprise 1) a coding sequence for an appropriate recombinase/integrase or meganuclease targeting the landing pad recognition sequence; and 2) either a large donor DNA sequence flanked by either the recombinase or integrase recognition sequence for recombinase/integrase-mediated insertion into the landing pad in the genome, or a large donor DNA sequence flanked by homology arm sequences for HDR-mediated insertion into the genome via the meganuclease. In an optional step, the plasmid or vector also comprises a coding sequence for a selection marker and the cells are selected after transformation.

After transformation and optional selection, delivery of the donor DNA sequences to the landing pads in the cells may be induced by inducing expression of the recombinase/integrase or meganuclease. The cells with the DNA payload delivered to the landing pads are allowed to recover and grow and then are screened. Note that after delivery of the donor DNA sequence to the landing pads, the black bar on the chromosome in the cells is transformed into a striped bar. Screening for proper integration of the donor DNA sequences includes but is not limited to 1) polymerase chain reaction (PCR) analysis with appropriate primer sets used to assess whether the delivery vector was correctly integrated at the target site; 2) assessment of activity of the nucleic acid of interest, including but not limited to a metabolic test, measurement of transcript level, a phenotypic assay, or detection of a protein product using an antibody specific to the protein product; 3) DNA sequencing of the integrated sequence; and/or 4) RNA sequencing of integrated and expressed genes. Exemplary applications of the present compositions and methods include genome-wide delivery of large-insert promoter libraries; delivery of heterologous genes or pathways to a large number of genomic locations enabling examination of location-dependent expression effects; delivery of CFgRNAs, gRNAs, or barcodes in a single location to enable trackability of additional genomic edits; and delivery of fusion-protein partners to multiple loci around the genome.

Figure 1P:
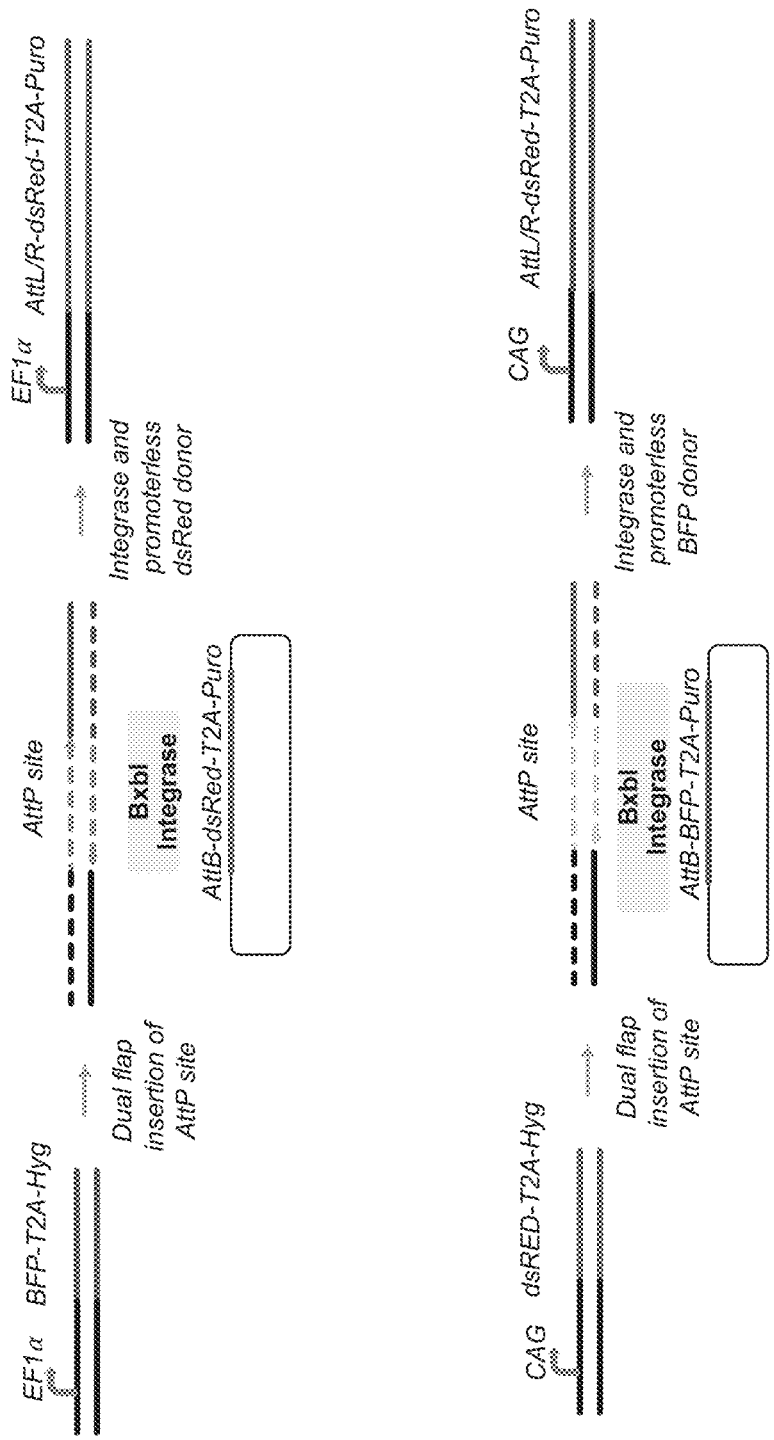

FIG. 1P illustrates two specific examples of genomic landing pad integration followed by donor DNA sequence insertion. At top, an AttP integrase recognition site, or other suitable enzyme recognition site of ~50 bp or more, is integrated via dual flap editing into, e.g., a BF-T2A-Hyg target locus of a population of cells that is under the control of an EF1α promoter. Thereafter, a plasmid comprising a promoterless dsRed donor sequence, e.g., AttB-dsRED-T2A-Puro, is transformed into the cells along with a unidirectional integrase, e.g., a Bxbl integrase, which mediates efficient integration of the dsRed donor sequence (and, in certain embodiments, the entire plasmid) into the genome at the previously-integrated landing pad. Accordingly, a successful insertion of the donor sequence will result in the substitution of BFP for dsRed expression, which may be verified by flow cytometry or sequencing.

At bottom in FIG. 1P, a similar mechanism is depicted, but for substituting dsRed at a CAG promoter-driven dsRed-T2A-Hyg target locus with BFP from a promoterless AttB-BFP-T2A-Puro donor sequence. Accordingly, a successful insertion of the donor sequence will result in the substitution of dsRed for BFP, which may be verified by flow cytometry or sequencing.

Exemplary Embodiments for Delivery of Reagent Bundles to Mammalian Cells

In the editing methods described herein, cells, such as, in one embodiment, stem cells to be edited may be grown for several passages, e.g., off instrument, to assure cell health. The cells may be grown in 2D culture, in 3D culture (if the cells are viable when grown in or adapted to 3D culture) or on microcarriers. This initial cell growth typically takes place off the automated instrument (the instrument is described infra in relation to FIGS. 3A-3E). If necessary, the cells are dissociated and added to medium in the bioreactor comprising cell growth medium such as MEM, DMEM, RPMI, or, for stem cells, mTeSRPlus serum-free, feeder-free cell culture medium (STEMCELL Technologies Canada INC., Vancouver, BC) and cell growth microcarriers. If the cells are grown initially on microcarriers, the microcarriers are transferred to the bioreactor comprising cell growth medium such as mTeSR™ Plus serum-free, feeder-free cell culture medium (STEMCELL Technologies Canada INC., Vancouver, BC) and additional microcarriers. Approximately 1e7 or 1e8 cells are transferred to the cell growth module on the automated instrument for growth.

In parallel with the off-instrument cell growth, reagent bundle microcarriers (RBMCs) are manufactured, also off-instrument. The present description provides depictions two exemplary methods for manufacturing RBMCs (see FIGS. 2A and 2B) that may be used to edit the cells in the modules and automated instruments described herein.

The cells are grown in 3D culture on microcarriers in the bioreactor for, e.g., three to four days or until a desired number of cells, e.g., 1e8, cells are present. These processes may take place in the bioreactor and cell corral (described infra). During this growth cycle, the cells are monitored for cell number, pH, and optionally other parameters. As described above, cell growth monitoring can be performed by imaging, for example, by allowing the microcarriers to settle and imaging the bottom of the bioreactor. Alternatively, an aliquot of the culture may be removed and run through a separate flow cell, e.g., in a separate module, for imaging. For example, the cell corral, in addition to being integrated with the bioreactor vessel, may be integrated with a flow cell or other device for cell counting where an aliquot of the cell culture in the cell corral may be removed and counted in the flow cell. In another alternative, the cells may express a fluorescent protein and fluorescence in the cell culture is measured or fluorescent dye may be used to stain cells, particularly live cells. This microcarrier-based workflow can be performed in the bioreactor and cell corral with most if not all steps performed in the same device; thus, several bioreactors and cell corrals may be deployed in parallel for two to many samples simultaneously. In yet another alternative, permittivity or capacitance is used to monitor cell coverage on the microcarriers. In yet another embodiment, an aliquot of cells may be removed from the bioreactor or cell corral and transported out of the instrument and manually counted on a commercial cell counter (i.e., Thermofisher Countess, Waltham, MA). Cell aliquots from the stem cell culture to be used to monitor pluripotency may be removed via "liquid out" ports in the bioreactor The microcarriers used for initial cell growth can be nonporous (where pore sizes are typically <20 nm in size), microporous (with pores between >20 nm to <1 µm in size), or macroporous (with pores between >1 µm in size, e.g. 20 µm). In microcarrier culture, cells grow as monolayers on the surface of nonporous or microporous microcarriers, which are typically spherical in morphology; alternatively, the cells grow on the surface and as multilayers in the pores of macroporous microcarriers. The microcarriers preferably have a density slightly greater than that of the culture medium to facilitate easy separation of cells and medium for, e.g., medium exchange and imaging and passaging; yet the density of the microcarriers is also sufficiently low to allow complete suspension of the microcarriers at a minimum stirring or bubbling rate. Maintaining a low stirring or bubbling rate is preferred so as to avoid hydrodynamic damage to the cells.

The microcarriers used for cell growth depend on cell type and desired cell numbers, and typically include a coating of a natural or synthetic extracellular matrix or cell adhesion promoters (e.g., antibodies to cell surface proteins or poly-L-lysine) to promote cell growth and adherence. Microcarriers for cell culture are widely commercially available from, e.g., Millipore Sigma, (St. Louis, MO, USA); Thermo Fisher (Waltham, MA, USA); Pall Corp. (Port Washington, NY, USA); GE Life Sciences (Marlborough, MA, USA); and Corning Life Sciences (Tewkesbury, MA, USA). As for the extracellular matrix, natural matrices include collagen, fibrin and vitronectin (available, e.g., from ESBio, Alameda, CA, USA), and synthetic matrices include Matrigel® (Corning Life Sciences, Tewkesbury, MA, USA), Geltrex™ (Thermo Fisher Scientific, Waltham, MA, USA), Cultrex® (Trevigen, Gaithersburg, MD, USA), biomemetic hydrogels available from Cellendes (Tubingen, Germany); and tissue-specific extracellular matrices available from Xylyx (Brooklyn, NY, USA); further, denovoMatrix (Dresden, Germany) offers screenMATRIX™, a tool that facilitates rapid testing of a large variety of cell microenvironments (e.g., extracellular matrices) for optimizing growth of the cells of interest.

Following cell growth, passaging is performed by, e.g., stopping the impeller rotation or bubbling action in the bioreactor and allowing the microcarriers to settle. In one method, the cells are removed from the microcarriers using enzymes such as collagenase, trypsin or pronase, or by non-enzymatic methods including EDTA or other chelating chemicals, and once removed from the carriers, medium is added to dilute the enzyme to inhibit enzymatic action. The dissociation procedures relating to the cell corral are described in detail infra. Once medium is added, then the cells are separated from the microcarriers by allowing the microcarriers to settle and aspirating the cells via a filtered sipper into the cell corral. The cells then may be optionally dissociated from one another via a filter, sieve or by bubbling or other agitation in the cell corral and aliquots removed, e.g., for pluripotency determination. Next, microcarriers comprising the manufactured reagent bundles (RBMCs) and the dissociated cells are combined in an appropriate medium in the growth vessel. Alternatively, instead of removing cells from the cell growth microcarriers and re-seeding on RBMCs, the cells may be transferred from the cell growth microcarriers to RBMCs via microcarrier bridge passaging either in the growth vessel in a reduced volume or in the cell corral. Bridge passaging involves allowing a new microcarrier (e.g. an RBMC) to come into physical contact with a cell-laden microcarrier, such that cells on the latter microcarrier can migrate to the RBMC.

RBMCs are not prepared on-instrument but are pre-manufactured. The microcarriers used for reagent bundles may be microporous microcarriers, which, due to the plethora of micropores, can carry a larger reagent payload per carrier diameter than nonporous or macroporous microcarriers. Preferred RBMCs are microporous, to provide increased surface area for reagent delivery, and functionalized on the surface so as to be able to bind reagents. Preferred microcarriers for RBMCs include Pierce™ Streptavidin UltraLink™ Resin, a cross-linked polyacrylamide carrier functionalized with streptavidin comprising a pore size of 50 to 100 nm; Pierce™ NeutrAvidin™ Plus UltraLink™ Resin, cross-linked polyacrylamide carrier functionalized with avidin comprising a pore size of 50 to 100 nm; and UltraLink™ Hydrazide Resin, a cross-linked polyacrylamide carrier functionalized with hydrazine comprising a pore size of 50 to 100 nm, all available from Thermo Fisher (Waltham, MA, USA); cross-linked agarose resins with alkyne, azide, photo-cleavable azide and disulfide surface functional groups available from Click Chemistry Tools (Scottsdale, AZ, USA); Sepharose™ Resin, cross-linked agarose with amine, carboxyl, carbodiimide, N-hydroxysuccinimide (NETS), and epoxy surface functional groups available from GE Health (Chicago, IL, USA).

The microcarriers are loaded with amplified editing cassettes or amplified editing plasmids, engine plasmids, nuclease or nuclease fusion proteins, mRNAs or ribonucleoproetins (RNPs) depending on, e.g., the functionalized group, via, e.g., via chemical or photo linkage or depending on a surface coating on the microcarrier, if present. RBMCs are prepared by 1) partitioning and amplifying a single copy of an editing cassette to produce clonal copies in an RBMC, or by 2) pooling and amplifying editing cassettes, followed by dividing the editing cassettes into sub-pools and "pulling down" the amplified editing cassettes with microcarriers comprising nucleic acids specific to and complementary to unique sequences on the editing cassettes. The step of sub-pooling acts to "de-multiplex" the editing cassette pool, thereby increasing the efficiency and specificity of the "pull down" process. De-multiplexing thus allows for amplification and error correction of the editing cassettes to be performed in bulk followed by efficient loading of clonal copies of the editing cassettes onto a microcarrier.

An exemplary option for growing, passaging, transfecting and editing induced pluripotent stem cells (iPSCs), where there is sequential delivery of clonal high copy number (HCN) RBMCs—i.e., lipid nanoparticle-coated microcarriers, where each microcarrier is coated with many copies of delivery vehicles (e.g., RNA, DNA, plasmid, or ribonucleoprotein) carrying a single clonal editing cassette—followed by bulk enzyme delivery. Note that the bioreactors and cell corrals described infra may be used for all processes. First, cells are seeded on the RBMCs to deliver clonal copies of nucleic acids to the cells. Again, the RBMCs are typically fabricated or manufactured off-instrument. The cells are allowed to grow and after 24-48 hours, medium is exchanged for medium containing antibiotics to select for cells that have been transfected. The cells are passaged, re-seeded and grown again, and then passaged and re-seeded, this time onto microcarriers comprising lipofectamine with the enzyme provided as a coding sequence under the control of a promoter, or as a protein on the surface of a microcarrier. As an alternative, the enzyme may be provided in bulk in solution. The enzyme is taken up by the cells on the microcarriers, and the cells are incubated and allowed to grow. Medium is exchanged as needed and the cells are detached from the microcarriers for subsequent growth and analysis.

An alternative exemplary option comprises the steps of growing, passaging, transfecting and editing iPSCs. In this embodiment, there is simultaneous delivery of clonal high copy number (HCN) RBMCs (i.e., reagent bundle lipid nanoparticle-coated microcarriers) where each microcarrier is coated with many copies of delivery vehicles (e.g., RNA, DNA, plasmid, or ribonucleoprotein) carrying a single clonal editing cassette—and enzyme (e.g., as a coding sequence under the control of a promoter therefor, as a ribonucleoprotein complex, or as a protein). Again, the RBMCs are typically fabricated or manufactured off-instrument. Note that the integrated instrument described infra may be used for all processes. As with the workflow described above, first cells are seeded on microcarriers to grow. The cells are then passaged, detached, re-seeded, grown and detached again to increase cell number, with medium exchanged every 24-72 hours as needed. Following detachment, the cells are seeded on RBMCs for clonal delivery of the editing cassette and enzyme in a co-transfection reaction. Following transfection, the cells grown for 24-48 hours after which medium is exchanged for medium containing antibiotics for selection. The cells are selected and passaged, re-seeded and grown again. Medium is exchanged as needed and the cells are detached from the microcarriers for subsequent growth and analysis.

Figure 2A:
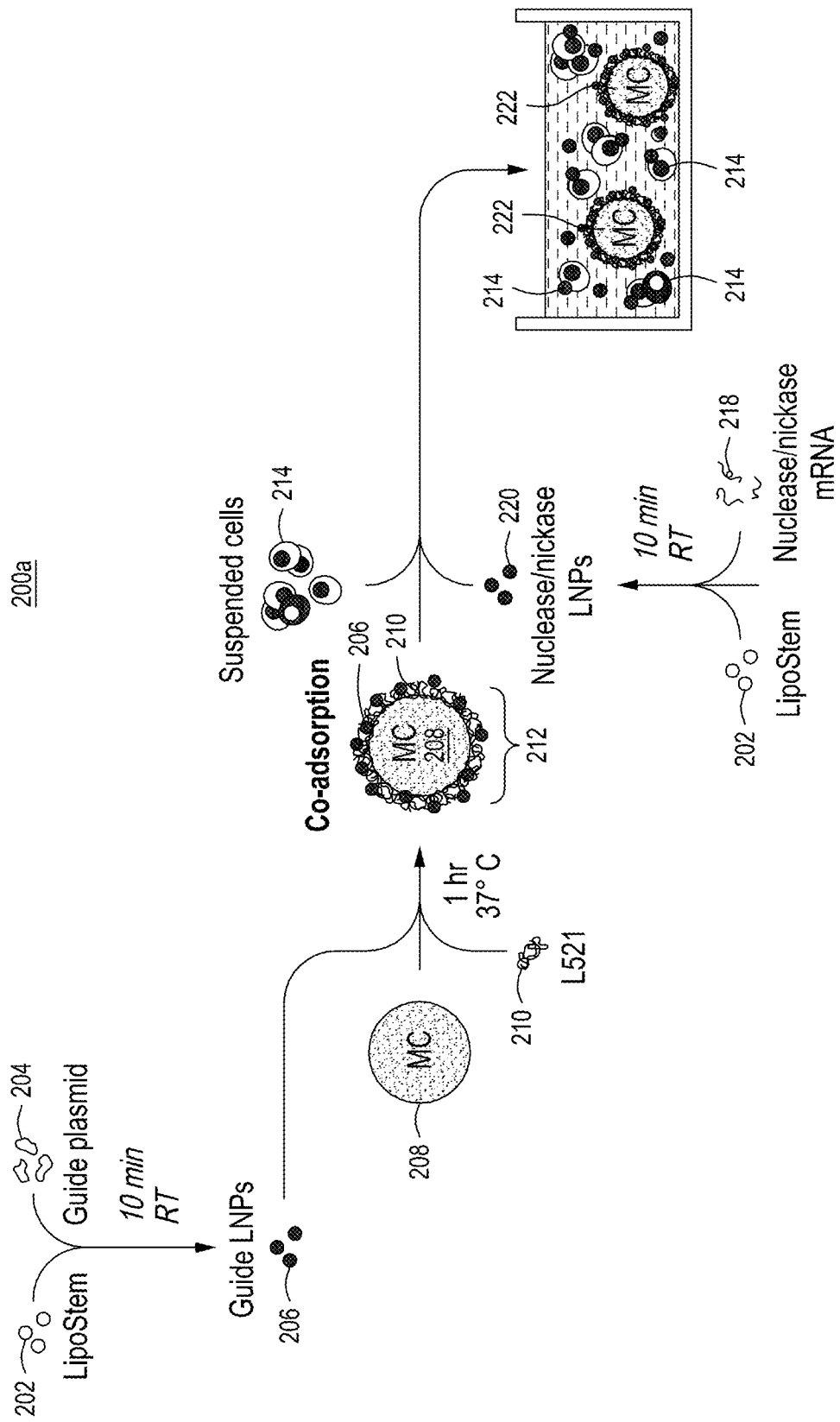
FIG. 2A depicts an exemplary workflow employing microcarrier-partitioned delivery for editing cells.
Figure 2B:
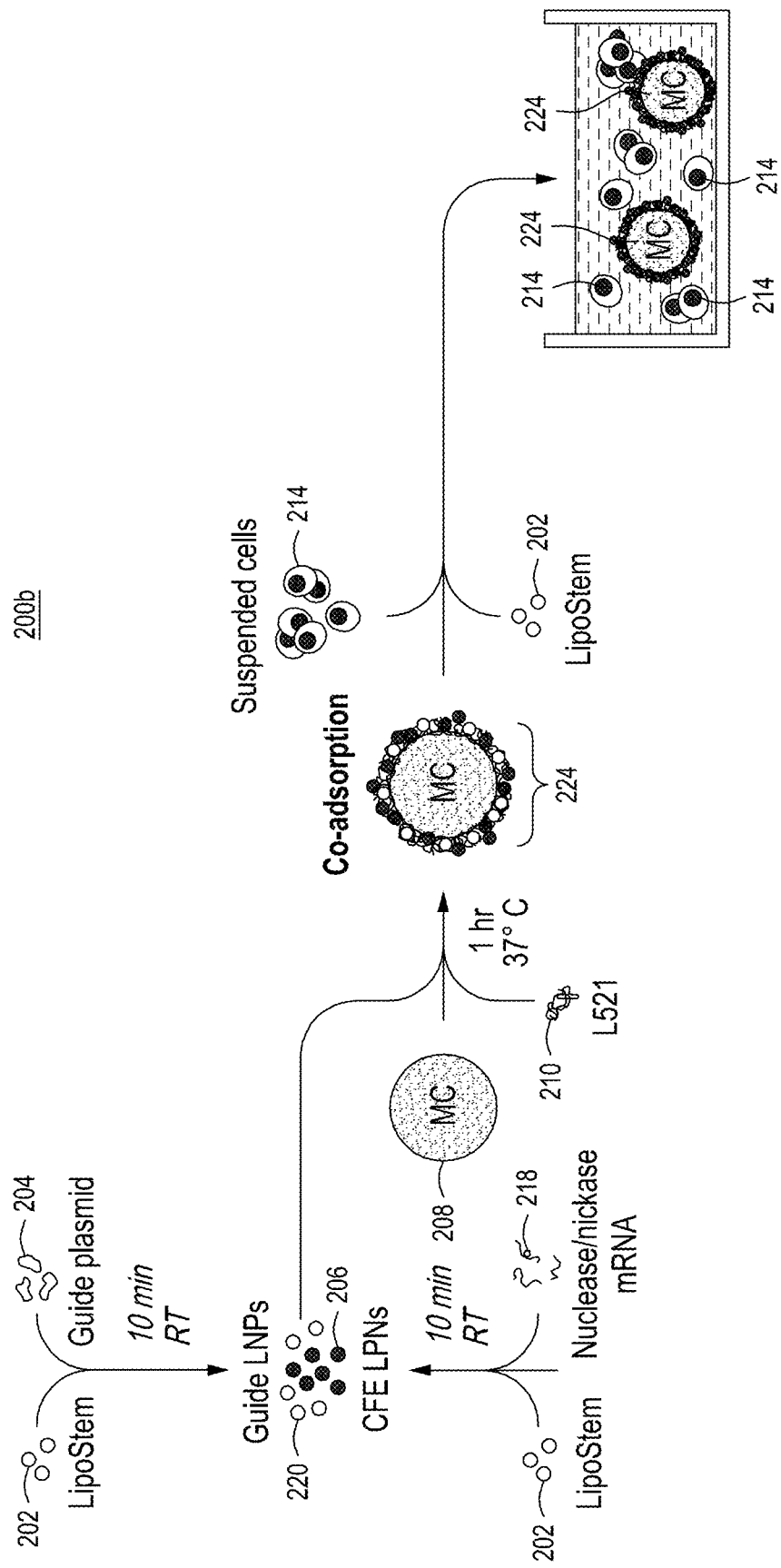
FIG. 2B depicts an alternative workflow employing microcarrier-partitioned delivery for editing cells.

FIGS. 2A and 2B depict alternative methods for populating microcarriers with a lipofectamine/nucleic acid payload and cells. In the method 200*a* shown in FIG. 2A at top left, lipofectamine 202 and guide plasmid payloads 204 are combined and guide LNPs (lipofectamine nucleic acid payloads) 206 are formed in solution. In parallel, microcarriers 208 ("MCs") are combined with a coating such as laminin 521 210 to foster adsorption and cell attachment. The laminin 521-coated microcarriers are then combined with the guide LNPs 206 to form partially-loaded microcarriers 212. The processes of forming RBMCs (i.e., the partially-loaded microcarriers 212 comprising the guide LNPs 206) to this point are typically performed off-instrument. In parallel and typically off-instrument, nuclease or nickase LNPs 220 are formed by combining lipofectamine 202 and nuclease or nickase mRNA 218. The nuclease or nickase LNPs 220 are combined with the partially-loaded microcarriers 212 and adsorb onto the partially-loaded microcarriers 212 to form fully-loaded RBMCs 222 comprising both the guide LNPs 206 and the nuclease or nickase LNPs 220. At this point, the stem cells 214 have been grown and passaged in the bioreactor and cell corral several to many times. The cells 214 populate the fully-loaded RBMCs 222, where the cells 214 then take up (i.e., are transfected by) the guide LNPs 206 and the nuclease or nickase LNPs 220, a process that may take several hours up to several days. At the end of the transfection process, transfected stem cells reside on the surface of the fully-loaded microcarriers 222.

As an alternative to the method 200*a* shown in FIG. 2A, FIG. 2B depicts method 200*b* which features simultaneous adsorption of the guide LNPs and the nuclease/nickase LNPs. Again, lipofectamine 202 and guide plasmid payloads 204 are combined where guide LNPs (lipofectamine nucleic acid payloads) 206 are formed in solution. In parallel, nuclease or nickase LNPs 220 are formed by combining lipofectamine 202 and nuclease or nickase mRNA 218. Also in parallel, microcarriers 108 are combined with a coating such as laminin 521 210 to foster adsorption and cell attachment. The laminin 521-coated microcarriers are simultaneously combined with both the guide LNPs 206 and the nuclease or nickase LNPs 220 to form fully-loaded microcarriers 224 where both the guide LNPs 206 and the nuclease or nickase LNPs 220 co-adsorb onto the surface of the laminin-coated microcarriers. The processes of forming RBMCs (i.e., the fully-loaded microcarriers 224 comprising both the guide LNPs 206 and the nuclease or nickase LNPs 220) to this point are typically performed off-instrument.

At this point, the fully-loaded microcarriers 224 comprising the guide LNPs 206 and the nuclease or nickase LNPs 220 are added to medium in the bioreactor comprising the stem cells 214 to be transfected, optionally with additional lipofect reagent 202. The stem cells 214 have been grown and passaged in the bioreactor and cell corral one to many times. The cells 214 populate the fully-loaded RBMCs 224, where the cells 214 then take up (i.e., are transfected by) the guide LNPs 206 and the nuclease or nickase LNPs 220, a process that may take several hours up to several days. At the end of the transfection process, transfected stem cells reside on the surface of the fully-loaded microcarriers 224. In these exemplary methods, nuclease or nickase fusion mRNAs are used to form the nuclease/nickase LNPs; however, the nuclease or nickase enzymes may be loaded on to form LNPs, or gRNAs and nuclease or nickase enzymes may be loaded in the form of RNPS on the LNPs.

Figure 3A:
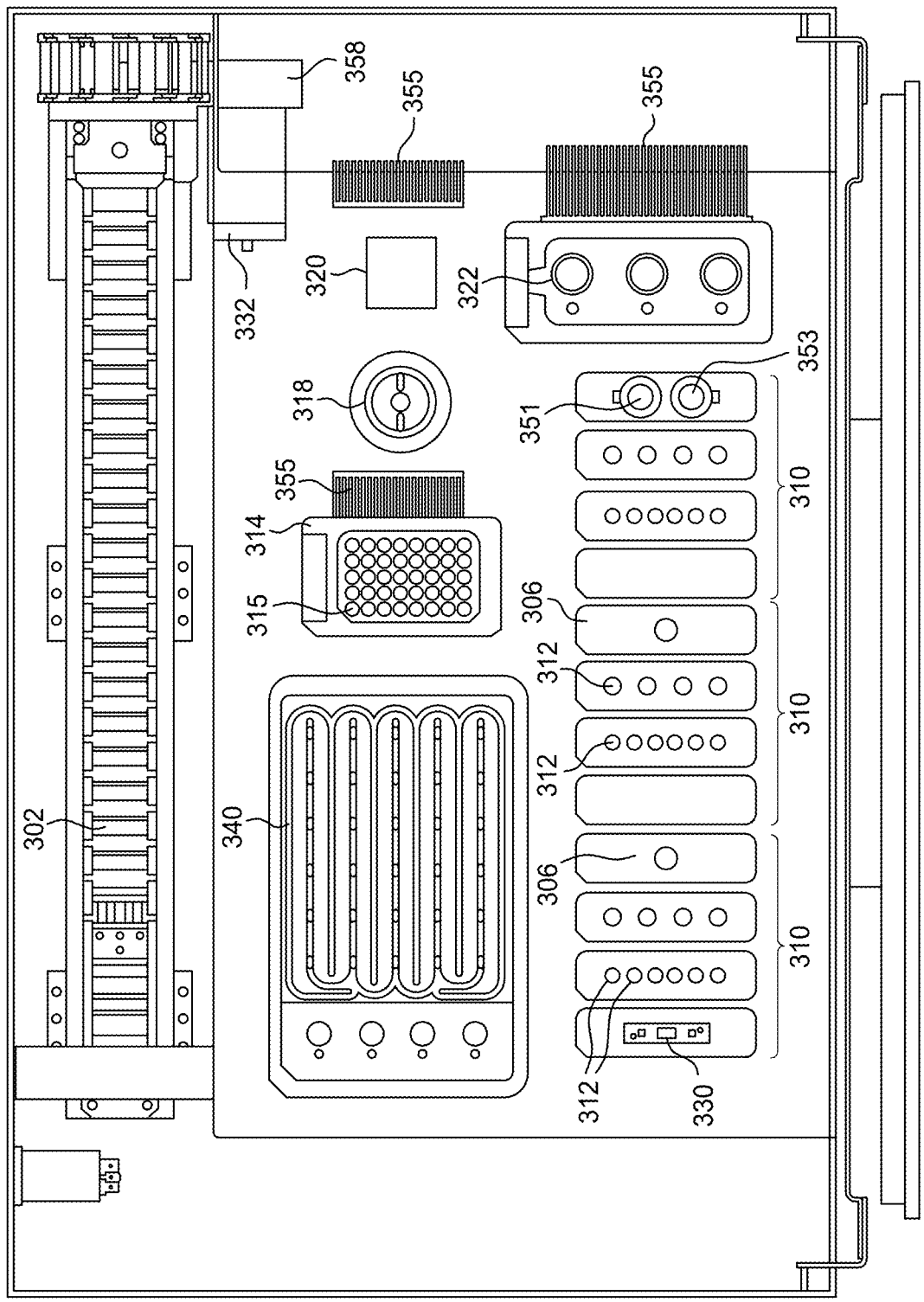
FIGS. 3A-3C illustrate different views of an exemplary automated multi-module cell processing instrument for performing nucleic acid-guided nuclease editing, according to embodiments of the present disclosure.

Automated Cell Editing Instruments and Modules to Perform Nucleic Acid-Guided Nuclease Editing in Cells One Embodiment of an Automated Cell Editing Instrument FIG. 3A depicts an exemplary automated multi-module cell processing instrument 100 to, e.g., perform targeted gene editing of live cells. The instrument 100, for example, may be and preferably is designed as a stand-alone benchtop instrument for use within a laboratory environment. The instrument 100 may incorporate a mixture of reusable and disposable components for performing the various integrated processes in conducting automated genome cleavage and/or editing in cells without human intervention. Illustrated in FIG. 3A is a gantry 102, providing an automated mechanical motion system (actuator) (not shown) that supplies XYZ axis motion control to, e.g., an automated (i.e., robotic) liquid handling system 158 including, e.g., an air displacement pipettor 132 which allows for cell processing among multiple modules without human intervention. In some automated multi-module cell processing instruments, the air displacement pipettor 132 is moved by gantry 102 and the various modules and reagent cartridges remain stationary; however, in other embodiments, the liquid handling system 158 may stay stationary while the various modules and reagent cartridges are moved. Also included in the automated multi-module cell processing instrument 100 are reagent cartridges 110 (see, U.S. Pat. No. 10,376,889; 10,406,525; 10,478,822; 10,576,474; 10,639,637; 10,738, 271; and 10,799,868) comprising reservoirs 112 and transformation module 130 (e.g., a flow-through electroporation device as described in U.S. Pat. No. 10,435,713; 10,443,074; and 10,851,389), as well as wash reservoirs 106, cell input reservoir 151 and cell output reservoir 153. The wash reservoirs 106 may be configured to accommodate large tubes, for example, wash solutions, or solutions that are used often throughout an iterative process. Although two of the reagent cartridges 110 comprise a wash reservoir 106 in FIG. 3A, the wash reservoirs instead could be included in a wash cartridge where the reagent and wash cartridges are separate cartridges. In such a case, the reagent cartridge and wash cartridge may be identical except for the consumables (reagents or other components contained within the various inserts) inserted therein.

In some implementations, the reagent cartridges 110 are disposable kits comprising reagents and cells for use in the automated multi-module cell processing/editing instrument 100. For example, a user may open and position each of the reagent cartridges 110 comprising various desired inserts and reagents within the chassis of the automated multi-module cell editing instrument 100 prior to activating cell processing. Further, each of the reagent cartridges 110 may be inserted into receptacles in the chassis having different temperature zones appropriate for the reagents contained therein.

Also illustrated in FIG. 3A is the robotic liquid handling system 158 including the gantry 102 and air displacement pipettor 132. In some examples, the robotic handling system 158 may include an automated liquid handling system such as those manufactured by Tecan Group Ltd. of Mannedorf, Switzerland, Hamilton Company of Reno, NV (see, e.g., WO2018015544A1), or Beckman Coulter, Inc. of Fort Collins, CO. (see, e.g., US20160018427A1). Pipette tips 115 may be provided in a pipette transfer tip supply 114 for use with the air displacement pipettor 132. The robotic liquid handling system allows for the transfer of liquids between modules without human intervention.

Inserts or components of the reagent cartridges 110, in some implementations, are marked with machine-readable indicia (not shown), such as bar codes, for recognition by the robotic handling system 158. For example, the robotic liquid handling system 158 may scan one or more inserts within each of the reagent cartridges 110 to confirm contents. In other implementations, machine-readable indicia may be marked upon each reagent cartridge 110, and a processing system (not shown, but see element 137 of FIG. 3B) of the automated multi-module cell editing instrument 100 may identify a stored materials map based upon the machine-readable indicia. In the embodiment illustrated in FIG. 3A, a cell growth module comprises a cell growth vial 118 (for details, see U.S. Pat. No. 10,435,662; 10,433,031; 10,590, 375; 10,717,959; and 10,883,095). Additionally seen is a tangential flow filtration (TFF) module 122 (for details, see U.S. Ser. Nos. 16/516,701 and 16/798,302). Also illustrated as part of the automated multi-module cell processing instrument 100 of FIG. 3A is a singulation module 140 (e.g., a solid wall isolation, incubation and normalization device (SWIIN device) is shown here and described in detail in U.S. Pat. No. 10,533,152; 10,633,626; 10,633,627; 10,647,958; 10,723,995; 10,801,008; 10,851,339; 10,954,485; 10,532, 324; 10,625,212; 10,774,462; and 10,835,869), served by, e.g., robotic liquid handing system 158 and air displacement pipettor 132. Additionally seen is a selection module 120 which may employ magnet separation. Also note the placement of three heatsinks 155.

Figure 3B:
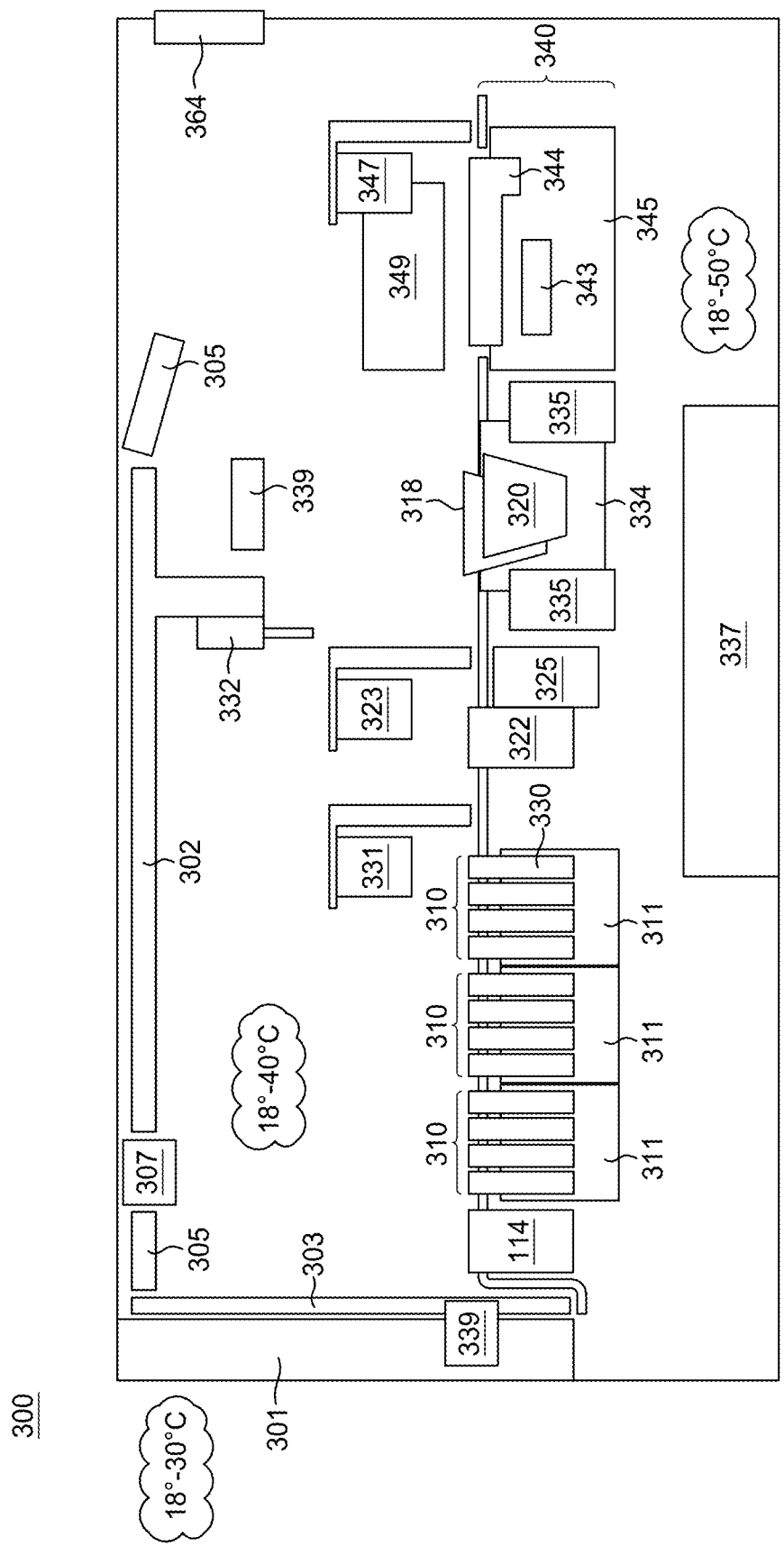

FIG. 3B is a simplified representation of the contents of the exemplary multi-module cell processing instrument 100 depicted in FIG. 3A. Cartridge-based source materials (such as in reagent cartridges 110), for example, may be positioned in designated areas on a deck of the instrument 100 for access by an air displacement pipettor 132. The deck of the multi-module cell processing instrument 100 may include a protection sink (not shown) such that contaminants spilling, dripping, or overflowing from any of the modules of the instrument 100 are contained within a lip of the protection sink. Also seen are reagent cartridges 110, which are shown disposed with thermal assemblies 111 which can create temperature zones appropriate for different reagents in different regions. Note that one of the reagent cartridges also comprises a flow-through electroporation device 130 (FTEP), served by FTEP interface (e.g., manifold arm) and actuator 131. Also seen is TFF module 122 with adjacent thermal assembly 125, where the TFF module is served by TFF interface (e.g., manifold arm) and actuator 123. Thermal assemblies 125, 135, and 145 encompass thermal electric devices such as Peltier devices, as well as heatsinks, fans and coolers. The rotating growth vial 118 is within a growth module 134, where the growth module is served by two thermal assemblies 135. A selection module is seen at 120. Also seen is the SWIIN module 140, comprising a SWIIN cartridge 144, where the SWIIN module also comprises a thermal assembly 145, illumination 143 (in this embodiment, backlighting), evaporation and condensation control 149, and where the SWIIN module is served by SWIIN interface (e.g., manifold arm) and actuator 147. Also seen in this view is touch screen display 101, display actuator 103, illumination 105 (one on either side of multi-module cell processing instrument 100), and cameras 139 (one camera on either side of multi-module cell processing instrument 100). Finally, element 137 comprises electronics, such as a processor, circuit control boards, high-voltage amplifiers, power supplies, and power entry; as well as pneumatics, such as pumps, valves and sensors.

Figure 3C:
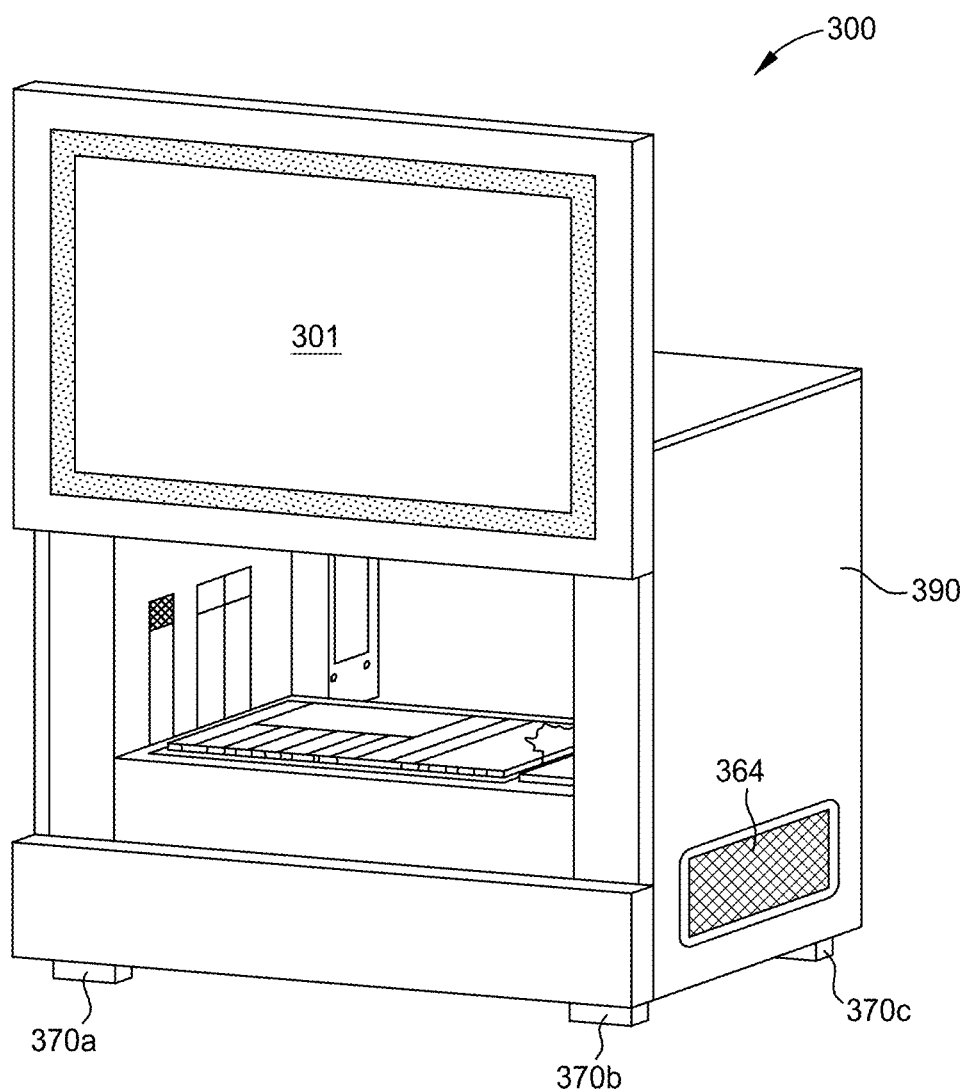

FIG. 3C illustrates a front perspective view of multi-module cell processing instrument 100 for use in as a benchtop version of the automated multi-module cell editing instrument 100. For example, a chassis 190 may have a width of about 24-48 inches, a height of about 24-48 inches and a depth of about 24-48 inches. Chassis 190 may be and preferably is designed to hold all modules and disposable supplies used in automated cell processing and to perform all processes required without human intervention; that is, chassis 190 is configured to provide an integrated, stand-alone automated multi-module cell processing instrument. As illustrated in FIG. 3C, chassis 190 includes touch screen display 101, cooling grate 164, which allows for air flow via an internal fan (not shown). The touch screen display provides information to a user regarding the processing status of the automated multi-module cell editing instrument 100 and accepts inputs from the user for conducting the cell processing. In this embodiment, the chassis 190 is lifted by adjustable feet 170*a*, 170*b*, 170*c* and 170*d* (feet 170*a*-170*c* are shown in this FIG. 3C). Adjustable feet 170*a*-170*d*, for example, allow for additional air flow beneath the chassis 190.

Inside the chassis 190, in some implementations, will be most or all of the components described in relation to FIGS. 3A and 3B, including the robotic liquid handling system disposed along a gantry, reagent cartridges 110 including a flow-through electroporation device, a rotating growth vial 118 in a cell growth module 134, a tangential flow filtration module 122, a SWIIN module 140 as well as interfaces and actuators for the various modules. In addition, chassis 190 houses control circuitry, liquid handling tubes, air pump controls, valves, sensors, thermal assemblies (e.g., heating and cooling units) and other control mechanisms. For examples of multi-module cell editing instruments, see U.S. Pat. No. 10,253,316; 10,329,559; 10,323,242; 10,421,959; 10,465,185; 10,519,437; 10,584,333; 10,584,334; 10,647, 982; 10,689,645; 10,738,301; 10,738,663; 10,947,532; 10,894,958; 10,954,512; and 11,034,953, all of which are herein incorporated by reference in their entirety.

Alternative Embodiment of an Automated Cell Editing Instrument

A bioreactor may be used to grow cells—in particular mammalian cells—off-instrument or to allow for cell growth and recovery on-instrument; e.g., as one module of a multi-module fully-automated closed instrument. Further, the bioreactor supports cell selection/enrichment, via expressed antibiotic markers in the growth process or via expressed antibodies coupled to magnetic beads and a magnet associated with the bioreactor. There are many bioreactors known in the art, including those described in, e.g., WO 2019/046766; 10,699,519; 10,633,625; 10,577,576; 10,294,447; 10,240,117; 10,179,898; 10,370,629; and 9,175,259; and those available from Lonza Group Ltd. (Basel, Switzerland); Miltenyi Biotec (Bergisch Gladbach, Germany), Terumo BCT (Lakewood, CO) and Sartorius GmbH (Gottingen, Germany).

FIG. 4A shows one embodiment of a bioreactor assembly 400 suitable for cell growth, transfection, and editing as one component of an automated multi-module cell processing instrument. Unlike most bioreactors that are used to support fermentation or other processes with an eye to harvesting the products produced by organisms grown in the bioreactor, the present bioreactor (and the processes performed therein) is configured to grow cells, monitor cell growth (via, e.g., optical means or capacitance), passage cells, select cells, transfect cells, and support the growth and harvesting of edited cells. Bioreactor assembly 400 comprises cell growth vessel 401 comprising a main body 404 with a lid assembly 402 comprising ports 408, including a motor integration port 410 configured to accommodate a motor to drive impeller 406 via impeller shaft 452. The tapered shape of main body 404 of the growth vessel 401 along with, in some embodiments, dual impellers allows for working with a larger dynamic range of volumes, such as, e.g., up to 500 ml and as low as 100 ml for rapid sedimentation of the microcarriers.

Bioreactor assembly 400 further comprises bioreactor stand assembly 403 comprising a main body 412 and growth vessel holder 414 comprising a heat jacket or other heating means (not shown) into which the main body 404 of growth vessel 401 is disposed in operation. The main body 404 of growth vessel 401 is biocompatible and preferably transparent—in some embodiments, in the UV and IR range as well as the visible spectrum—so that the growing cells can be visualized by, e.g., cameras or sensors integrated into lid assembly 402 or through viewing apertures or slots 446 in the main body 412 of bioreactor stand assembly 403. Camera mounts are shown at 444.

Bioreactor assembly 400 supports growth of cells from a 500,000 cell input to a 10 billion cell output, or from a 1 million cell input to a 25 billion cell output, or from a 5 million cell input to a 50 billion cell output or combinations of these ranges depending on, e.g., the size of main body 404 of growth vessel 401, the medium used to grow the cells, the type and size and number of microcarriers used for growth (if microcarriers are used), and whether the cells are adherent or non-adherent. The bioreactor that comprises assembly 400 supports growth of both adherent and non-adherent cells, wherein adherent cells are typically grown of microcarriers as described in detail in U.S. Ser. No. 17/237,747, filed 24 Apr. 2021. Alternatively, another option for growing mammalian cells in the bioreactor described herein is growing single cells in suspension using a specialized medium such as that developed by ACCELLTA™ (Haifa, Israel). Cells grown in this medium must be adapted to this process over many cell passages; however, once adapted the cells can be grown to a density of >40 million cells/ml and expanded 50-100× in approximately a week, depending on cell type.

Main body 404 of growth vessel 401 preferably is manufactured by injection molding, as is, in some embodiments, impeller 406 and the impeller shaft 452. Impeller 406 also may be fabricated from stainless steel, metal, plastics or the polymers listed infra. Injection molding allows for flexibility in size and configuration and also allows for, e.g., volume markings to be added to the main body 404 of growth vessel 401. Additionally, material from which the main body 404 of growth vessel 401 is fabricated should be able to be cooled to about 4° C. or lower and heated to about 55° C. or higher to accommodate cell growth. Further, the material that is used to fabricate the vial preferably is able to withstand temperatures up to 55° C. without deformation. Suitable materials for main body 404 of growth vessel 401 include cyclic olefin copolymer (COC), glass, polyvinyl chloride, polyethylene, polyetheretherketone (PEEK), polypropylene, polycarbonate, poly(methyl methacrylate (PMMA)), polysulfone, poly(dimethylsiloxane), cyclo-olefin polymer (COP), and co-polymers of these and other polymers. Preferred materials include polypropylene, polycarbonate, or polystyrene. The material used for fabrication may depend on the cell type to be grown, transfected and edited, and be conducive to growth of both adherent and non-adherent cells and workflows involving microcarrier-based transfection. The main body 404 of growth vessel 401 may be reusable or, alternatively, may be manufactured and configured for a single use. In one embodiment, main body 404 of growth vessel 401 may support cell culture volumes of 25 ml to 500 ml, but may be scaled up to support cell culture volumes of up to 3 L.

The bioreactor stand assembly comprises a stand or frame 450 and a main body 412 that holds the growth vessel 401 during operation. The stand/frame 450 and main body 412 are fabricated from stainless steel, other metals, or polymer/plastics. The bioreactor stand assembly main body further comprises a heat jacket (not seen in FIG. 4A) to maintain the growth vessel main body 404—and thus the cell culture—at a desired temperature. Additionally, the stand assembly can host a set of sensors and cameras (camera mounts are shown at 444) to monitor cell culture.

Figure 4B:
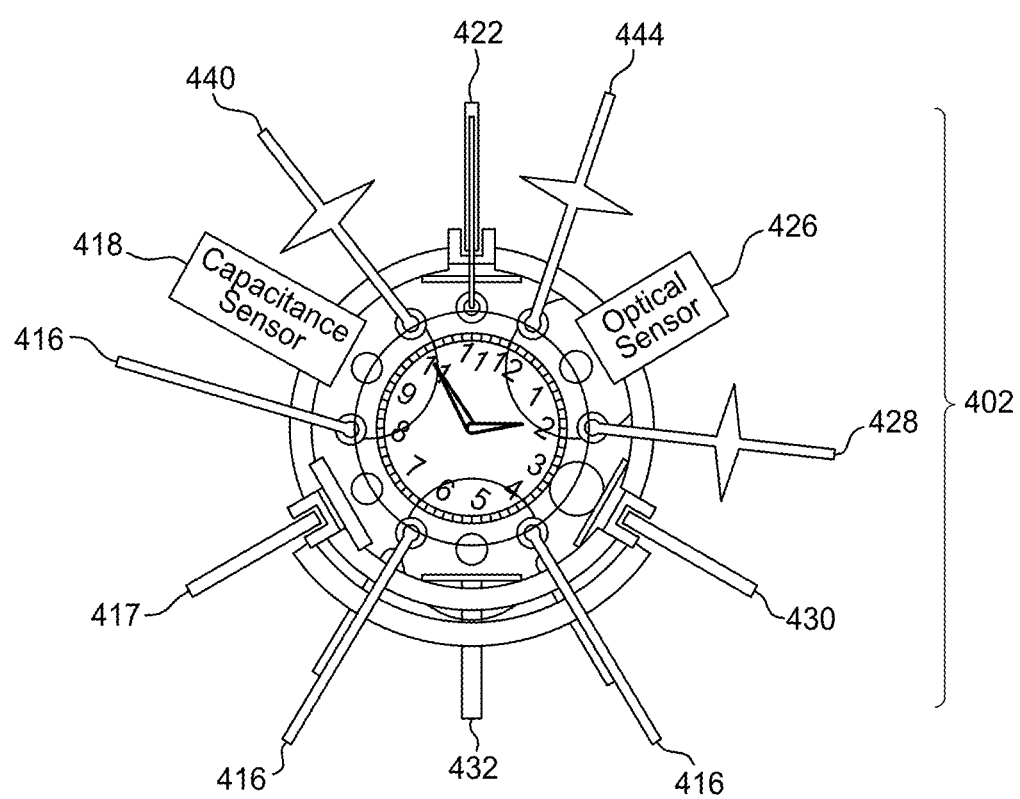

FIG. 4B depicts a top-down view of one embodiment of vessel lid assembly 402. Growth vessel lid assembly 402 is configured to be air-tight, providing a sealed, sterile environment for cell growth, transfection and editing as well as to provide biosafety in a closed system. Vessel lid assembly 402 and the main body of growth vessel can be reversibly sealed via fasteners such as screws, or permanently sealed using biocompatible glues or ultrasonic welding. Vessel lid assembly 402 in some embodiments is fabricated from stainless steel such as S316L stainless steel but may also be fabricated from metals, other polymers (such as those listed supra) or plastics. As seen in this FIG. 4B—as well as in FIG. 4A—vessel lid assembly 402 comprises a number of different ports to accommodate liquid addition and removal; gas addition and removal; for insertion of sensors to monitor culture parameters (described in more detail infra); to accommodate one or more cameras or other optical sensors; to provide access to the main body 404 of growth vessel 401 by, e.g., a liquid handling device; and to accommodate a motor for motor integration to drive one or more impellers 406. Exemplary ports depicted in FIG. 4B include three liquid-in ports 416 (at 4 o'clock, 6 o'clock and 8 o'clock); two self-sealing ports 417, 430 (at 3 o'clock and at 7 o'clock) to provide access to the main body 404 of growth vessel 401; one liquid-out port 422 (at 11 o'clock); a capacitance sensor 418 (at 9 o'clock); one "gas in" port 424 (at 12 o'clock); one "gas out" port 420 (at 10 o'clock); an optical sensor 426 (at 1 o'clock); a rupture disc 428 at 2 o'clock; and (a temperature probe 432 (at 5 o'clock).

The ports shown in vessel lid assembly 402 in this FIG. 4B are exemplary only and it should be apparent to one of ordinary skill in the art given the present disclosure that, e.g., a single liquid-in port 416 could be used to accommodate addition of all liquids to the cell culture rather than having a liquid-in port for each different liquid added to the cell culture. Further, any liquid-in port may serve as both a liquid-in port and a liquid-out port. Similarly, there may be more than one gas-in port 424, such as one for each gas, e.g., 02, $CO_2$ that may be added. In addition, although a temperature probe 432 is shown, a temperature probe alternatively may be located on the outside of vessel holder 414 of bioreactor stand assembly 403 separate from or integrated into heater jacket (not seen in this FIG. 4B). A self-sealing port 430, if present, allows access to the main body 404 of growth vessel 401 for, e.g., a pipette, syringe, or other liquid delivery system via a gantry (not shown). As shown in FIG. 4A, additionally there may be a motor integration port 410 to drive the impeller(s), although other configurations of growth vessel 401 may alternatively integrate the motor drive at the bottom of the main body 404 of growth vessel 401. Growth vessel lid assembly 402 may also comprise a camera port for viewing and monitoring the cells.

Additional sensors include those that detect dissolved $O_2$ concentration, dissolved $CO_2$ concentration, culture pH, lactate concentration, glucose concentration, biomass, and optical density. The sensors may use optical (e.g., fluorescence detection), electrochemical, or capacitance sensing and either be reusable or configured and fabricated for single-use. Sensors appropriate for use in the bioreactor are available from Omega Engineering (Norwalk CT); PreSens Precision Sensing (Regensburg, Germany); C-CIT Sensors AG (Waedenswil, Switzerland), and ABER Instruments Ltd. (Alexandria, VA). In one embodiment, optical density is measured using a reflective optical density sensor to facilitate sterilization, improve dynamic range and simplify mechanical assembly.

The rupture disc, if present, provides safety in a pressurized environment, and is programmed to rupture if a threshold pressure is exceeded in growth vessel. If the cell culture in the growth vessel is a culture of adherent cells, microcarriers may be used as described in U.S. Ser. No. 17/237, 747, filed 24 Apr. 2021. In such an instance, the liquid-out port may comprise a filter such as a stainless steel or plastic (e.g., polyvinylidene difluoride (PVDF), nylon, polypropylene, polybutylene, acetal, polyethylene, or polyamide) filter or frit to prevent microcarriers from being drawn out of the culture during, e.g., medium exchange, but to allow dead cells to be withdrawn from the vessel. Additionally, a liquid port may comprise a filter sipper to allow cells that have been dissociated from microcarriers to be drawn into the cell corral while leaving spent microcarriers in main body 404 of growth vessel 401. The microcarriers used for initial cell growth can be nanoporous (where pore sizes are typically <20 nm in size), microporous (with pores between >20 nm to <1 μm in size), or macroporous (with pores between >1 μm in size, e.g. 20 μm) and the microcarriers are typically 50-200 μm in diameter; thus the pore size of the filter or frit in the liquid-out port will differ depending on microcarrier size.

The microcarriers used for cell growth depend on cell type and desired cell numbers, and typically include a coating of a natural or synthetic extracellular matrix or cell adhesion promoters (e.g., antibodies to cell surface proteins or poly-L-lysine) to promote cell growth and adherence. Microcarriers for cell culture are widely commercially available from, e.g., Millipore Sigma, (St. Louis, MO, USA); ThermoFisher Scientific (Waltham, MA, USA); Pall Corp. (Port Washington, NY, USA); GE Life Sciences (Marlborough, MA, USA); and Corning Life Sciences (Tewkesbury, MA, USA). As for the extracellular matrix, natural matrices include collagen, fibrin and vitronectin (available, e.g., from ESBio, Alameda, CA, USA), and synthetic matrices include MATRIGEL® (Corning Life Sciences, Tewkesbury, MA, USA), GELTREX™ (ThermoFisher Scientific, Waltham, MA, USA), CULTREX® (Trevigen, Gaithersburg, MD, USA), biomemetic hydrogels available from Cellendes (Tubingen, Germany); and tissue-specific extracellular matrices available from Xylyx (Brooklyn, NY, USA); further, denovoMatrix (Dresden, Germany) offers screenMATRIX™, a tool that facilitates rapid testing of a large variety of cell microenvironments (e.g., extracellular matrices) for optimizing growth of the cells of interest.

Figure 4C:
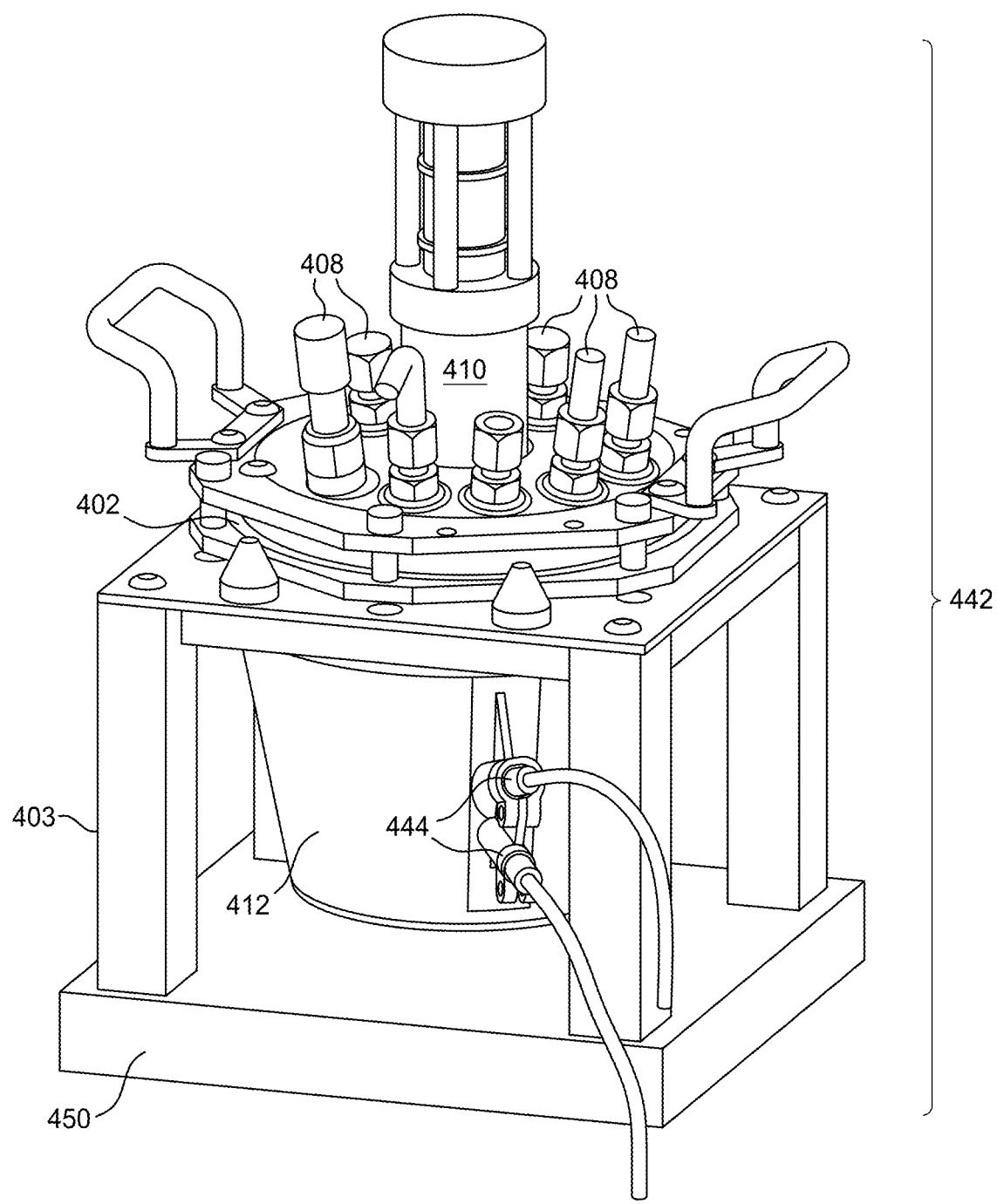

FIG. 4C is a side perspective view of the assembled bioreactor 442 without sensors mounted in ports 408. Seen are vessel lid assembly 402, bioreactor stand assembly 403, bioreactor stand main body 412 into which the main body of growth vessel 401 (not seen in this FIG. 4C) is inserted. Also present are two camera mounts 444, a motor integration port 410, and stand or frame 450.

Figure 4D:
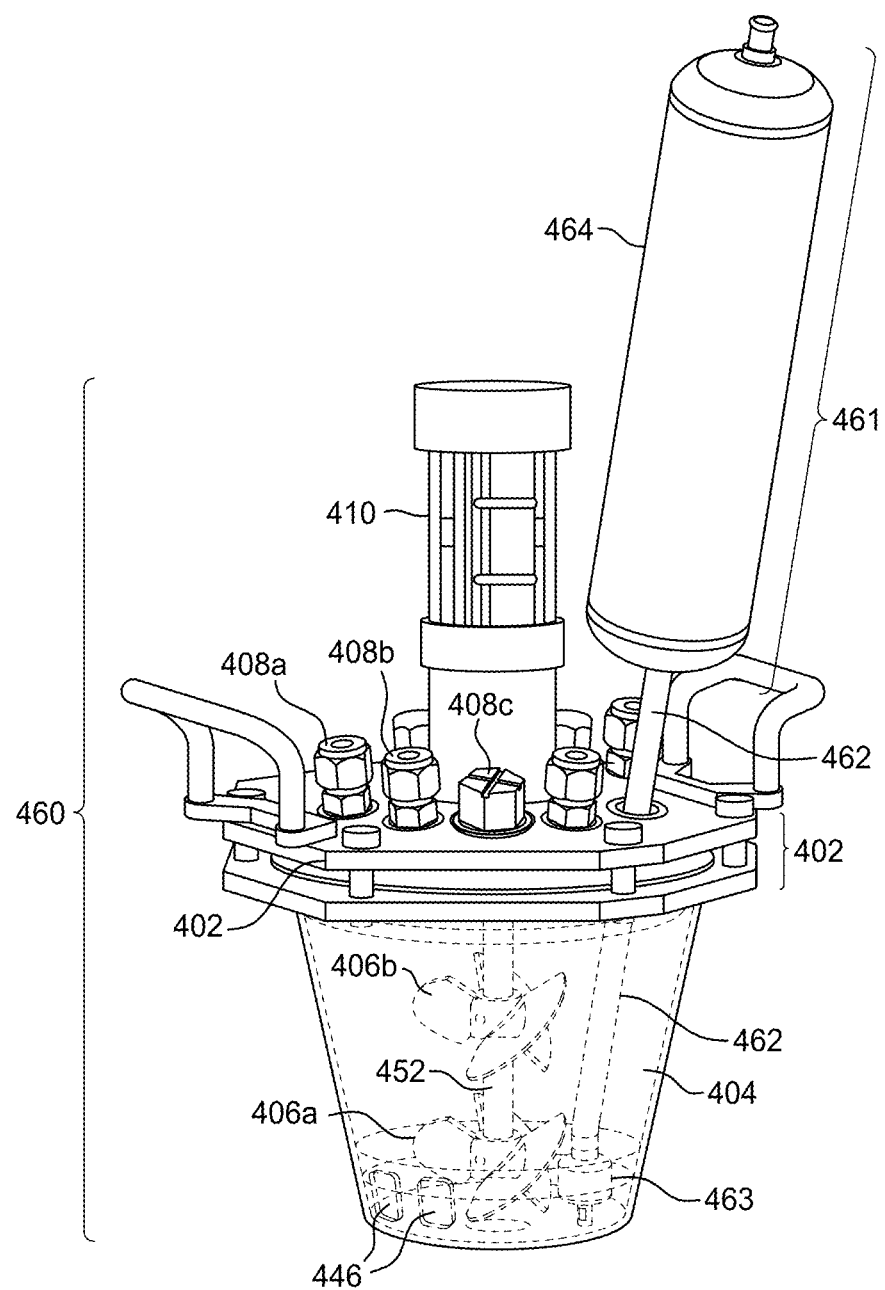
FIGS. 4D and 4E depict an exemplary integrated instrument for growing and transfecting cells.

FIG. 4D shows the embodiment of a bioreactor/cell corral assembly 460, comprising the bioreactor assembly 400 for cell growth, transfection, and editing described in FIG. 4A and further comprising a cell corral 461. Bioreactor assembly 400 comprises a growth vessel 401 (not labeled in this FIG. 4D) comprising tapered a main body 404 with a lid assembly 402 comprising ports 408 (here, 408a, 408b, 408c), including a motor integration port 410 driving impeller 406 via impeller shaft 452, as well as two viewing ports 446. Cell corral 461 comprises a main body 464, and end caps 473, where the end cap proximal the bioreactor assembly 400 is coupled to a filter sipper 462 comprising a filter portion 463 disposed within the main body 404 of the bioreactor assembly 400. The filter sipper is disposed within the main body 404 of the bioreactor assembly 400 but does not reach to the bottom surface of the bioreactor assembly 400 to leave a "dead volume" for spent microcarriers to settle while cells are removed from the growth vessel 401 into the cell corral 461. The cell corral may or may not comprise a temperature or $CO_2$ probe, and may or may not be enclosed within an insulated jacket.

The cell corral 461, like the main body 404 of growth vessel 401 is fabricated from any biocompatible material such as polycarbonate, cyclic olefin copolymer (COC), glass, polyvinyl chloride, polyethylene, polyetheretherketone (PEEK), polypropylene, poly(methyl methacrylate (PMMA)), polysulfone, poly(dimethylsiloxane), cyclo-olefin polymer (COP), and co-polymers of these and other polymers. Likewise, the end caps 373 of the cell corral are fabricated from a biocompatible material such as polycarbonate, cyclic olefin copolymer (COC), glass, polyvinyl chloride, polyethylene, polyetheretherketone (PEEK), polypropylene, poly(methyl methacrylate (PMMA)), polysulfone, poly(dimethylsiloxane), cyclo-olefin polymer (COP), and co-polymers of these and other polymers. The cell corral may be coupled to or integrated with one or more devices, such as a flow cell where an aliquot of the cell culture can be counted. Additionally, the cell corral may comprise additional liquid ports for adding medium, other reagents, and/or fresh microcarriers to the cells in the cell corral. The volume of the main body 464 of the cell corral 461 may be from 25 to 3000 mL, or from 250 to 1000 mL, or from 450 to 500 mL.

In operation, the bioreactor/cell corral assembly 460 comprising the bioreactor assembly 400 and cell corral 461 grows, passages, transfects, and supports editing and further growth of mammalian cells (note, the bioreactor stand assembly is not shown in this FIG. 4D). Cells are transferred to the growth vessel 401 comprising medium and microcarriers. The cells are allowed to adhere to the microcarries. Approximately 2000,000 microcarriers (e.g., laminin-521 coated polystyrene with enhanced attachment surface treatment) are used for the initial culture of approximately 20 million cells to where there are approximately 50 cells per microcarrier. The cells are grown until there are approximately 500 cells per microcarrier. For medium exchange, the microcarriers comprising the cells are allowed to settle and spent medium is aspirated via a sipper filter, wherein the filter has a mesh small enough to exclude the microcarriers. The mesh size of the filter will depend on the size of the microcarriers and cells present but typically is from 50 to 500 µm, or from 70 to 200 µm, or from 80 to 110 µm. For passaging the cells, the microcarriers are allowed to settle and spent medium is removed from the growth vessel 401, and phosphobuffered saline or another wash agent is added to the growth vessel 401 to wash the cells on the microcarriers. Optionally, the microcarriers are allowed to settle once again, and some of the wash agent is removed. At this point, the cells are dissociated from the microcarriers. Dissociation may be accomplished by, e.g., bubbling gas or air through the wash agent in the growth vessel 401, by increasing the impeller speed and/or direction, by enzymatic action (via, e.g., trypsin), or by a combination of these methods. In one embodiment, a chemical agent such as the RelesR™ reagent (STEMCELL Technologies Canada INC., Vancouver, BC) is added to the microcarriers in the remaining wash agent for a period of time required to dissociate most of the cells from the microcarriers, such as from 1 to 60 minutes, or from 3 to 25 minutes, or from 5 to 10 minutes. Once enough time has passed to dissociate the cells, cell growth medium is added to the growth vessel 401 to stop the enzymatic reaction.

Once again, the now-spent microcarriers are allowed to settle to the bottom of the growth vessel 401 and the cells are aspirated through a filter sipper into the cell corral 461. The growth vessel 401 is configured to allow for a "dead volume" of 2 mL to 200 mL, or 6 mL to 50 mL, or 8 mL to 12 mL below which the filter sipper does not aspirate medium to ensure the settled spent microcarriers are not transported to the filter sipper during fluid exchanges. Once the cells are aspirated from the bioreactor vessel leaving the "dead volume" of medium and spent microcarriers, the spent microcarriers are aspirated through a non-filter sipper into waste. The spent microcarriers (and the bioreactor vessel) are diluted in phosphobuffered saline or other buffer one or more times, wherein the wash agent and spent microcarriers continue to be aspirated via the non-filter sipper leaving a clean bioreactor vessel. After washing, fresh microcarriers or RBMCs and fresh medium are dispensed into the bioreactor vessel and the cells in the cell corral are dispensed back into the bioreactor vessel for another round of passaging or for transfection and editing, respectively.

Figure 4E:
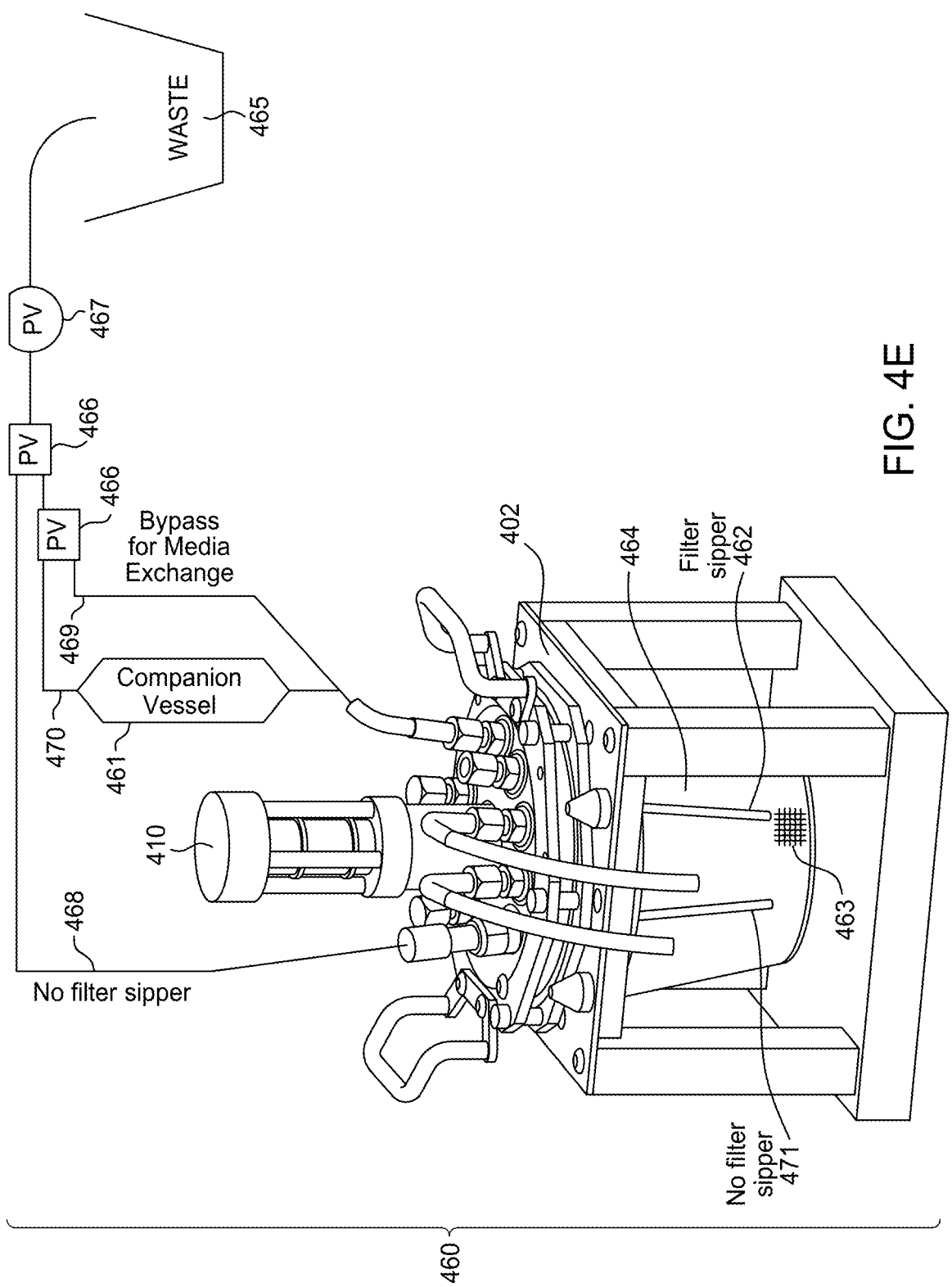

FIG. 4E depicts a bioreactor and bioreactor/cell corral assembly 460 comprising a growth vessel 401, with a main body 464, lid assembly 402 comprising a motor integration port 410, a filter sipper 462 comprising a filter 463 and a non-filter sipper 471, 468. Also seen is a cell corral 461, fluid line 468 from the cell corral through pinch valve 466, and a line 469 for medium exchange also connected to a pinch valve 466. The non-filter sipper 468 also runs through a pinch valve 466 to waste 465. Also seen is a peristaltic pump 467.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I: GFP to BFP Conversion Assay

A GFP to BFP reporter cell line was created using mammalian cells with a stably integrated genomic copy of the GFP gene (HEK293T-GFP). These cell lines enabled phenotypic detection of genomic edits of different classes by various different mechanisms, including flow cytometry, fluorescent cell imaging, and genotypic detection by sequencing of the genome-integrated GFP gene. Lack of editing, or perfect repair of cut events in the GFP gene, result in cells that remain GFP-positive. Cut events that are repaired by the Non-Homologous End-Joining (NHEJ) pathway often result in nucleotide insertion or deletion events (indels), resulting in frame-shift mutations in the coding sequence that cause loss of GFP gene expression and fluorescence. Cut events that are repaired by the Homology-Directed Repair (HDR) pathway using the GFP to BFP HDR donor as a repair template or by the use of CF editing cassettes, e.g., complementary CF editing cassettes, result in conversion of the cell fluorescence profile from that of GFP to that of BFP.

Example II: CREATE Fusion Editing—Proof of Concept MAD Nickase

CREATE fusion Editing (CFE) is a technique that uses a nucleic acid nickase fusion protein (e.g., MAD2019 nickase)

fused to a peptide with reverse transcriptase activity along with a nucleic acid encoding a gRNA comprising a region complementary to a target region of a nucleic acid in one or more cells, which comprises a mutation of at least one nucleotide relative to the target region in the one or more cells and a protospacer adjacent motif (PAM) mutation.

In a first design, a nickase enzyme derived from the MAD2007 nuclease (see, U.S. Pat. Nos. 9,982,279 and 10,337,028), e.g., Cas9 H840A nickase or MAD7 nickase (see, e.g., U.S. Ser. No. 16/837,212 and 17/084,522), was fused to an engineered reverse transcriptase (RT) on the C-terminus and cloned downstream of a CMV promoter. In this instance, the RT used was derived from Moloney Murine Leukemia Virus (M-MLV).

Cassettes with RNA guides were designed that were complementary to a single region proximal to the EGFP-to-BFP editing site. The gRNA was extended on the 3' end to include a region of 13 bp that included the TY-to-SH edit and a second region of 13 bp that is complementary to the nicked EGFP DNA sequence (e.g., forming a repair template). This allowed the nicked genomic DNA to anneal to the 3' end of the gRNA which can then be extended by the reverse transcriptase to incorporate the edit in the genome. A second cassette with a gRNA targets a region in the EGFP DNA sequence that is 86 bp upstream of the edit site. This cassette was designed such that it enables the nickase to cut the opposite strand relative to gRNA. Both of these gRNAs were cloned downstream of a U6 promoter. A poly-T sequence was also included that terminates the transcription of the gRNA.

The plasmids were transformed into NEB Stable E. coli (Ipswich, NY) and grown overnight in 25 mL LB cultures. The following day the plasmids were purified from E. coli using the Qiagen Midi Prep kit (Venlo, Netherlands). The purified plasmid was then RNase A (ThermoFisher, Waltham, MA) treated and re-purified using the DNA Clean and Concentrator kit (Zymo, Irvine, CA).

HEK293T-GFP cells were cultured in DMEM medium which was supplemented with 10% FBS and 1× Penicillin and Streptomycin. 100 ng of total DNA (50 ng of cassette plasmid and 50 ng of CFE plasmids) was mixed with 1 µl of PolyFect (Qiagen, Venlo, Netherlands) in 25 µl of OptiMEM in a 96 well plate. The complex was incubated for 10 minutes and then 20,000 HEK293T cells resuspended in 100 µl of DMEM were added to the mixture. The resulting mixture was then incubated for 80 hours at 37 C and 5% $CO_2$.

The cells were harvested from flat bottom 96 well plates using TrypLE Express reagent (ThermoFisher, Waltham, Mass) and transferred to v-bottom 96 well plate. The plate was then spun down at 500 g for 5 minutes. The TrypLE solution was then aspirated and the cell pellet was resuspended in FACS buffer (1×PBS, 1% FBS, 1 mM EDTA and 0.5% BSA). The GFP+, BFP+ and RFP+ cells were then analyzed on the Attune NxT flow cytometer and the data was analyzed on FlowJo software.

The RFP+BFP+ cells that were identified were indicative of the proportion of enriched cells that have undergone precise or imprecise editing process. BFP+ cells indicate cells that have undergone successful editing process and express BFP. The GFP-cells indicate cells that have been imprecisely edited, leading to disruption of the GFP open reading frame and loss of expression.

The effectiveness of CREATE fusion editing in GFP+ HEK293T cells was then tested. In the assay system devised, a successful precise edit resulted in a BFP+ cell whereas an imprecisely edited cells turned the cell both BFP and GFP negative. CREATE fusion cassettes in combination with CFE2.1 or CFE2.2 gave ~40-45% BFP+ cells indicating that almost half the cell population has undergone successful editing (data not shown). The GFP− cells are ~10% of the population. The use of a second nicking cassette, as described in Liu et al. (Nature, 576(7785):149-157 (2019)) did not increase the precision edit rate any further; in fact, it significantly increased the imprecisely edited, GFP-negative cell population and the editing rate was lower.

Previous literature has shown that double nicks on opposite strands (<90 bp away) do result in a double strand break which tend to be repaired via NHEJ resulting in imprecise insertions or deletions. Overall, the results indicated that CREATE rusion editing predominantly yielded precisely edited cells and the imprecisely edited cells proportion is much lower (data not shown).

An enrichment handle, specifically a fluorescent reporter (RFP) linked to nuclease expression was included in this experimentation as a proxy for cells receiving the editing machinery. When only the RFP-positive cells were analyzed (computational enrichment) after 3-4 cell divisions, up to 75% of the cells were BFP+ when tested with gRNA (data not shown), indicating uptake or expression-linked reporters can be used to enrich for a population of cells with higher rates of CREATE fusion-mediated gene editing. In fact, the combined use of CREATE Fusion Editing and the described enrichment methods resulted in a significantly improved rate of intended edits (data not shown).

Example III. CREATE Fusion Editing—Proof of Concept with Single gRNA/Cassette

CREATE fusion editing was carried out in mammalian cells using a single guide RNA covalently linked to a homology arm having an intended edit to the native sequence and an edit that disrupts nuclease cleavage at this site. Briefly, lentiviral vectors were produced using the following protocol: 1000 ng of Lentiviral transfer plasmid containing the CREATE Fusion cassettes along with 1500 ng of Lentiviral Packaging plasmids (ViraSafe Lentivirus Packaging System Cell BioLabs) were transfected into HEK293T cells using Lipofectamine LTX in 6-well plates. Media containing the lentivirus was collected 72 hrs post transfection. Two clones of a lentiviral CREATE fusion gRNA-HA design were chosen, and an empty lentiviral backbone was included as negative control.

The day before the transduction, 200,000 HEK293T cells were seeded in six well plates. Different volumes of CREATE lentivirus (10 to 1000 µl) were added to HEK293T cells in six well plates along with 10 µg/ml of Polybrene. 48 hours after transduction, media with 15 µg/ml of Blasticidin was added to the wells. Cells were maintained in selection for one week. Following selection, the well with lowest number of surviving cells was selected for future experiments (<5% cells)

The experimental constructs or wild-type SpCas9 were electroporated into HEK293T cells using the Neon Transfection System (Thermo Fisher Scientific, Waltham, MA). Briefly, 400 ng of total plasmid DNA was mixed with 100,000 cells in Buffer R in a total of 15 µl volume. The 10 µl Neon tip was used to electroporate cells using 2 pulses of 20 ms and 1150 v. Cells were analyzed on the flow cytometer 80 hrs post electroporation. Unenriched editing rates of up to 15% were achieved from single copy delivery of gRNA (data not shown).

When the editing was combined with computational selection of RFP+ cells, however, enriched editing rates of up to 30% were achieved from a single copy delivery gRNA. This enrichment via selection of cells receiving the editing machinery was shown to result in a 2-fold increase in precise, complete intended edits (data not shown). Two or more enrichment/delivery steps can also be used to achieve higher editing rates of CREATE Fusion Editing in an automated instrument, e.g., use of a module for cell handle enrichment and identification of cells having BFP expression. When the method enriched for cells that have higher gRNA expression levels, the editing rate was even further increased, and thus a growth and/or enrichment module of the instrument may include gRNA enrichment.

Example IV: Testing Nucleic Acid-Guided Nickase/Reverse Transcriptase Fusion Editing Using Dual CF Editing Cassettes The dual CF editing cassette nickase/RT fusion system was tested in a GFP-to-BFP assay to answer two questions. First, does the dual CF editing cassette nickase/RT fusion system perform better than a prime editing system (e.g., a system where a single gRNA is used to edit only one DNA strand of a target locus) and second, is the increase in editing rate for the dual CF editing cassette system more than the increase in the editing rate for a first cassette tested alone added to the increase in the editing rate for a second cassette tested alone?

Figure 5:
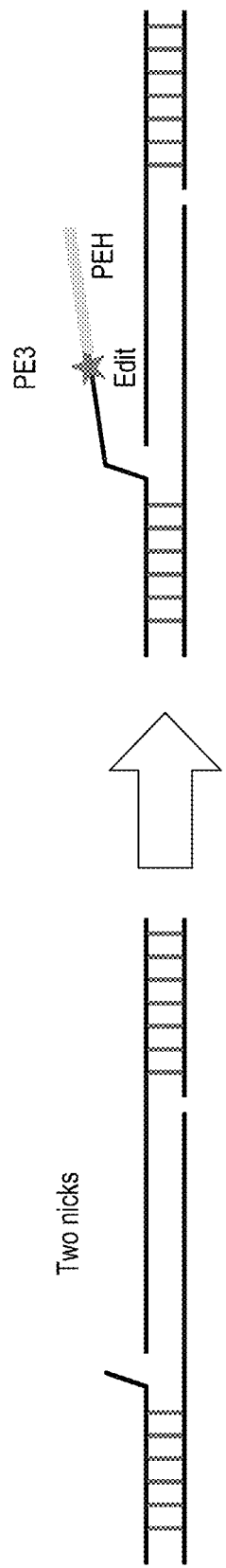
FIG. 5 is a simplified graphic depiction of the mechanism of a prior art prime fusion edit (see Anazalone, et al., Nature, https://doi.org/10.1038/s41586-019-1711-4 (2019)).

In relation to the first question, a prime editing system is shown in FIG. 5. In the prime editing system, a nickase-RT fusion is used to nick both strands of a target locus and a reverse transcriptase is used synthesize an edit replacement strand; however, only one gRNA is used to incorporate the edit rather than using two gRNAs to incorporate the edit on both DNA strands of the target locus. With only a single DNA strand in the target locus comprising the desired edit, there is a mis-match with the wildtype sequence of the opposite strand; that is, there is mis-annealing between the two DNA strands at the edit, which requires the cell's endogenous repair mechanisms to repair the edit in favor of the desired edit. The compositions and methods of the present disclosure were benchmarked against this prime editing system (see FIGS. 7-8).

Figure 6:
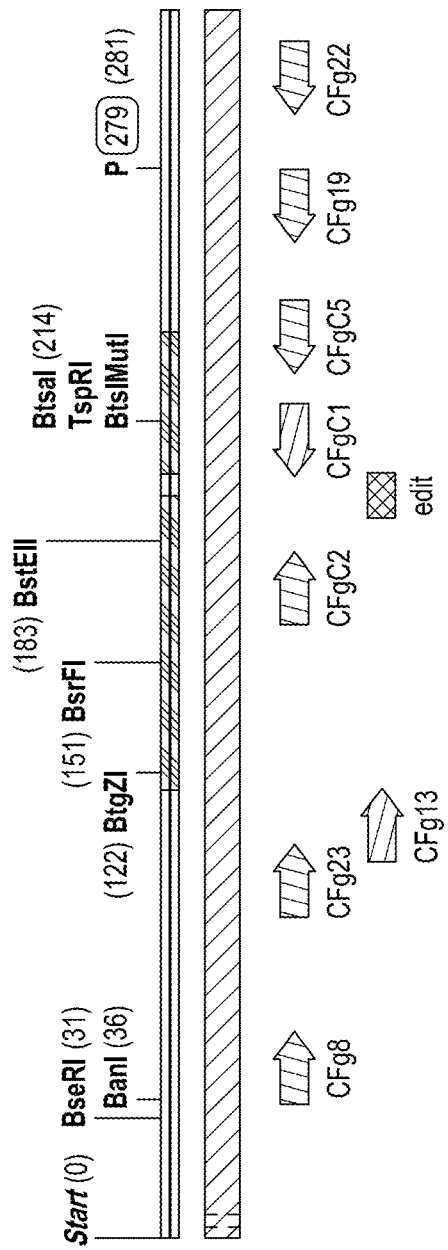
FIG. 6 is a map of various CFgRNAs used in a GFP-to-BFP assay system, as well as the position of the edit that converts GFP to BFP. The numbering system on the X-axis indicates the number of CFgRNA used, and following a dash, the post-edit homology used. For example, 13-8 is the 13$^{th}$ CFgRNA used, with a post-edit homology and 13-0 encodes nick to the edit, the edit, but not the post-edit homology. In some instances, gRNAs were transfected with no additional region to template reverse transcription. These gRNAs are denoted by "NoExt." For example, 13-NoExt, contains a CFgRNA spacer and scaffold, but no additional region that could be reverse transcribed by a reverse transcriptase.

FIG. 6 is a map of various CF editing cassettes ("CFg") used in a GFP-to-BFP assay system, i.e, CFg8, CFg23, CFg13, CFgC2, CFgC1, DFgC5, CFg19 and CFg22, as well as the position of the edit ("edit"). Positions of restriction endonuclease sites in the GFP gene are also noted.

FIG. 7 shows two bar graphs where the first bar graph (at left) demonstrates that editing rate is increased when utilizing a nickase-RT fusion enzyme and both a 19-8 CF editing cassette and a 13-8 CF editing cassette in the editing system as opposed to using only one of the cassettes in an editing system. In these experiments, 50 ng of the nickase-RT fusion enzyme was used and 25 ng of each CF editing cassette was used to transfect HEK293T cells. In cases where a single CF editing cassette is used, 50 ng of the single cassette was used to keep the concentration of cassettes consistent. RFP+ indicates a cell that has been transfected, and BFP+ indicates a cell that has been edited. The 19-8 CF editing cassette stands for the CFg19 cassette shown in FIG. 6 which has a post-edit homology length of 8 nucleotides. The 13-8 CF editing cassette stands for the CFg13 cassette shown in FIG. 6 which has a post-edit homology length of 8 nucleotides.

In the first bar graph, the left-most bar is the enriched editing rate of using a 13-8 CF editing cassette alone, approximately 8%. The second bar is the enriched editing rate of using a 19-8 CF editing cassette alone, approximately 17%. The third bar is the enriched editing rate of using a 19-8 CF editing cassette and a 13-No ext CF editing cassette, where the 13-8 cassette is not extended, which is functionally equivalent to a prime editing system, approximately 19%. Note that as expected, the percent editing obtained for 19-8 cassette alone (second bar) and 19-8 cassette+13-8 cassette (NoExt) (third bar) are similar. Finally, the last bar in the RFP+BFP+ bar graph shows the enriched editing rate of using a 19-8 CF editing cassette+13-8 CF editing cassette, approximately 33%, which is greater than the additive editing rate for both 19-8 cassette and 13-8 cassette alone.

The second bar graph in FIG. 7 demonstrates that the edit fraction obtained with a nickase-RT fusion enzyme and either or both a 19-8 CF editing cassette and/or a 13-8 CF editing cassette is greater than the edit fraction obtained with prime editing-equivalent system. Edit fraction was calculated by the equation edit fraction=edit/(edit+indel). The edit fraction is higher for systems with fewer indels. The left-most bar shows that the edit fraction for the 13-8 CF editing cassette alone was approximately 57%. The second bar shows that the edit fraction for the 19-8 CF editing cassette alone was approximately 57%. The third bar shows that the edit fraction for the 19-8 CF editing cassette and the 13-No Ext CF editing cassette, where the 13-8 cassette is not extended or copied was approximately 30%. Again, the 19-9 cassette+13-8 cassette (no extension) is functionally equivalent to a prime editing system. Finally, fourth bar shows that the edit fraction for the 19-8 CF editing cassette+13-8 CF editing cassette was greater than 60% indicating a low rate of indels.

FIG. 8 shows two bar graphs where the first bar graph demonstrates that the editing rate is increased when utilizing a nickase-RT fusion enzyme and both a C5-25 CF editing cassette and a 13-8 CF editing cassette as opposed to using only one of these cassettes. Again, in these experiments, 50 ng of the nickase-RT fusion enzyme was used and 25 ng of each CF editing cassette was used to transfect HEK293T cells. RFP+ indicates a cell that has been transfected, and BFP+ indicates a cell that has been edited. The C5-25 CF editing cassette stands for the CFgC5 cassette shown in FIG. 6 which has a post-edit homology length of 25 nucleotides. The 13-8 CF editing cassette stands for the CFg13 cassette shown in FIG. 6 which has a post-edit homology length of 8 nucleotides.

In the first bar graph, the left-most bar the enriched editing rate of using the 13-8 CF editing cassette alone, approximately 10%. The second bar is the enriched editing rate of using the C5-25 CF editing cassette alone, approximately 1%. The third bar is the enriched editing rate of using a C5-25 CF editing cassette and a 13-No Ext CF editing cassette, where the 13-8 cassette is not extended (making this control functionally equivalent to a prime editing system), approximately 3%. Finally, the last bar in the RFP+BFP+ bar graph shows the enriched editing rate of using a C5-25 CF editing cassette+a 13-8 CF editing cassette, approximately 20%, which is greater than the additive editing rate for both C5-25 cassette and 13-8 cassette alone.

The second bar graph in FIG. 8 demonstrates that the edit fraction obtained with a nickase-RT fusion enzyme and either or both a C5-25 CF editing cassette and/or a 13-8 CF editing cassette is greater than the edit fraction obtained with prime editing. Edit fraction was calculated by the equation edit fraction=edit/(edit+indel). The left-most bar in this second bar graph shows that the edit fraction for the 13-8 CF editing cassette alone was approximately 57%. The second bar shows that the edit fraction for the C5-25 CF editing cassette alone was approximately 40%. The third bar shows that the edit fraction for the C5-25 CF editing cassette and a 13-No Ext CF editing cassette, where the 13-8 cassette is not extended, approximately 15%. Finally, the fourth bar shows that the edit fraction for the C5-25 CF editing cassette+13-8 CF editing cassette was approximately 55%. Again, a higher edit fraction indicates a lower incidence of indels.

Figure 9:
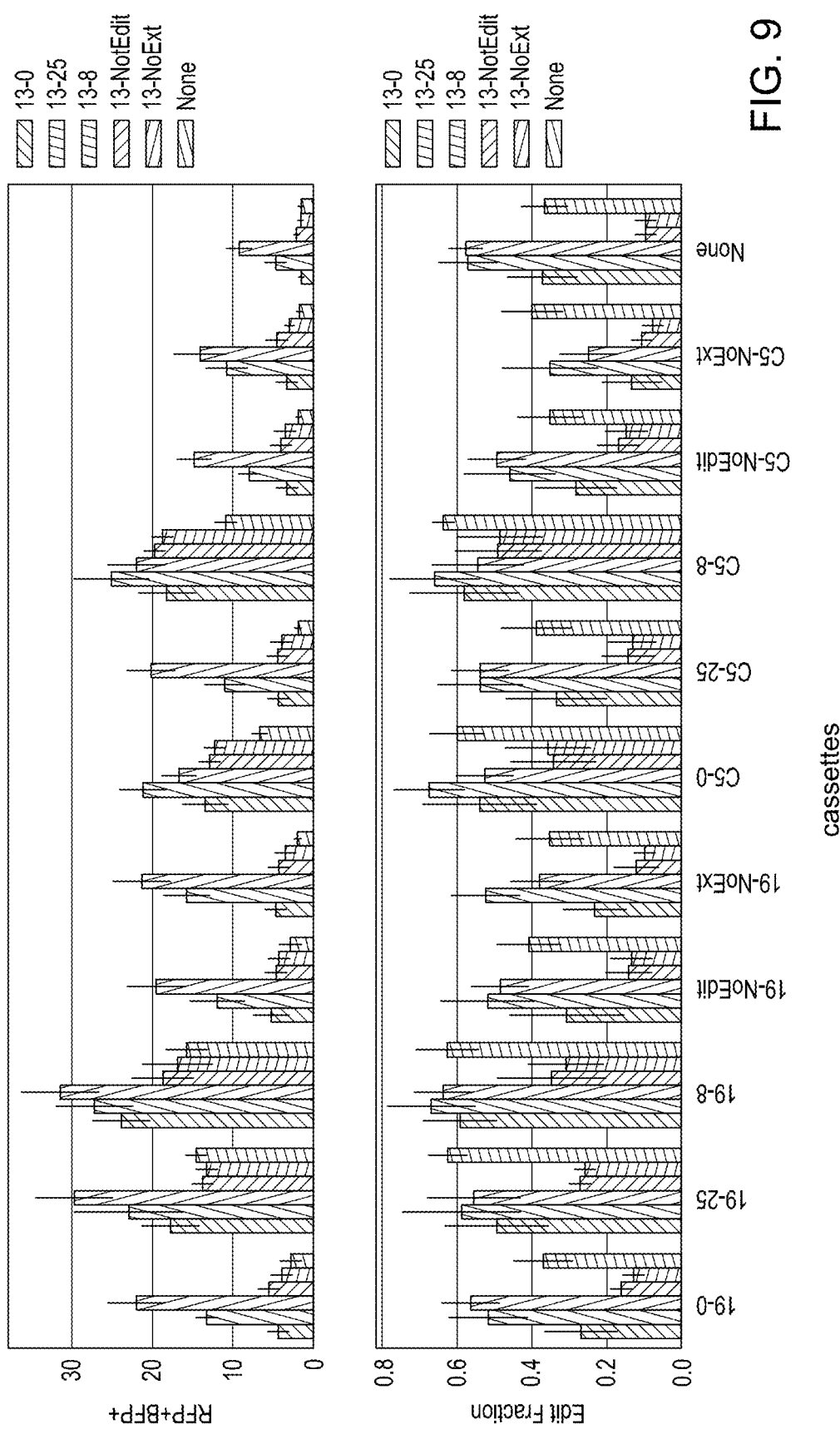
FIG. 9 is a series of bar graphs for both editing rate and edit fraction showing that utilizing a second CF editing cassette with a PEH>0 shows significant improvement in editing and a significant decrease in indels as reported by edit fraction (HR/(NHEJ+HR)).

FIG. 9 is a series of bar graphs showing that utilizing a second CF editing cassette with a PEH>0 shows significant improvement in editing over both prime editing and use of a single CF editing cassette. The first cassette used is noted on the X-axis and the second cassette used is noted to the right of the series of bar graphs. Again, for the top graphs, RFP+ indicates a cell that has been transfected, and BFP+ indicates a cell that has been edited. For the bottom graphs, edit fraction was calculated by the equation Edit Fraction=edit/(edit+indel). Again, "NoExt" denotes a cassette that is not extended (and thus provides a system equivalent to prime editing". "NoEdit" denotes a nick-to-edit stretch of nucleotides but does not include an edit or a post-homology complementary region.

Example V: Dual CF Editing Cassette Nucleic Acid-Guided Nickase/Reverse Transcriptase Fusion Editing—Insertion Proof of Concept Reporter cell lines comprising mammalian cells (HEK293T) having an integrated genomic copy of the BFP gene with a 49-bp deletion therein were generated utilizing lentiviral methods and cultured in complete medium (DMEM medium supplemented with 10% FBS and 1% Penicillin, Streptomycin, and Amphotericin) supplemented with zeocin. These cell lines enabled detection of insertion of the missing 49-bp sequence by various different phenotypic and genotypic mechanisms, including flow cytometry, fluorescent cell imaging, and genotypic detection by sequencing of the genome-integrated BFP gene. Integration of the missing 49-bp sequence results in restoration of the BFP gene and thus, BFP fluorescence (e.g., BFP+), or restoration of the reading frame and thus, a readout of a fully-functional BFP gene.

Figure 10A:
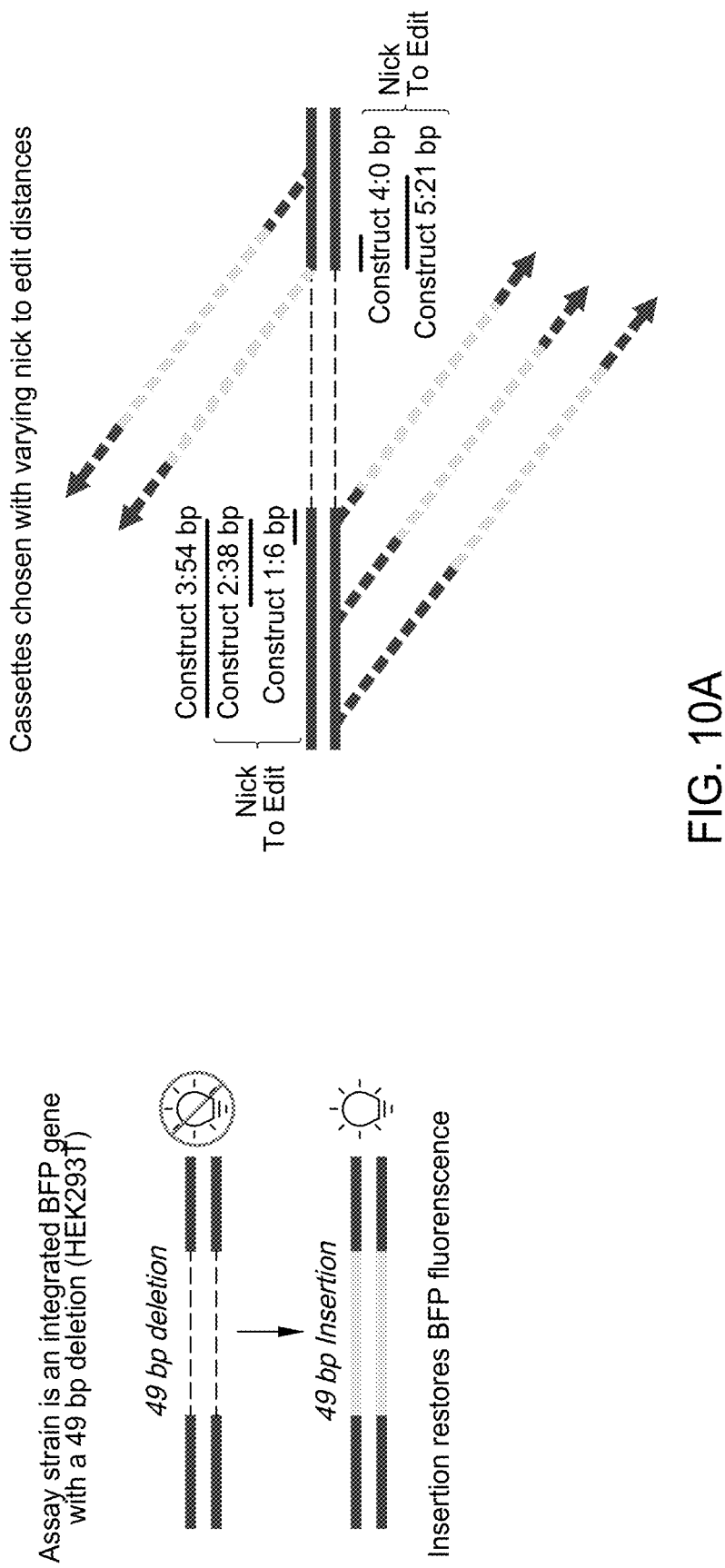
Figure 10B:
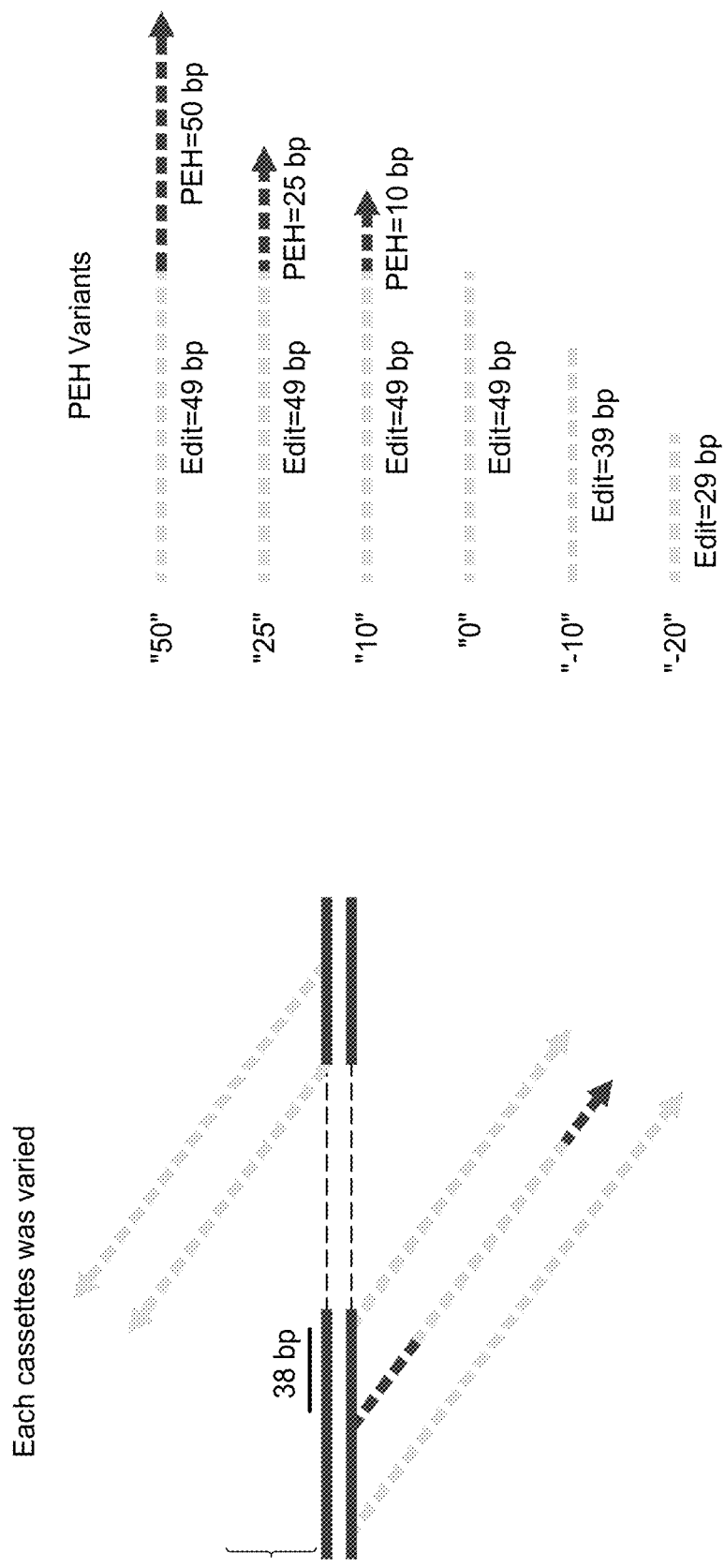

The dual CF editing cassette nickase/RT fusion system was tested for successful integration of the missing 49-bp sequence in these cells (hereinafter, the "insertion"), and benchmarked against a single CF editing cassette nickase/RT fusion system. Each cassette in this experiment was designed to encode for at least a portion of the 49-bp sequence insertion with one of five different nick-to-edit lengths (6 bp, 38 bp, 54 bp, 0 bp, or 21 bp; hereinafter referred to as "constructs" 1, 2, 3, 4, or 5, respectively), as shown in FIG. 10A. For each of the five constructs, six "PEH variants" were created with varying PEH region lengths (e.g., 50 bp, 25 bp, 10 bp, 0 bp, −10 bp, −20 bp), as shown in FIG. 10B. Accordingly, four of the PEH variants for each construct encoded the entire 49-bp insertion as well as a PEH region ("50," "25," "10," and "0"), while two of the PEH variants encoded only a portion of the sequence without a corresponding PEH region ("−10" and "−20," encoding 39/49 bp and 29/49 bp, respectively).

Figure 10C:
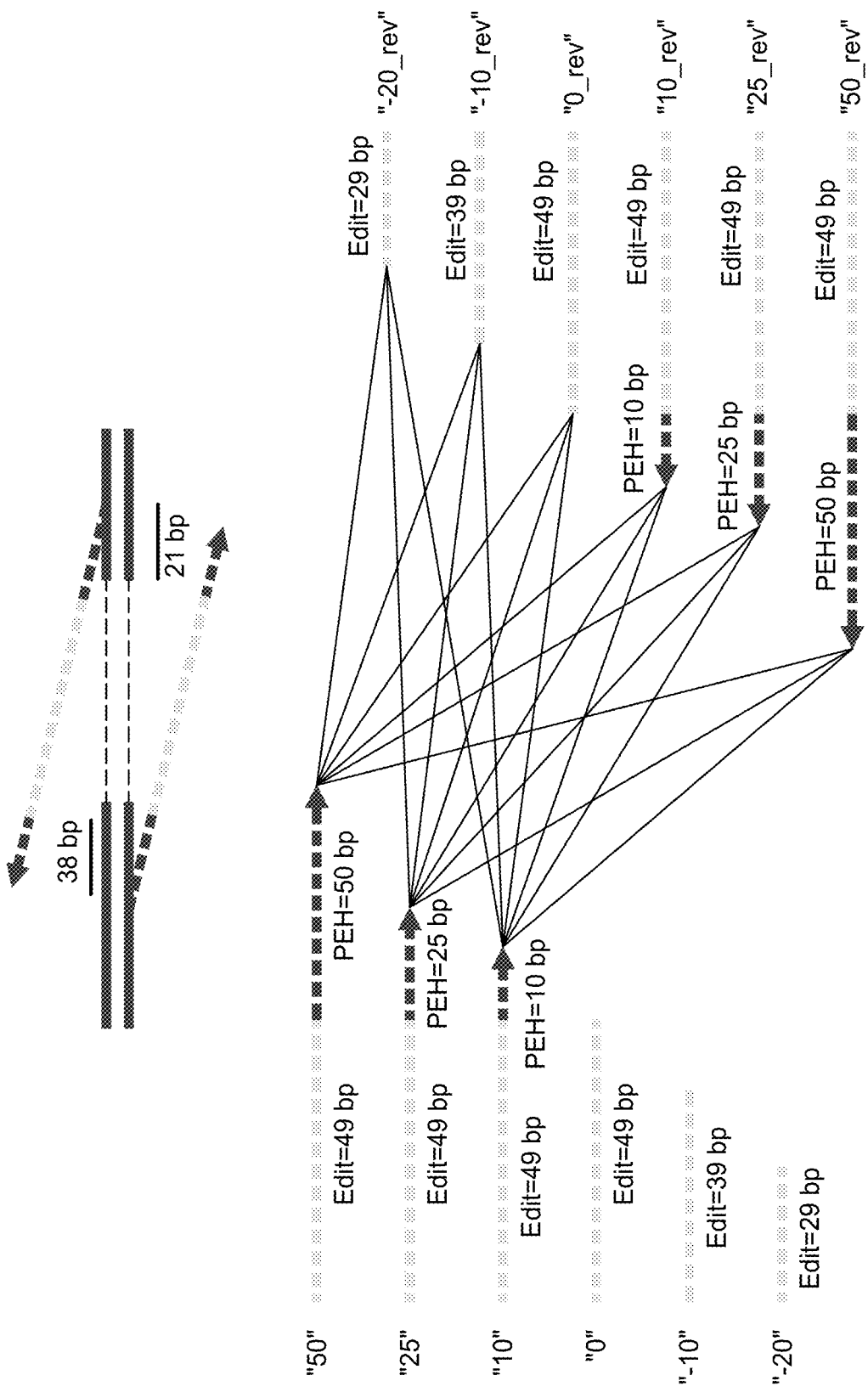
Figure 10D:
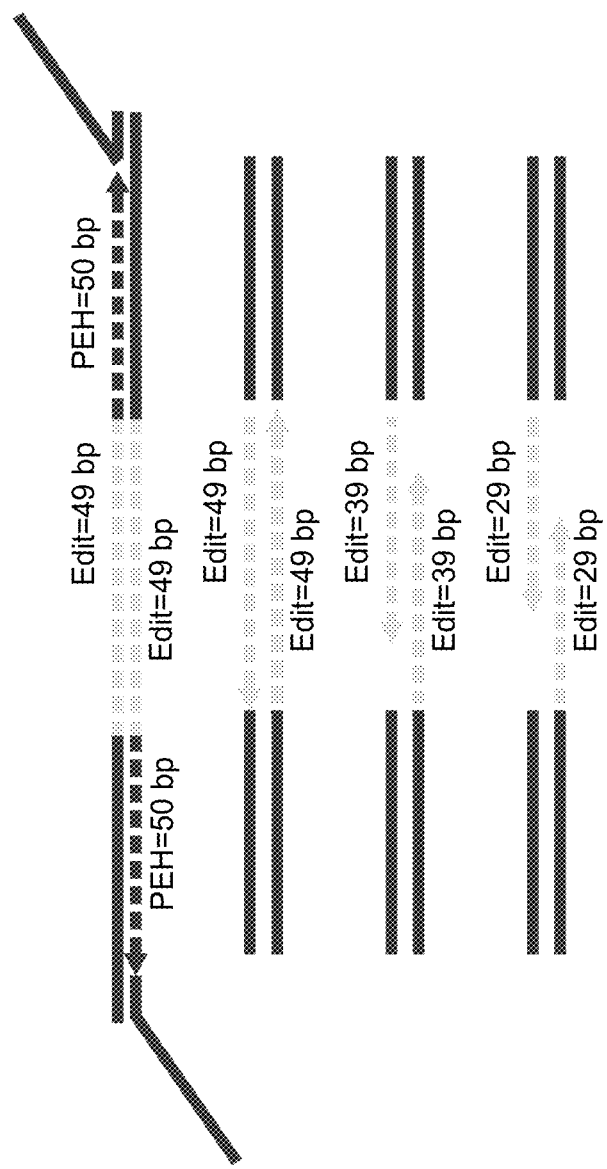

For single CF editing cassette nickase/RT fusion editing, each experimental cassette variant was individually transfected into HEK293T cells, without a second, complementary CF editing cassette. For dual CF editing cassette nickase/RT fusion editing, each experimental cassette variant was co-transfected into HEK293T cells with one of each complementary CF editing cassette, as shown in FIG. 10C, in biological duplicate. This resulted in cassette pairs synthesizing edit "flaps" with overlapping regions of different lengths, schematically depicted in FIG. 10D. For example, as shown at the top of FIG. 10D, pairing a "forward" CF editing cassette variant (i.e., a cassette binding to the antisense strand) having a 50-bp PEH region and a 49-bp edit region with a "reverse" CF editing cassette variant (i.e., a cassette binding to the sense strand) also having a 50-bp PEH region and a 49-bp edit region resulted in newly synthesized complementary DNA flaps having an overlap length of 150 bp. Accordingly, at least 50 bp of genomic DNA was displaced from each strand. Whereas, as shown at the bottom of FIG. 10D, pairing a forward=cassette variant having no PEH region and a 29-bp edit region (i.e., only a portion of the 49-bp BFP insertion) with a reverse=cassette variant also having no PEH region and a 29-bp edit region resulted in newly synthesized complementary DNA flaps having an overlap length of only 9 bp, with far less strand displacement. Note that, although the CF editing cassette pairings in the bottom two examples of FIG. 10D resulted in gaps between newly synthesized edits and genomic DNA, the presence of overlap between the newly synthesized DNA flaps facilitated gap repair mechanisms to effect the entire 49-bp edit in the genomic DNA.

CF editing cassettes on plasmids were placed under the control of a U6 promoter, and a plasmid containing the CFE enzyme was placed under the control of a CMV promoter with a CAG enhancer. dsRED was linked to the CFE enzyme via a T2A sequence to enable assessment of transfection efficiencies via flow cytometry.

Briefly, to transfect the cells for editing, 100 ng of total DNA (50 ng of CFE plasmid and 50 ng of CF editing cassette) was mixed in a 96 well plate. For single cassette nickase/RT fusion editing, 50 ng of a single CF editing cassette was utilized, while for dual cassette nickase/RT fusion editing, 25 ng of each of two complementary CF editing cassettes was utilized; these were brought to a total volume of 10 uL in OptiMEM. 0.3 uL of TransIT®-293 transfection agent (Minis Bio, Madison, WI) in 9.7 uL OptiMEM was added to each DNA mixture, and the plates were incubated at room temperature for at least 15 minutes. About 20,000 HEK293T cells (containing the integrated BFP with a 49 bp deletion) resuspended in 100 μl of complete medium were then added to the mixtures in 96-well Nunclon delta treated plates (Thermofisher Scientific, Waltham, MA). The resulting mixture was then grownt at 37° C. and 5% $CO_2$ and the cells thereafter split 1:5 on day 3, prior to performance of cytometric analysis on day 5. To split cells on day 3, 100 uL of 1:5 dilution of TrpLE Express (Thermofisher Scientific, Waltham, MA) in PBS was added to each well for 10 minutes at 37° C. and 5% $CO_2$; 20 uL of this cell suspension was placed in 96-well Nunclon delta treated plates in complete medium. Overall, 576 transfections were performed (e.g. 5 different nick-to-edit lengths×6 different PEH variations×two biological replicates+controls). The BFP+ cells that were identified via flow cytometry were indicative of the proportion of cells that have undergone precise editing process to integrate the desired 49-bp insertion and expressed BFP. RFP+ cells were used to identify cells that had been successfully transfected. To harvest the cells on day 5, 100 uL of 1:5 dilution of TrpLE express (Thermofisher Scientific, Waltham, MA) in PBS was added to each well for 10 minutes at 37° C. and 5% $CO_2$; the plate was then centrifuged at 500×g for 5 minutes. The TrypLE solution was asiprated the cell pellet then resuspended in FACS buffer (1×PBS, 1% FBS, 1 mM EDTA and 0.5% BSA). The BFP+ and RFP+ cells were then analyzed on the Attune NxT flow cytometer (Thermofisher Scientific, Waltham, MA) and the data analyzed on FlowJo software.

Figure 11A:
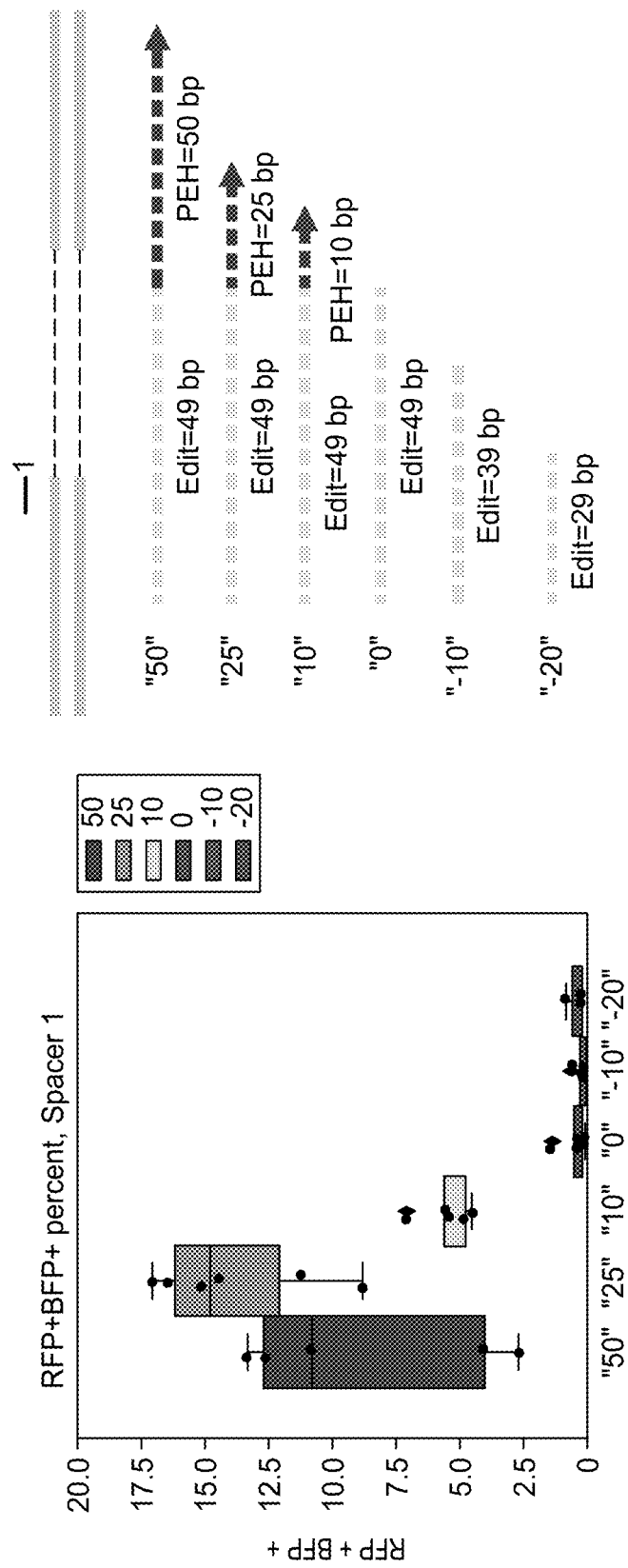
FIG. 11A is a graph demonstrating the impact of PEH length on editing efficiency of a single CF editing cassette nickase-RT fusion editing system.
Figure 11B:
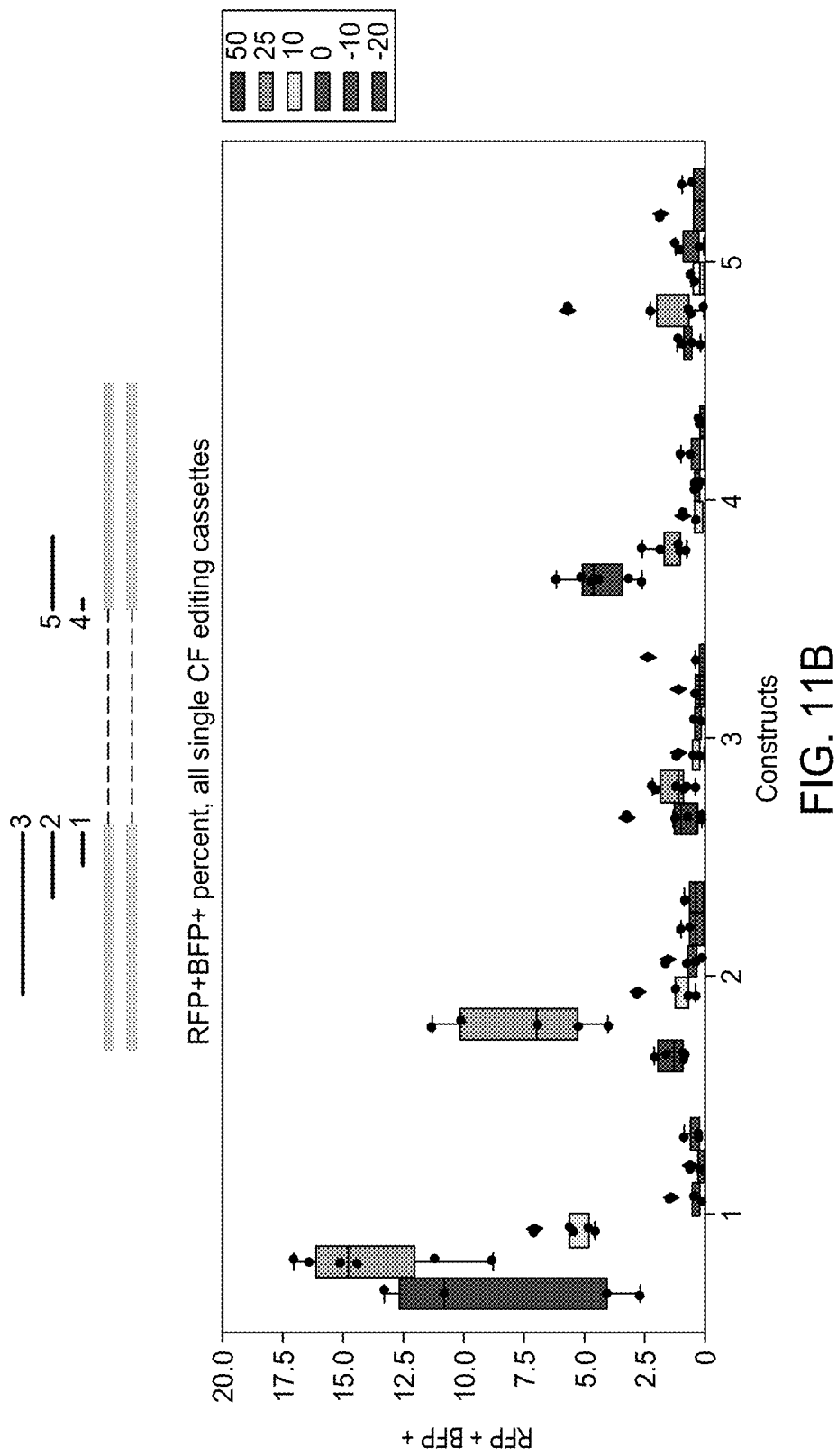
FIG. 11B comprises a graph for editing rates of all CF editing cassettes designed in FIGS. 10A-10D when utilized individually for nickase-RT fusion editing.

FIGS. 11A-10B show two RFP+BFP+ graphs demonstrating the results of nickase/RT fusion editing using single CF editing cassettes. Editing results are assessed by the percentage of transfected (RFP+) cells that are BFP+. In particular, FIG. 11A depicts editing results for one of the cassette constructs, the 6-bp nick-to-edit construct, with varied PEH regions and edit regions, while FIG. 11B depicts editing results for all five cassette constructs and their PEH/edit-length variations when individually deployed. As shown in both graphs, repair and integration of the missing 49-bp BFP sequence was obtained only when utilizing single cassettes encoding the entire insertion as well as a PEH region, though with limited success.

Figure 12A:
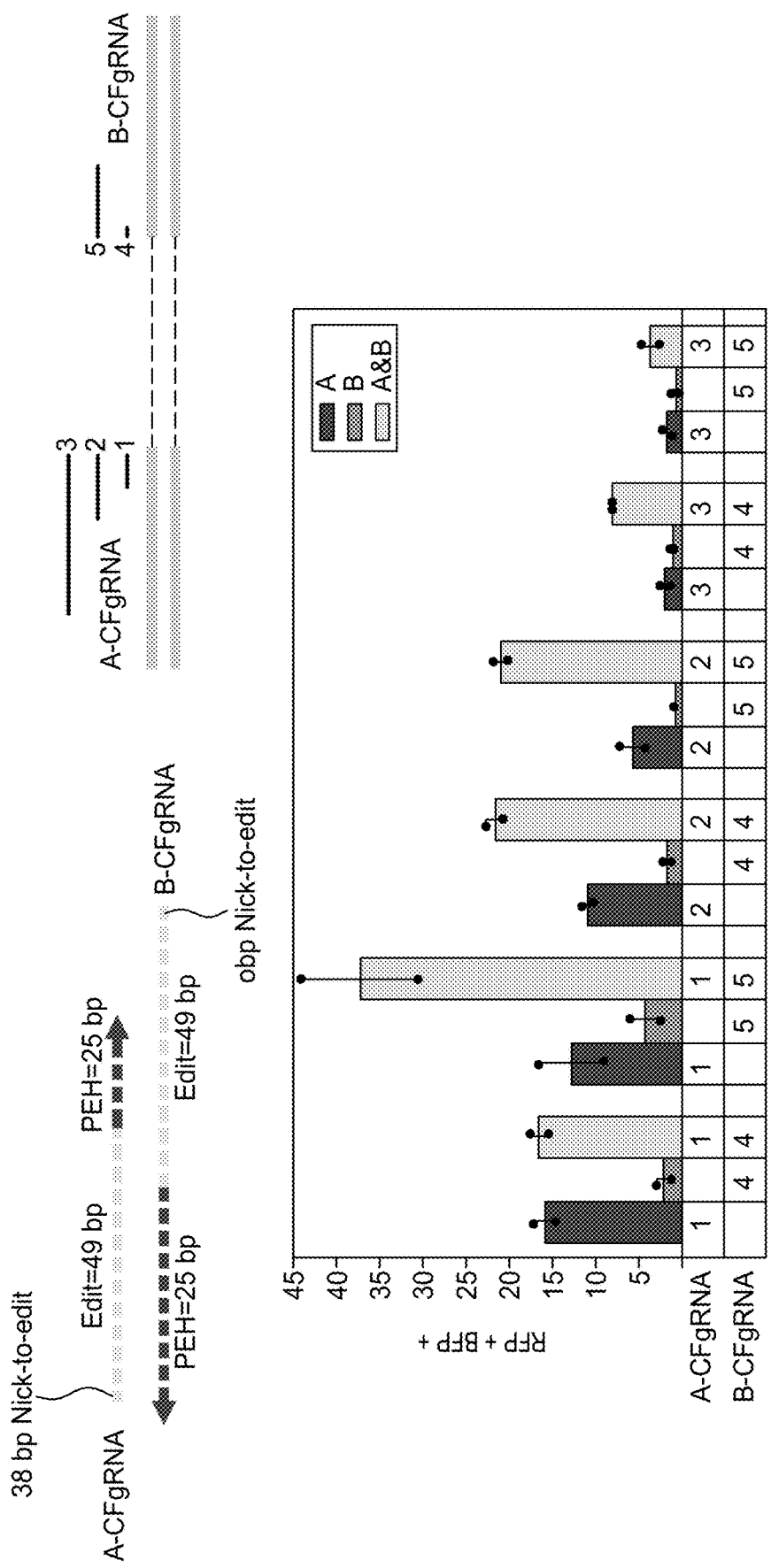
FIGS. 12A-12B are bar graphs demonstrating a step change increase in editing for dual CF editing cassette nickase-RT fusion editing systems as compared to the single-best CF-editing-cassette nickase-RT fusion in the pair.
Figure 12B:
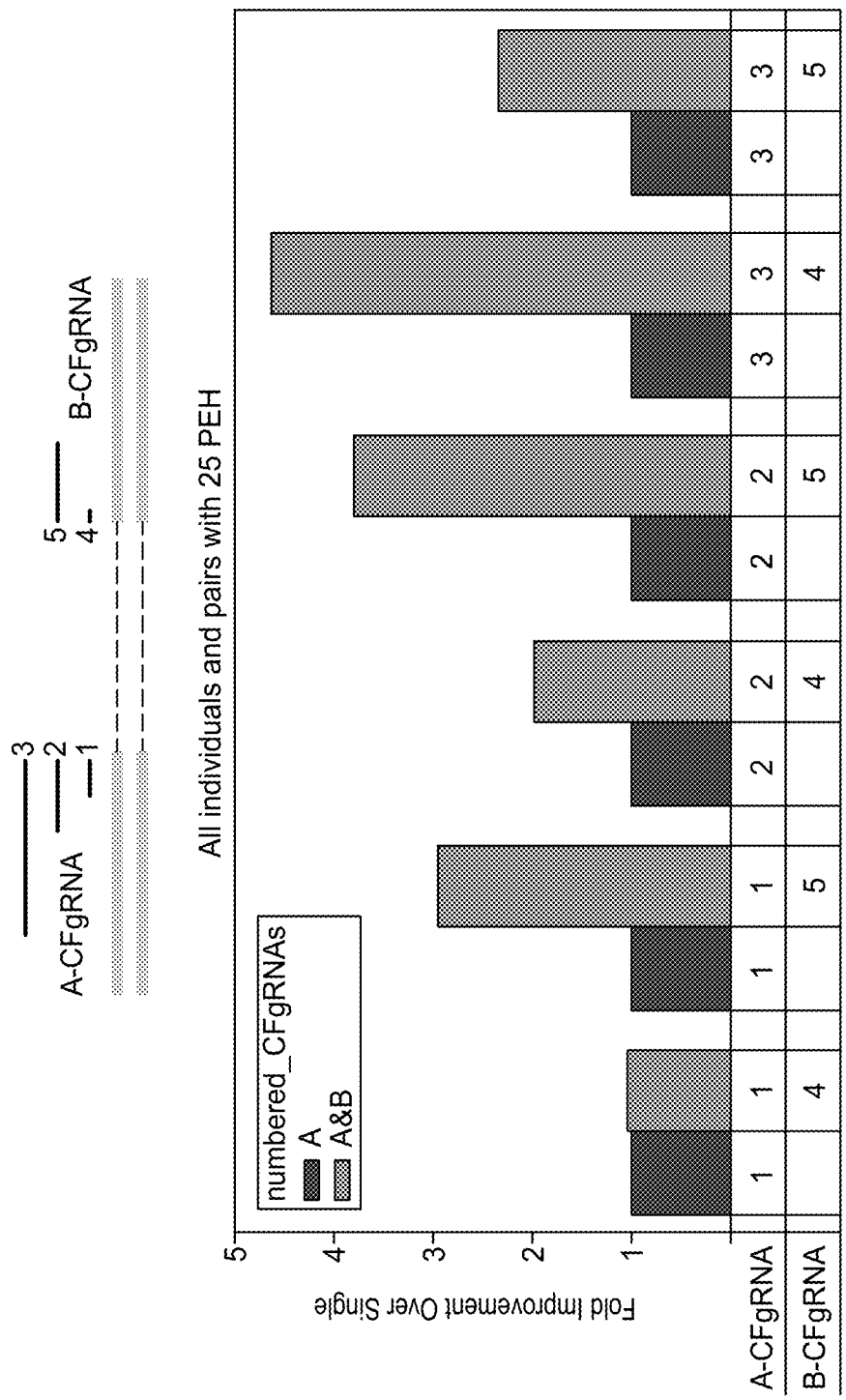

FIGS. 12A-12B show two graphs demonstrating the editing results (the percent of RFP+ cells that are BFP+) of dual CF editing cassette nickase/RT fusion editing as compared to using a single cassette. FIG. 12A depicts editing results for six different combinations of complementary cassettes having different spacers and nick-to-edit lengths but similarly-sized, 25-bp PEH regions (e.g., "construct 1"+"construct 4;" "construct 1"+"construct 5;" "construct 2"+"construct 4;" "construct 2"+"construct 5;" "construct 3"+"construct 4;" and "construct 3"+"construct 5"), as well as the results of using each CF editing cassette alone (e.g., "construct 1;" "construct 2;" "construct 3;" "construct 4;" or "construct 5"). In this example, "A-cassettes" (constructs 1, 2, and 3, comprising 6-bp, 38-bp, and 54-bp nick-to-edit regions, respectively) are 5' to the site of insertion, while "B-cassettes" (constructs 4 and 5, comprising 0-bp and 21-bp nick-to-edit regions, respectively) are 3' to the site of insertion. As shown, utilizing dual cassettes (right-most bar in each trio of bars) significantly increased the occurrence of successful insertion over the most active single cassette (left-most bar in each trio of bars) in 5/6 of the pairwise combinations.

As suggested above, each pairwise combination of CF editing cassettes in FIG. 12A comprised one cassette exhibiting a greater editing efficiency than the other when utilized individually. Accordingly, FIG. 12B depicts the fold improvement of using both cassettes in combination (right-most bar in each pair of bars) over using the single, more efficient cassette individually (left-most bar in each pair of bars). On average, utilizing dual CF editing cassettes resulted in an increase of 2.8× in insertion editing rates.

Figure 13:
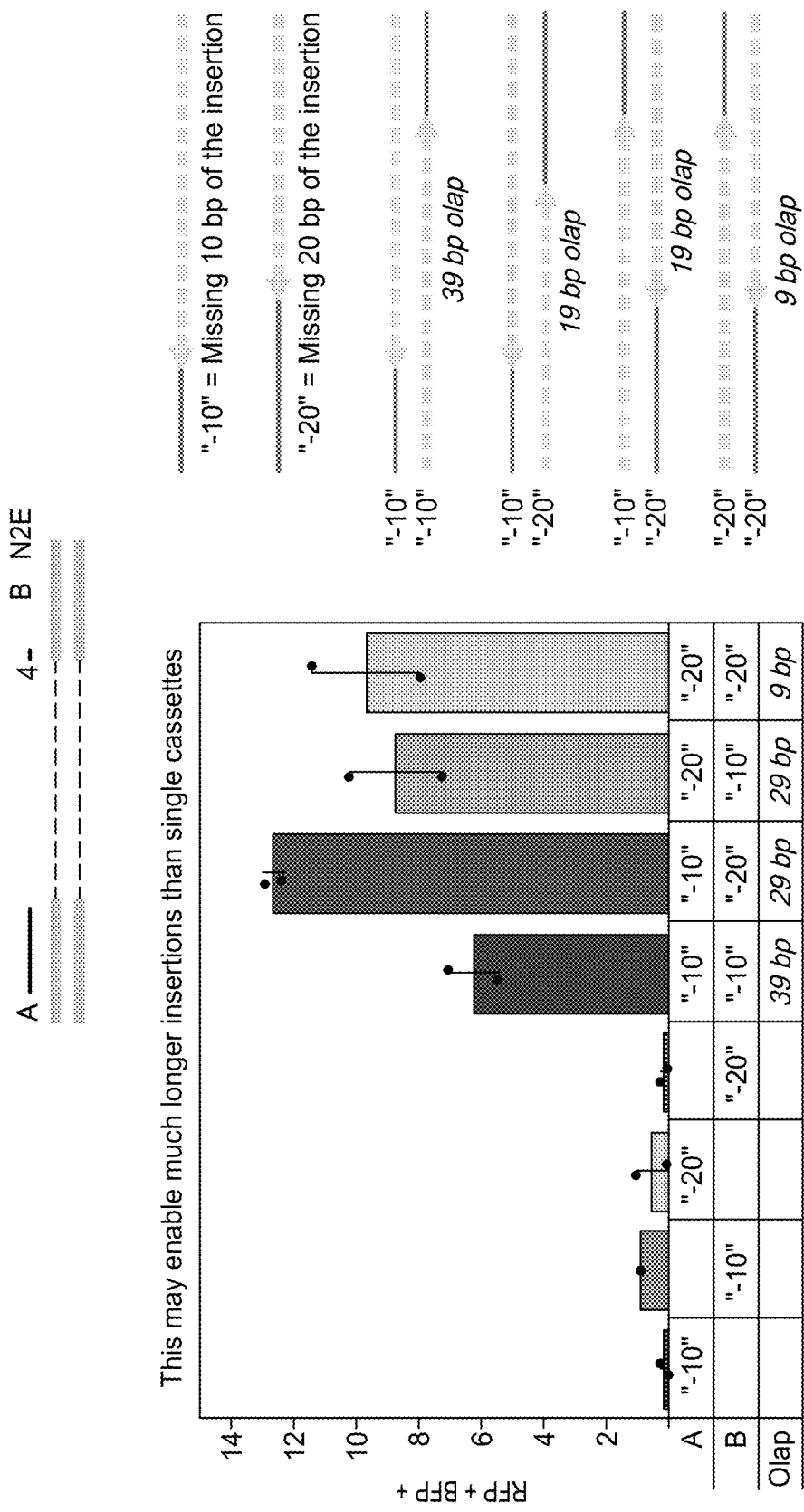
FIG. 13 is a bar graph demonstrating that a complete edit can be split across two separate CF editing cassettes, each cassette comprising only a portion of said edit for nickase-RT fusion editing.

FIG. 13 demonstrates the results of single and dual CF editing cassette nickase/RT fusion editing using cassettes encoding for only a portion of the intended 49-bp insertion. The four left-most bars in the RFP+BFP+ graph depict editing results when utilizing a single cassette comprising either a "−10" or "−20" PEH variation of a 3' or 5' construct. As described above, the −10 and −20 PEH variants encoded only 39/49 bp and 29/49 bp of the intended insertion, respectively. Very little BFP fluorescence was observed when utilizing a single cassette (~1-1.5%), and any such observed fluorescence was likely background noise or baseline fluorescence.

On the other hand, the four right-most bars in the RFP+BFP+ graph depict editing results when utilizing dual CF editing cassettes, wherein each of the pairwise cassettes comprises either the −10 or the −20 PEH variant. In such examples, while each of the pairwise cassettes comprises only a portion of the desired 49-bp insertion, the combination of both cassettes encodes for the entire 49-bp insertion. As shown, a significant percentage of BFP+ transfected (RFP+) cells was observed when utilizing dual CF editing cassettes (~6-13%), thus indicating that for successful editing, both pairwise cassettes were needed in the same cell and at the same time to provide all of the necessary nucleotides to effect the entire insertion. Accordingly, these results demonstrate that the dual flap editing strategy operates as intended.

Dual CF editing cassette nickase/RT fusion editing, wherein each cassette encodes only a portion of the intended edit, may be particularly beneficial for editing operations wherein reverse transcriptase processivity is a limiting factor for editing efficiency. The processivity of a reverse transcriptase refers to the number of nucleotides incorporated in a single binding event of the enzyme. Thus, when using traditional editing techniques, the incorporation of longer edits may be limited by reverse transcriptase processivity. Here, the results in FIG. 13 suggest that a longer edit may be split between two separate CF editing cassettes used in tandem, and thus, reverse transcriptase processivity is less of a factor. A similar strategy may also be pursued when an editing cassette architecture limits that length of an edit that can be encoded by the cassette. In such examples, an intended edit can be split between separate CF editing cassettes, thus making cassette architecture less of a factor. Additionally, native cellular processes or the stability of the CF editing cassette itself, may limit the size of desired inserts, thereby making this strategy advantageous.

Figure 14:
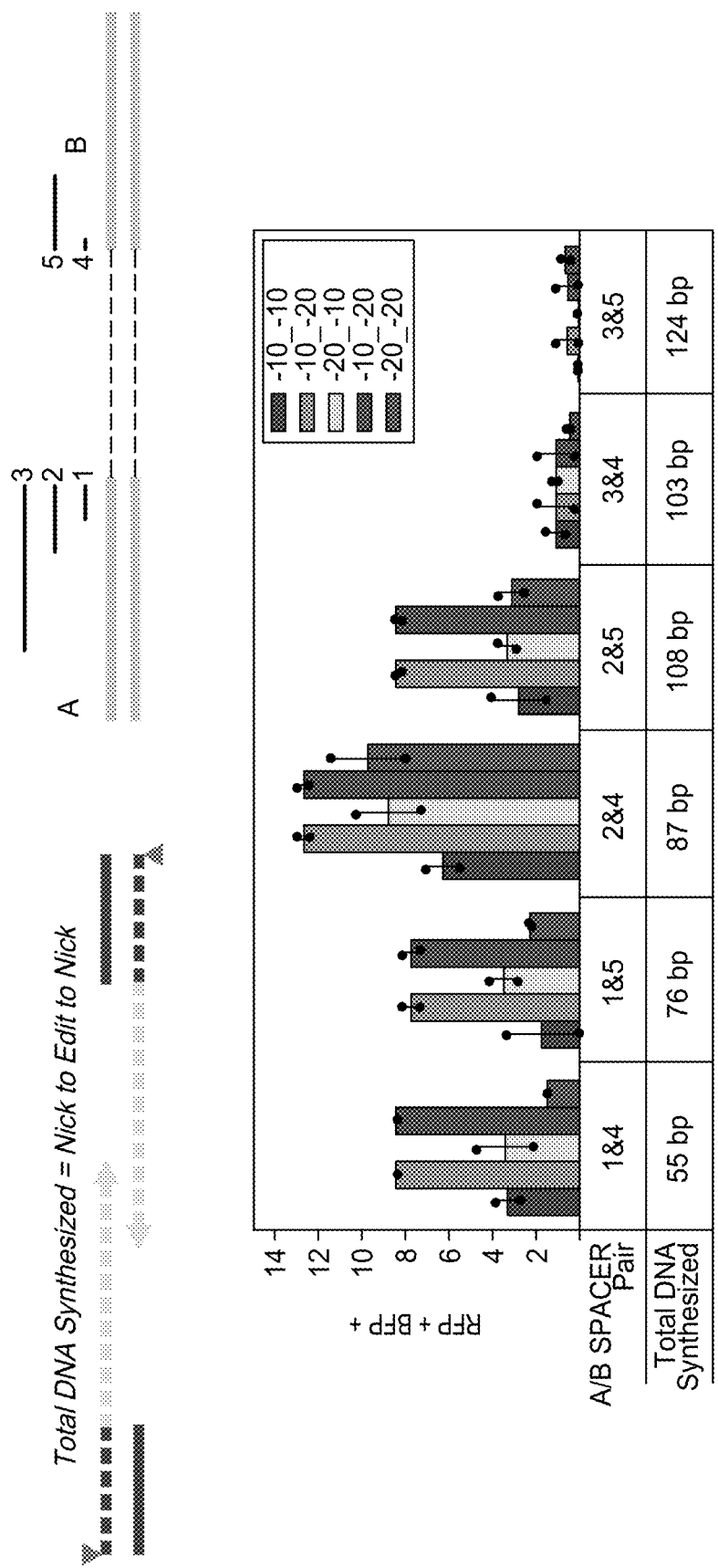
FIG. 14 comprises a bar graph demonstrating that utilizing dual CF editing cassette nickase-RT fusion editing systems may enable larger insertion edits as compared to single CFgRNA nickase-RT fusion editing systems, because of the substantial amount of DNA that must be synthesized via the RT to create the desired edit.

FIG. 14 shows a RFP+BFP+ graph demonstrating the results of dual CF editing cassette nickase/RT fusion editing using cassettes encoding for only a portion of the intended 49-bp insertion, but with different pairwise combinations of constructs (e.g., "1"+"4"; "1"+"5"; "2"+"4"; "2"+"5"; "3"+"4"; and "3"+"5"). In other words, each combination constructs had varying nick-to-edit regions, thereby resulting in different lengths of synthesized DNA during editing for each CF editing cassette pair as measured from nick to nick distance. As shown, up to 108 bp of total DNA was successfully synthesized during editing by the combination of constructs 1 and 2, indicating that dual flap editing strategy enables larger edits than, e.g., more conventional editing strategies, such as traditional prime editing.

Example VI: Dual CF Editing Cassette Nucleic Acid-Guided Nickase/Reverse Transcriptase Fusion Editing—Enhanced Editing at Endogenous Loci The dual CF editing cassette nickase/RT fusion editing system was further tested at two separate endogenous (i.e., genomic) targets and benchmarked against single CF editing cassette conditions to better understand how the dual flap strategy increases editing at endogenous loci.

Here, many pairs of CF editing cassettes were designed to target and effect a 3 bp swap in either the DMNT3b (CCT→GGA) gene or the 4EBP2 (CCG→GGC) gene of HEK293T-GFP cells, with varying spacers and nick-to-edit lengths of up to 146 bp from the intended edit (each CF editing cassette hereinafter referred to as a "construct"). Additionally, all constructs contained a post-edit homology length of 10 nucleotides. Finally, constructs were designed to contain a 2 bp PAM mutation, in order to prevent further binding and/or nicking following editing. For single CF editing cassette nickase/RT fusion editing, each experimental cassette variant was individually transfected into the HEK293T-GFP cells along with a plasmid containing the CFE, without a second, complementary cassette.

For dual CF editing cassette nickase/RT fusion editing, each experimental cassette variant was co-transfected into the cells with a complementary cassette and plasmid encoding the CFE enzyme. Briefly, to transfect the cells for editing, 100 ng of total DNA (50 ng of CFE plasmid and 50 ng of CF editing cassette) was mixed in 96-well Nunclon delta treated plates (Thermofisher Scientific, Waltham, MA), in at least biological duplicate for each target locus. For single CF editing cassette nickase/RT fusion editing, 50 ng of a single cassette was utilized, while for dual CF editing cassette nickase/RT fusion editing, 25 ng of each of two complementary cassettes was utilized; these were brought to a total volume of 10 uL in OptiMEM. 0.3 uL of TransIT®-293 transfection agent (Minis Bio, Madison, WI) in 9.7 uL OptiMEM was added to each DNA mixture, and the plates were incubated at room temperature for at least 15 minutes. Approximately, 40,000 HEK293T GFP cells in 100 uL of complete media were then added to the mixtures in wells of flat 96-well Nunclon delta treated plates.

Figure 15A:
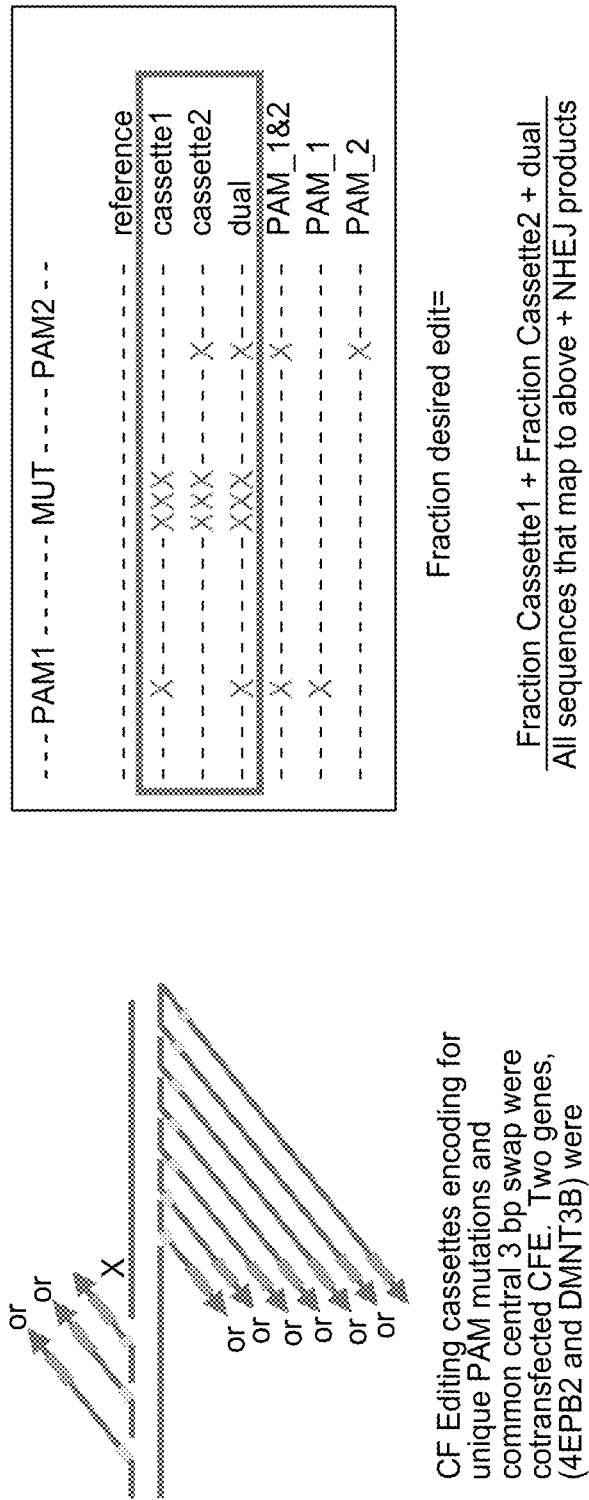
FIG. 15 is a graph demonstrating that individual CF editing cassettes designed to target endogenous loci show a range of editing efficiencies as a function of nick-to-edit distance.

The resulting mixture was then grown at 37° C. and 5% CO2 and the cells thereafter split 1:5 on day 2, prior to performance of cytometric analysis and genomic isolation on day 5. To split cells on day 2, 100 uL of 1:5 dilution of TrpLE Express (Thermofisher Scientific, Waltham, MA) in PBS was added to each well for 10 minutes at 37° C. and 5% CO2; 20 uL of this cell suspension was placed in 96-well Nunclon delta treated plates in complete media. Splitting on day two enabled individual transfections to be expanded into four wells. To harvest the cells on day 5, each of 4 expanded transfections were trypsinized in 100 uL of 1:5 dilution of TrpLE Express (Thermofisher Scientific, Waltham, MA) in PBS was added to each well for 10 minutes at 37° C. and 5% CO2; one replicate plate was then centrifuged at 500×g for 5 minutes. The TrypLE solution was then aspirated and the cell pellet was resuspended in FACS buffer (1×PBS, 1% FBS, 1 mM EDTA and 0.5% BSA). The GFP+ and RFP+ cells were then analyzed on the Attune NxT flow cytometer and the data was analyzed on FlowJo software. 250 uL of identical, expanded trypsinized transfections were pooled and genomic DNA was extracted. Genomic DNA was isolated using the Mag-Bind® Blood & Tissue DNA HDQ 96 Kit (Omega Bio-tek, Norcross, Georgia). Amplicon sequencing was performed on an Illumina MiSeq and analyzed by aligning to a number of potential products outlined in FIG. 15A.

Figure 15B:
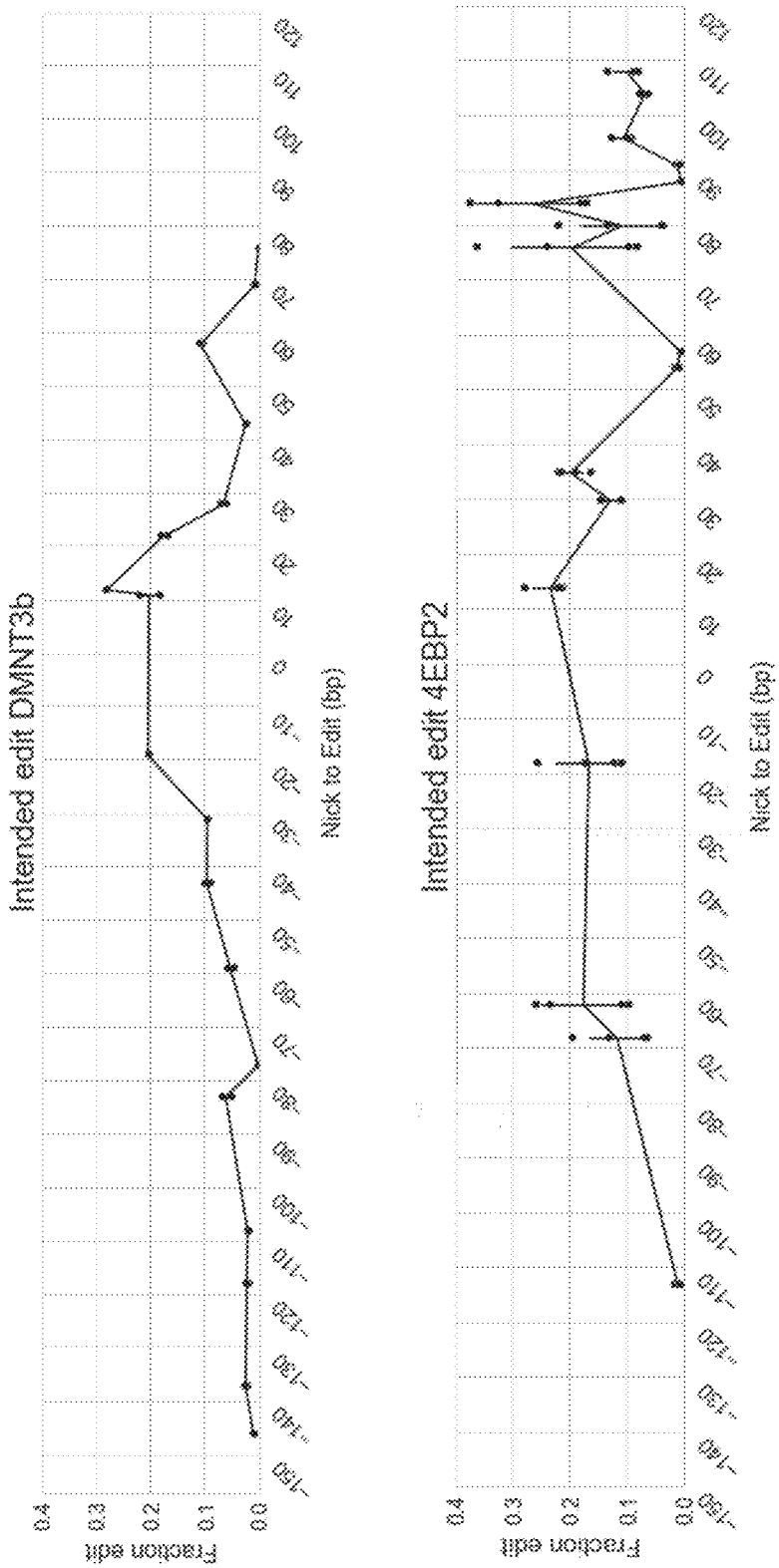

FIG. 15B shows two graphs demonstrating the results of amplicon sequencing analysis of individual CF editing cassette nickase/RT fusion editing for all combinations of designed CF editing cassettes at each target locus, DMNT3b or 4EBP2, as a function of nick-to-edit length. In other words, FIG. 15B shows the fraction of desired edits as related to the distance, in bp, between a spacer region of the CFgRNA in each cassette and the intended edit. As shown, for both DMNT3b and 4EBP2, there is generally a drop off or reduction in successful editing as the nick-to-edit region of the cassette increases.

Figure 16:
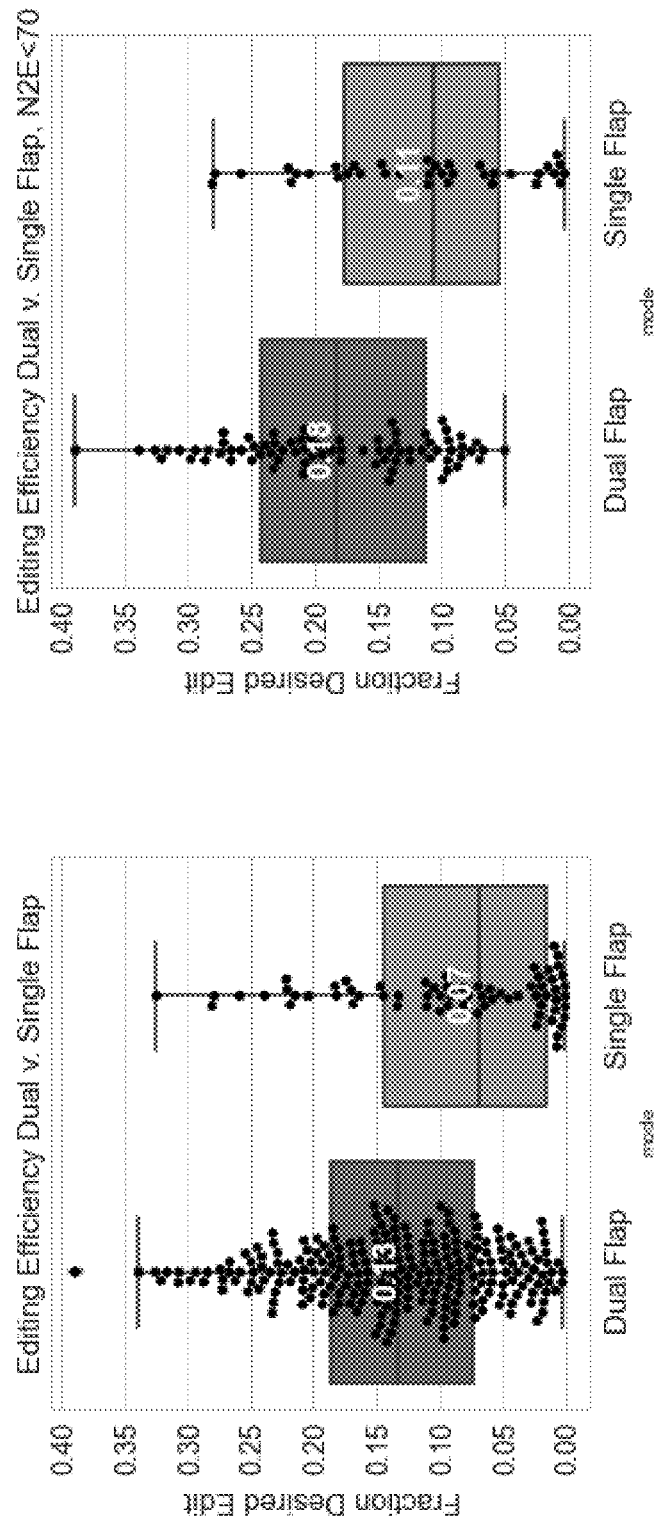
FIG. 16 comprises two graphs demonstrating a higher desired edit fraction for for dual CF editing cassette nickase-RT fusion editing systems as compared to single CFgRNA nickase-RT fusion editing systems. Desired edit fraction is any sequence containing a 3 bp edit over all other sequences that align to the reference sequence

FIG. 16 shows two graphs demonstrating the overall editing efficiency of the dual flap strategy versus the single flap strategy for all experimental CF editing cassettes in FIG. 15B (left graph) described above regardless of nick-to-edit length (left graph), and also for all experimental CF editing cassettes having a nick-to-edit length of less than 70 bp (right graph). Accordingly, the samples in the right graph are downselected for more active cassettes, thereby eliminating data distortion as caused by less active cassettes. As shown, median efficiency was superior when utilizing the dual flap strategy as compared to a single flap strategy for both sets (e.g., ranges) of data.

Figure 17:
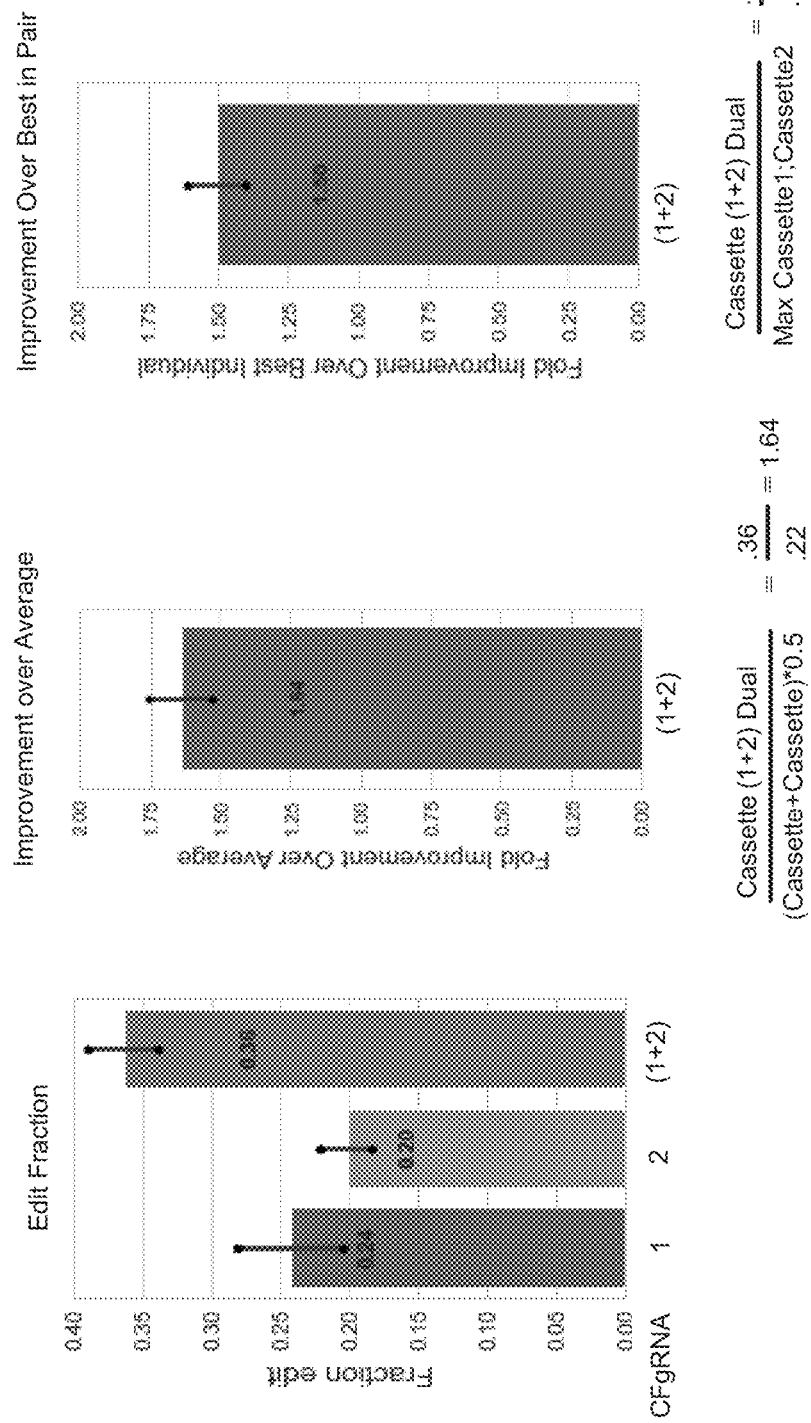
FIG. 17 is a series of three bar graphs demonstrating different metrics for comparing the desired edit fraction of dual CF editing cassette nickase-RT fusion editing systems relative to single CFgRNA nickase-RT fusion editing systems.

FIG. 17 depicts three graphs demonstrating various ways to compare increased endogenous target editing efficiency of the dual flap strategy versus the single flap strategy for a particular pair of experimental CF editing cassettes targeting DNMT3b, described above. CF editing cassette 1 encodes for a 3 bp mutation, a nick-to-edit distance of 19 nucleotides, and a PEH region of 10 nucleotides and a 2 bp PAM mutation. CF editing cassette 2 encodes the same, complementary 2 nucleotide mutation as cassette 1, a nick-to-edit distance of 11 nucleotides, and a PEH region of 10 nucleotides and a PAM mutation of 2 nucleotides. As show in the graph on the far left, each cassette, when utilized individually, resulted in similar fraction of successfully edited cells: about 0.24 for cassette 1 and about 0.20 for cassette 2. When the two cassettes were utilized in combination, the resulting fraction of edited cells improved to about 0.36, which is a 1.64-fold improvement over the average (middle graph) of the individual edit fractions of cassette 1 and cassette 2, and a 1.5-fold improvement over the edit fraction of cassette 1, or the better performing individual cassette (right graph).

Figure 18:
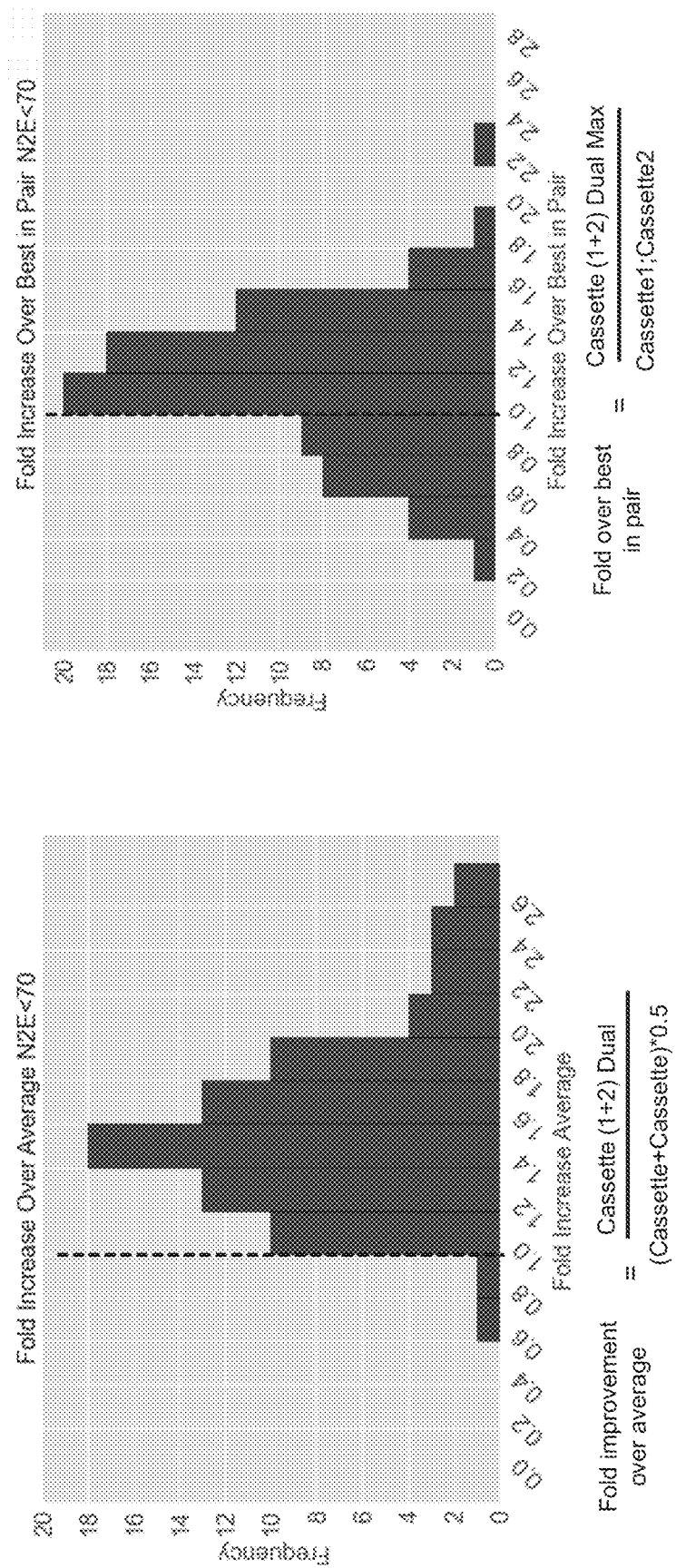
FIG. 18 comprises two graphs demonstrating fold increases in desired edit fractions for pairwise combinations of CF editing cassettes as compared to an average of the desired edit fraction of each individual CF editing cassette in the pair and the increase in desired edit fraction of CF editing cassette pairs relative to the edit fraction of the best-performing cassette in the pair.

FIG. 18 depicts two graphs demonstrating the increased endogenous target editing efficiency of the dual flap strategy versus the single flap strategy for all experimental CF editing cassettes described above having a nick-to-edit length of less than 70 bp. The graph on the left depicts an editing fold increase for all pairwise combinations of CF editing cassettes over an average of the individual edit fractions of the cassettes in each respective pair. The graph on the right depicts an editing fold increase for all pairwise combinations of cassettes over the best-performing cassette in each respective pair. As shown, substantially all pairs of CF editing cassettes perform better than the average of the individual cassettes in each respective pair, and/or better than the best-performing cassette in each respective pair.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are snot to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

EXAMPLE EMBODIMENTS

Embodiment 1: A method for performing nucleic acid-guided nickase/reverse transcriptase fusion editing in a target locus in a genome of a live cell editing utilizing a single CFgRNA comprising: providing a cell with the target locus; providing a nucleic acid-guided nuclease/reverse transcriptase fusion enzyme comprising a first nickase and second nickase fused to a reverse transcriptase component; providing a single CFgRNA, wherein the CFgRNA has a region of complementarity to a first strand of the target locus, and wherein the CFgRNA comprises from 5' to 3' a spacer region, a scaffold region, a post-edit homology region, an edit, a nick-to-edit region, and a PBS region;

providing conditions to allow the nucleic acid-guided nuclease/reverse transcriptase fusion enzyme and the CFgRNA to bind to the first strand of the target locus; allowing the nucleic acid-guided nuclease/reverse transcriptase fusion enzyme to nick the first strand of the target locus and synthesize an edited first strand; and allowing the nucleic acid-guided nuclease/reverse transcriptase fusion enzyme to nick a second strand of the target locus and synthesize an edited second strand, wherein the edited first strand is utilized as a template for the edited second strand.

Embodiment 2: A method for performing nucleic acid-guided nickase/reverse transcriptase fusion editing in a target locus in a genome of a live cell editing utilizing a single CFgRNA comprising: providing a cell with the target locus; providing a nucleic acid-guided nuclease/reverse transcriptase fusion enzyme; providing a CFgRNA, wherein the CFgRNA comprises a tracrRNA component and a crRNA component with regions of complementarity to opposite strands of the target locus, wherein the tracrRNA component comprises from 5' to 3' a structural region (e.g., scaffold) recognized by a Cas protein, a region of complementarity to the crRNA, an optional post-edit homology region, an edit region, a nick to edit region, and a PBS region, and wherein the crRNA component comprises from 5' to 3' a region of complementarity to the genomic target, a region of complementarity to the tracrRNA, an optional post-edit homology region, an edit region, a nick-to-edit region, and a PBS region; providing conditions to allow the nucleic acid-guided nuclease/reverse transcriptase fusion enzyme and the tracrRNA and crRNA components to bind to the opposite strands of the target locus; and allowing the nucleic acid-guided nuclease/reverse transcriptase fusion enzyme and the tracrRNA and crRNA components to edit the target locus.

Embodiment 3: A method for performing nucleic acid-guided nickase/reverse transcriptase fusion editing in a target locus in a genome of a live cell editing utilizing a single RNA transcript comprising: providing a cell with the target locus; providing two different nucleic acid-guided nucleases, wherein each nucleic acid-guided nuclease is fused to an additional nickase, and wherein at least one of the nucleic acid-guided nucleases is further fused to a reverse transcriptase component; providing a single RNA transcript comprising two different Cas gRNAs connected by a linker, the single RNA transcript having regions of complementarity to opposite strands of the target locus, wherein a 3' end of the single RNA transcript comprises from 5' to 3' an optional post-edit homology region, an edit, a nick-to-edit region, and a PBS region, wherein the linker comprises from 5' to 3' an optional post-edit homology region, an edit, a nick-to-edit region, and a PBS region, in which some of the 3' and linker regions are complementary to each other; providing conditions to allow the nucleic acid-guided nuclease/reverse transcriptase fusion enzymes and the Cas gRNAs to bind to the opposite strands of the target locus; and allowing the nucleic acid-guided nuclease/reverse transcriptase fusion enzymes and the Cas gRNAs to edit the target locus.

Embodiment 4: A method for performing nucleic acid-guided nickase/reverse transcriptase fusion editing in a target locus in a genome of a live cell editing utilizing two CFgRNAs comprising: providing a cell with the target locus; providing a nucleic acid-guided nuclease/reverse transcriptase fusion enzyme comprising two Cas orthologues fused to a reverse transcriptase component; providing first and second CFgRNAs, wherein the first and second CFgRNAs have regions of complementarity to opposite strands of the target locus, wherein the first CFgRNA comprises from 5' to 3' an optional post-edit homology region, an edit, a nick-to-edit region, and a PBS region, wherein one or more of the post-edit homology region, the edit, the nick-to-edit region, and the PBS region have complementarity to the second CFgRNA; wherein the second CFgRNA comprises an optional post-edit homology region, an edit region, a nick to edit region, and a PBS; providing conditions to allow the nucleic acid-guided nuclease/reverse transcriptase fusion enzyme and the CFgRNAs to bind to the opposite strands of the target locus; and allowing the nucleic acid-guided nuclease/reverse transcriptase fusion enzyme and the CFgRNAs to edit the target locus.

Cas9-RT-Cas9

Embodiment 5: A method for performing nucleic acid-guided nickase/reverse transcriptase/nucleic acid-guided nickase fusion editing to produce an edit in a double-stranded DNA target locus in a genome of a live cell utilizing two CF editing cassettes comprising: providing a cell with the target locus; providing a fusion enzyme comprising, in order from amino terminus to carboxy terminus, a first Cas9 nickase, a reverse transcriptase, and a second Cas9 nickase, wherein the first Cas9 nickase and the second Cas9 nickase are orthologs of each other; providing first and second CF editing cassettes, wherein the first and second CF editing cassettes have regions of complementarity to opposite strands of the target locus, and wherein the first CF editing cassette can combine with the first Cas9 nickase and the second CF editing cassette can combine with the second Cas9 nickase to form a functional Cas9 ribonucleoprotein (RNP); wherein: the first CF editing cassette comprises, from 5' to 3', the following regions: (1) a first CFgRNA comprising a first guide sequence which is complementary to a first strand of the target locus, and a first scaffold; and (2) a repair template comprising a first post-edit homology region, a first edit region, a first nick-to-edit region, and a first primer binding region; the second CF editing cassette comprises, from 5' to 3', the following regions: (1) a second CFgRNA comprising a second guide sequence which is complementary to a second strand of the target locus, and a second scaffold; and (2) a repair template comprising a second post-edit homology region, a second edit region, a second nick-to-edit region, and a second primer binding region, the first edit region is complementary to the second edit region, and a first region of complementarity exists between the first post-edit homology region and the second nick-to-edit region, and a second region of complementarity exists between the second post-edit homology region and the first nick-to-edit region, providing conditions to allow the fusion enzyme and CF editing cassettes to bind to the target locus; and allowing the fusion enzyme and CF editing cassettes to edit the target locus.

Embodiment 6: The method of Embodiment 5, wherein one or both of the CF editing cassettes further comprise an edit to immunize the target locus to prevent re-nicking.

Embodiment 7: The method of Embodiment 5, wherein the nick-to-edit region of one or both of the repair templates is from 2-250 nucleotides in length.

Embodiment 8: The method of Embodiment 7, wherein the nick-to-edit region of one or both of the repair templates is from 5-150 nucleotides in length.

Embodiment 9: The method of Embodiment 5, wherein the nick-to-edit region of one or both of the repair templates is from 0-150 nucleotides in length.

Embodiment 10: The method of Embodiment 5, wherein one or both of the first region of complementarity and the second region of complementarity is from 4-120 nucleotides in length.

Embodiment 11: The method of Embodiment 10, wherein one or both of the first region of complementarity and the second region of complementarity is from 5-80 nucleotides in length.

Embodiment 12: The method of Embodiment 11, wherein one or both of the first region of complementarity and the second region of complementarity is from 6-60 nucleotides in length.

Embodiment 13: The method of Embodiment 5, wherein the first edit region and the second edit region are from 1-750 nucleotides in length.

Embodiment 14: The method of Embodiment 13, wherein the first edit region and the second edit region are from 1-500 nucleotides in length.

Embodiment 15: The method of Embodiment 14, wherein the first edit region and the second edit region are from 1-150 nucleotides in length.

Embodiment 16: The method of Embodiment 5, wherein the first and second CF editing cassettes are designed to provide a deletion of from 1 to 20,000 nucleotides at the target site.

Embodiment 17: The method of Embodiment 5, wherein one or both of the first post-edit homology region and the second post-edit homology region is from 2-50 nucleotides in length.

Embodiment 18: The method of Embodiment 17, wherein one or both of the first post-edit homology region and the second post-edit homology region is from 4-40 nucleotides in length.

Embodiment 19: The method of Embodiment 18, wherein one or both of the first post-edit homology region and the second post-edit homology region is from 5-25 nucleotides in length.

Embodiment 20: The method of Embodiment 5, wherein the edit is selected from the group consisting of a single base swap in the target locus, an insertion in the target locus, a deletion in the target locus, an edit in a coding region in the target locus, and an edit in a noncoding region in the target locus.

Embodiment 21: The method of Embodiment 5, wherein the edit is a single base swap in the target locus.

Embodiment 22: The method of Embodiment 5, wherein the edit is an insertion in the target locus.

Embodiment 23: The method of Embodiment 5, wherein the edit is a deletion in the target locus.

Embodiment 24: The method of Embodiment 5, wherein the edit is in a coding region in the target locus.

Embodiment 25: The method of Embodiment 5, wherein the edit is in a noncoding region in the target locus.

Embodiment 26: The method of Embodiment 5, wherein the reverse transcriptase is selected from the group consisting of an HIV-1 reverse transcriptase, a M-MLV reverse transcriptase, an AMV reverse transcriptase, and an RSV reverse transcriptase.

TracrRNA/crRNA (tracr/crispr)

Embodiment 27: A method for performing fusion protein editing to produce an edit in a double-stranded DNA target locus comprising a top DNA strand and a bottom DNA strand in a genome of a live cell comprising: providing a cell with the target locus; providing a fusion enzyme comprising, in order from amino terminus to carboxy terminus, either: a first nickase, a nucleic acid-guided second nickase, and a reverse transcriptase, or a Cas9 nuclease and a reverse transcriptase, providing a tracrRNA, wherein the tracrRNA comprises, from 5' to 3', a scaffold compatible with the provided nucleic acid-guided second nickase or with the provided Cas9 nuclease, a region of complementarity to a crRNA, a first post-edit homology region, a first edit region, a first nick-to-edit region, and a first primer binding region which is complementary to and can hybridize with the target locus top strand, providing the crRNA, wherein the crRNA comprises, from 5' to 3', a guide sequence which is complementary to and can hybridize with the bottom strand of the target locus, a region of complementarity to the crRNA, a second post-edit homology region, a second edit region, a second nick-to-edit region, and a second primer binding region, wherein: the first edit region is complementary to the second edit region; a first region of complementarity exists between the first post-edit homology region and the second nick-to-edit region; a second region of complementarity exists between the second post-edit homology region and the first nick-to-edit region; and the crRNA comprises a region that is complementary to and can hybridize with the tracrRNA such that the fusion enzyme, crRNA and tracrRNA can form a functional fusion enzyme/crRNA/tracrRNA ribonucleoprotein complex, and providing conditions to allow the fusion enzyme/crRNA/tracrRNA ribonucleoprotein complex to bind to the target locus; and allowing the fusion enzyme/crRNA/tracrRNA ribonucleoprotein complex to edit the target locus.

Embodiment 28: The method of Embodiment 27, wherein one or both of the crRNA and the tracrRNA further comprise an edit to immunize the target locus to prevent re-nicking.

Embodiment 29: The method of Embodiment 27, wherein the nick-to-edit region of one or both of the crRNA and the tracrRNA is from 2-250 nucleotides in length.

Embodiment 30: The method of Embodiment 29, wherein the nick-to-edit region of one or both of the crRNA and the tracrRNA is from 5-150 nucleotides in length.

Embodiment 31: The method of Embodiment 27, wherein the nick-to-edit region of one or both of the crRNA and the tracrRNA is from 0-150 nucleotides in length.

Embodiment 32: The method of Embodiment 27, wherein one or both of the first region of complementarity and the second region of complementarity is from 4-120 nucleotides in length.

Embodiment 33: The method of Embodiment 32, wherein one or both of the first region of complementarity and the second region of complementarity is from 5-80 nucleotides in length.

Embodiment 34: The method of Embodiment 33, wherein one or both of the first region of complementarity and the second region of complementarity is from 6-60 nucleotides in length.

Embodiment 35: The method of Embodiment 27, wherein the edit region of the crRNA and the tracrRNA is from 1-750 nucleotides in length.

Embodiment 36: The method of Embodiment 35, wherein the edit region of the crRNA and the tracrRNA is from 1-500 nucleotides in length.

Embodiment 37: The method of Embodiment 36, wherein the edit region of the crRNA and the tracrRNA is from 1-150 nucleotides in length.

Embodiment 38: The method of Embodiment 27, wherein the fusion enzyme comprises a first nickase, a nucleic acid-guided second nickase, and a reverse transcriptase and wherein the crRNA and the tracrRNA are designed to provide a deletion of from 1 to 20,000 nucleotides at the target site.

Embodiment 39: The method of Embodiment 27, wherein the post-edit homology region of one or both of the crRNA and the tracrRNA is from 2-50 nucleotides in length.

Embodiment 40: The method of Embodiment 39, wherein the post-edit homology region of one or both of the first or second CFgRNAs is from 4-40 nucleotides in length.

Embodiment 41: The method of Embodiment 40, wherein the post-edit homology region of one or both of the first or second CFgRNAs is from 5-25 nucleotides in length.

Embodiment 42: The method of Embodiment 27, wherein the edit is selected from the group consisting of a single base swap in the target locus, an insertion in the target locus, a deletion in the target locus, an edit in a coding region in the target locus, and an edit in a noncoding region in the target locus.

Embodiment 43: The method of Embodiment 27, wherein the edit is a single base swap in the target locus.

Embodiment 44: The method of Embodiment 27, wherein the edit is an insertion in the target locus.

Embodiment 45: The method of Embodiment 27, wherein the fusion enzyme comprises a first nickase, a nucleic acid-guided second nickase, and a reverse transcriptase and wherein the edit is a deletion in the target locus.

Embodiment 46: The method of Embodiment 27, wherein the edit is in a coding region in the target locus.

Embodiment 47: The method of Embodiment 27, wherein the edit is in a noncoding region in the target locus.

Embodiment 48: The method of Embodiment 27, wherein the fusion enzyme comprises a first nickase, a nucleic acid-guided second nickase, and a reverse transcriptase and the first nickase recognizes and can nick only a single DNA sequence, a set of related DNA sequences, or all sequences.

Embodiment 49: The method of Embodiment 27, wherein the reverse transcriptase is selected from the group consisting of an HIV-1 reverse transcriptase, a M-MLV reverse transcriptase, an AMV reverse transcriptase, and an RSV reverse transcriptase.

Embodiment 50: The method of Embodiment 27, wherein the fusion enzyme comprises a first nickase, a nucleic acid-guided second nickase, and a reverse transcriptase and the nucleic acid-guided first nickase is selected from the group consisting of a MAD2007 nickase and a Cas9 nickase.

RNA Bridge

Embodiment 51: A method for performing fusion protein editing to produce an edit in a double-stranded DNA target locus comprising a top DNA strand and a bottom DNA strand in a genome of a live cell comprising: providing a cell with the target locus; providing a first polypeptide and a second polypeptide, wherein the first polypeptide is a first fusion enzyme that comprises a catalytically inactive type V nucleic acid guided nuclease, a first nickase and a reverse transcriptase, or the first polypeptide is a first fusion enzyme that comprises a catalytically active type V nucleic acid guided nickase and a reverse transcriptase, and the second polypeptide is a second fusion enzyme that comprises a catalytically inactive type II nucleic acid guided nuclease and a second nickase, or the second polypeptide comprises a catalytically active type II nucleic acid guided nickase, providing a dual guide RNA comprising, from 5' to 3', a first scaffold, a first guide sequence, a first post-edit homology region, a first edit region, a first nick-to-edit region, and a first primer binding region, wherein the first scaffold is compatible with a type V nucleic acid guided nuclease, a second guide sequence, a second scaffold, a second post-edit homology region, a second edit region, a second nick-to-edit region, and a second primer binding region, wherein the second scaffold is compatible with a type II nucleic acid guided nuclease, wherein: the first edit region is complementary to the second edit region; a first region of complementarity exists between the first post-edit homology region and the second nick-to-edit region; a second region of complementarity exists between the second post-edit homology region and the first nick-to-edit region; and providing conditions to allow the first polypeptide, the second polypeptide and the dual guide RNA to associate with each other and bind to the target locus; and allowing the first polypeptide, the second polypeptide and the dual guide RNA to edit the target locus.

Embodiment 52: The method of Embodiment 51, wherein the dual guide RNA further comprises one or more edits to immunize the target locus to prevent re-nicking.

Embodiment 53: The method of Embodiment 51, wherein one or both of the nick-to-edit regions is from 2-250 nucleotides in length.

Embodiment 54: The method of Embodiment 53, wherein one or both of the nick-to-edit regions is from 5-150 nucleotides in length.

Embodiment 55: The method of Embodiment 51, wherein one or both of the nick-to-edit regions is from 0-150 nucleotides in length.

Embodiment 56: The method of Embodiment 51, wherein one or both of the first region of complementarity and the second region of complementarity is from 4-120 nucleotides in length.

Embodiment 57: The method of Embodiment 56, wherein one or both of the first region of complementarity and the second region of complementarity is from 5-80 nucleotides in length.

Embodiment 58: The method of Embodiment 57, wherein one or both of the first region of complementarity and the second region of complementarity is from 6-60 nucleotides in length.

Embodiment 59: The method of Embodiment 51, wherein the first edit region and the second edit region are from 1-750 nucleotides in length.

Embodiment 60: The method of Embodiment 59, wherein the first edit region and the second edit region are from 1-500 nucleotides in length.

Embodiment 61: The method of Embodiment 60, wherein the first edit region and the second edit region are from 1-150 nucleotides in length.

Embodiment 62: The method of Embodiment 51, wherein the dual guide RNA is designed to provide a deletion of from 1 to 750 nucleotides at the target site.

Embodiment 63: The method of Embodiment 51, wherein one or both of the first post-edit homology region and the second post-edit homology region is from 2-50 nucleotides in length.

Embodiment 64: The method of Embodiment 63, wherein one or both of the first post-edit homology region and the second post-edit homology region is from 4-40 nucleotides in length.

Embodiment 65: The method of Embodiment 64, wherein one or both of the first post-edit homology region and the second post-edit homology region is from 5-25 nucleotides in length.

Embodiment 66: The method of Embodiment 51, wherein the edit is selected from the group consisting of a single base swap in the target locus, an insertion in the target locus, a deletion in the target locus, an edit in a coding region in the target locus, and an edit in a noncoding region in the target locus.

Embodiment 67: The method of Embodiment 51, wherein the edit is a single base swap in the target locus.

Embodiment 68: The method of Embodiment 51, wherein the edit is an insertion in the target locus.

Embodiment 69: The method of Embodiment 51, wherein the edit is a deletion in the target locus.

Embodiment 70: The method of Embodiment 51, wherein the edit is in a coding region in the target locus.

Embodiment 71: The method of Embodiment 51, wherein the edit is in a noncoding region in the target locus.

Embodiment 72: The method of Embodiment 51, wherein the reverse transcriptase is selected from the group consisting of an HIV-1 reverse transcriptase, a M-MLV reverse transcriptase, an AMV reverse transcriptase, and an RSV reverse transcriptase.

Embodiment 73: The method of Embodiment 51, wherein the first polypeptide comprises: a catalytically inactive type V nucleic acid guided nuclease, wherein the catalytically inactive type V nucleic acid guided nuclease is dMAD7, or a catalytically active type V nucleic acid guided nickase, wherein the catalytically active type V nucleic acid guided nickase is MAD7, MAD297, MAD298, or MAD299, nickase; and wherein the second polypeptide comprises: a catalytically inactive type II nucleic acid guided nuclease, wherein the catalytically inactive type II nucleic acid guided nuclease is dMAD2019, or a catalytically active type II nucleic acid guided nickase, wherein the catalytically active type II nucleic acid guided nickase is MAD2007 nickase.

Embodiment 74: The method of Embodiment 73, wherein the reverse transcriptase is selected from the group consisting of an HIV-1 reverse transcriptase, a M-MLV reverse transcriptase, an AMV reverse transcriptase, and an RSV reverse transcriptase.

Dual CFgRNAs

Embodiment 75: A method for performing nucleic acid-guided nickase/reverse transcriptase fusion editing in a target locus in a genome of a live cell editing utilizing two CF editing cassettes comprising: providing a cell with the target locus; providing a nucleic acid-guided nuclease/reverse transcriptase fusion enzyme; providing first and second CF editing cassettes, wherein the first and second CF editing cossets have regions of complementarity to opposite strands of the target locus; wherein the first CF editing cassette comprises from 5' to 3': (1) a first CFgRNA comprising a 5' to 3'spacer region and scaffold region; and (2) a first repair template comprising an optional post-edit homology (PEH) region, an edit, a nick-to-edit region, and a primer binding site (PBS) region; and wherein the second CF editing cassette comprises from 5' to 3': (1) a second CFgRNA comprising a 5' to 3'spacer region and scaffold region; and (2) a second repair template comprising an optional post-edit homology (PEH) region, an edit, a nick-to-edit region, and a primer binding site (PBS) region; providing conditions to allow the nucleic acid-guided nuclease/reverse transcriptase fusion enzyme and CF editing cassettes to bind to the opposite strands of the target locus; and allowing the nucleic acid-guided nuclease/reverse transcriptase fusion enzyme and CF editing cassettes to edit the target locus.

Embodiment 76: The method of Embodiment 75, wherein the CF editing cassettes further comprise an edit to immunize the target locus to prevent re-nicking.

Embodiment 77: The method of Embodiment 75, wherein the nick-to-edit region of at least one of the first or second CF editing cassette is from 2-250 nucleotides in length.

Embodiment 78: The method of Embodiment 77, wherein the nick-to-edit region of at least one of the first or second CF editing cassette is from 5-150 nucleotides in length.

Embodiment 79: The method of Embodiment 75, wherein the nick-to-edit region of at least one of the first or second CF editing cassette is from 0-150 nucleotides in length.

Embodiment 80: The method of Embodiment 75, wherein the region of complementarity between the first and second CF editing cassettes is from 4-120 nucleotides in length.

Embodiment 81: The method of Embodiment 80, wherein the region of complementarity between the first and second CF editing cassettes is from 5-80 nucleotides in length.

Embodiment 82: The method of Embodiment 81, wherein the region of complementarity between the first and second CF editing cassettes is from 6-60 nucleotides in length.

Embodiment 83: The method of Embodiment 75, wherein the edit region of the first and second CF editing cassettes is from 1-750 nucleotides in length.

Embodiment 84: The method of Embodiment 83, wherein the edit region of the first and second CF editing cassettes is from 1-500 nucleotides in length.

Embodiment 85: The method of Embodiment 84, wherein the edit region of the first and second CF editing cassettes is from 1-150 nucleotides in length.

Embodiment 86: The method of Embodiment 75, wherein the post-edit homology region of at least one of the first or second CF editing cassettes is from 2-50 nucleotides in length.

Embodiment 87: The method of Embodiment 86, wherein the post-edit homology region of at least one of the first or second CF editing cassettes is from 4-40 nucleotides in length.

Embodiment 88: The method of Embodiment 87, wherein the post-edit homology region of at least one of the first or second CF editing cassettes is from 5-25 nucleotides in length.

Embodiment 89: The method of Embodiment 75, wherein the edit is a single base swap in the target locus.

Embodiment 90: The method of Embodiment 75, wherein the edit is an insertion in the target locus.

Embodiment 91: The method of Embodiment 75, wherein the edit is a deletion in the target locus.

Embodiment 92: The method of Embodiment 75, wherein the edit is in a coding region in the target locus.

Embodiment 93: The method of Embodiment 75, wherein the edit is in a noncoding region in the target locus.

Embodiment 94: The method of Embodiment 75, wherein the nuclease portion of the nickase/reverse transcriptase fusion is a MAD2007 nickase.

Two Nicks—1 RT

Embodiment 95: A method for performing nucleic acid-guided nickase/reverse transcriptase/nickase fusion editing to produce an edit in a target locus in a genome of a live cell comprising: providing a cell with the target locus; providing a fusion enzyme comprising a first nickase activity, a reverse transcriptase activity, and a second nickase activity, wherein the first nickase activity is nucleic acid-guided, and wherein optionally the fusion enzyme comprises, in order from amino terminus to carboxy terminus, a nucleic acid-guided first nickase, a reverse transcriptase, and a second nickase, providing a CFgRNA, wherein the CFgRNA comprises, from 5' to 3', the following regions: a guide sequence, a scaffold, a post-edit homology region, an edit region, a nick-to-edit region, and a primer binding region; providing conditions to allow the fusion enzyme and CFgRNA to bind to the target locus; and allowing the fusion enzyme and CFgRNA to edit the target locus.

Embodiment 96: The method of Embodiment 95, wherein the CFgRNA further comprises an edit to immunize the target locus to prevent re-nicking.

Embodiment 97: The method of Embodiment 95, wherein the nick-to-edit region is from 2-250 nucleotides in length.

Embodiment 98: The method of Embodiment 97, wherein the nick-to-edit region is from 5-150 nucleotides in length.

Embodiment 99: The method of Embodiment 95, wherein the nick-to-edit region is from 0-150 nucleotides in length.

Embodiment 100: The method of Embodiment 95, wherein the edit region of the CFgRNA is from 1-750 nucleotides in length.

Embodiment 101: The method of Embodiment 100, wherein the edit region of the CFgRNA is from 1-500 nucleotides in length.

Embodiment 102: The method of Embodiment 101, wherein the edit region of the CFgRNA is from 1-150 nucleotides in length.

Embodiment 103: The method of Embodiment 95, wherein the CFgRNA is designed to provide a deletion of from 1 to 750 nucleotides at the target site.

Embodiment 104: The method of Embodiment 95, wherein the post-edit homology region of the CFgRNA is from 2-50 nucleotides in length.

Embodiment 105: The method of Embodiment 104, wherein the post-edit homology region of the CFgRNA is from 4-40 nucleotides in length.

Embodiment 106: The method of Embodiment 105, wherein the post-edit homology region of the CFgRNA is from 5-25 nucleotides in length.

Embodiment 107: The method of Embodiment 95, wherein the edit is selected from the group consisting of a single base swap in the target locus, an insertion in the target locus, a deletion in the target locus, an edit in a coding region in the target locus, and an edit in a noncoding region in the target locus.

Embodiment 108: The method of Embodiment 95, wherein the edit is a single base swap in the target locus.

Embodiment 109: The method of Embodiment 95, wherein the edit is an insertion in the target locus.

Embodiment 110: The method of Embodiment 95, wherein the edit is a deletion in the target locus.

Embodiment 111: The method of Embodiment 95, wherein the edit is in a coding region in the target locus.

Embodiment 112: The method of Embodiment 95, wherein the edit is in a noncoding region in the target locus.

Embodiment 113: The method of Embodiment 95, wherein the fusion enzyme comprises, in order from amino terminus to carboxy terminus, a nucleic acid-guided first nickase, a reverse transcriptase, and a second nickase, wherein the nucleic acid-guided first nickase is a Cas9 nickase, optionally a MAD2007 nickase, and wherein the second nickase recognizes and can nick only a single DNA sequence, a set of related DNA sequences, or all DNA sequences.

Embodiment 114: The method of Embodiment 113, wherein the reverse transcriptase is selected from the group consisting of an HIV-1 reverse transcriptase, an M-MLV reverse transcriptase, an AMV reverse transcriptase, and an RSV reverse transcriptase.

---

We claim:

1. A method for performing nucleic acid-guided nickase/reverse transcriptase fusion editing in a target locus in a genome of a live cell utilizing two CREATE fusion (CF) editing cassettes comprising:
   (a) providing the live cell comprising the target locus;
   (b) providing a nucleic acid-guided nuclease/reverse transcriptase fusion enzyme;
   (c) providing a first CF editing cassette and a second CF editing cassette, wherein the first CF editing cassette comprises a first region of complementarity to a first strand of the target locus, and wherein the second CF editing cassette comprises a second region of complementarity to a second strand of the target locus, wherein the first CF editing cassette comprises a nucleic acid molecule encoding from 5' to 3':
      (i) a first CF guide RNA (gRNA) comprising a 5' to 3' spacer region and a scaffold region; and
      (ii) a first repair template comprising first post-edit homology (PEH) region, a first edit, a first nick-to-edit region, and a first primer binding site (PBS) region; and
   wherein the second CF editing cassette comprises a nucleic acid molecule encoding from 5' to 3':
      (iii) a second CFgRNA comprising a 5' to 3' spacer region and a scaffold region; and
      (iv) a second repair template comprising second PEH region, a second edit, a second nick-to-edit region, and a second PBS region;
   (d) providing conditions to allow the nucleic acid-guided nuclease/reverse transcriptase fusion enzyme and the first CF editing cassette to bind to the first strand of the target locus, and the nucleic acid-guided nuclease/reverse transcriptase fusion enzyme and the second CF editing cassette to bind to the second strand of the target locus; and
   (e) allowing the nucleic acid-guided nuclease/reverse transcriptase fusion enzyme and the first CF editing cassette to generate an insertion, deletion, or substitution of 1 or more nucleotides in the first strand of the target locus based on the first repair template and allowing the nucleic acid-guided nuclease/reversed transcriptase fusion enzyme and the second CF editing cassette to generate an insertion, deletion, or substitution of 1 or more nucleotides in the second strand of the target locus based on the second repair template.

2. The method of claim 1, wherein the CF editing cassettes further comprise an edit to immunize the target locus to prevent re-nicking.

3. The method of claim 1, wherein the first nick-to-edit region or the second nick-to-edit region is from 2 to 250 nucleotides in length.

4. The method of claim 3, wherein the first nick-to-edit region or the second nick-to-edit region is from 5 to 150 nucleotides in length.

5. The method of claim 1, wherein the first nick-to-edit region or the second nick-to-edit region is from 0 to 150 nucleotides in length.

6. The method of claim 1, wherein the first region of complementarity and the second region of complementarity are from 4 to 120 nucleotides in length.

7. The method of claim 6, wherein the first region of complementarity and the second region of complementarity are from 5 to 80 nucleotides in length.

8. The method of claim 7, wherein the first region of complementarity and the second region of complementarity are from 6 to 60 nucleotides in length.

9. The method of claim 1, wherein the first PEH region or the second PEH region is from 2 to 50 nucleotides in length.

10. The method of claim 9, wherein the first PEH region or the second PEH region is from 4 to 40 nucleotides in length.

11. The method of claim 10, wherein the first PEH region or the second PEH region is from 5 to 25 nucleotides in length.

12. The method of claim 1, wherein the first edit or the second edit comprise a single substitution in the target locus.

13. The method of claim 1, wherein the first edit or the second edit comprise an insertion in the target locus.

14. The method of claim 1, wherein the first edit or the second edit comprise a deletion in the target locus.

15. The method of claim 1, wherein the first edit or the second edit are positioned within a coding region of the target locus.

16. The method of claim 1, wherein the first edit or the second edit are positioned within a noncoding region of the target locus.

17. The method of claim 1, wherein the nuclease portion of the nucleic acid-guided nickase/reverse transcriptase fusion enzyme is a MAD2007 nickase.

* * * * *

SEQUENCE LISTING

```
<160> NUMBER OF SEQ ID NOS: 19

<210> SEQ ID NO 1
<211> LENGTH: 5
<212> TYPE: PRT
<213> ORGANISM: Artificial Sequence
<220> FEATURE:
<223> OTHER INFORMATION: Synthetic construct

<400> SEQUENCE: 1

Gly Gly Gly Gly Ser
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic construct

<400> SEQUENCE: 2

Ala Glu Ala Ala Ala Lys Ala
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic construct

<400> SEQUENCE: 3

Leu Ala Gly Leu Ile Asp Ala Asp Gly
1               5
```

```
<210> SEQ ID NO 4
<211> LENGTH: 59
<212> TYPE: DNA
<213> ORGANISM: Artificial Sequence
<220> FEATURE:
<223> OTHER INFORMATION: Synthetic construct

<400> SEQUENCE: 4
tcgggatagc ggctgaagca ctgcacgccg gctgtcaggg tggtcaccaa agtgggcca      59

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
ggtgctgctt catgtggtcg                                                 20

<210> SEQ ID NO 6
<211> LENGTH: 76
<212> TYPE: DNA
<213> ORGANISM: Artificial Sequence
<220> FEATURE:
<223> OTHER INFORMATION: Synthetic construct

<400> SEQUENCE: 6
gttttagagc tagaaatagc aagttaaaat aaggctagtc cgttatcaac ttgaaaaagt     60
gggaccgagt cggtcc                                                     76

<210> SEQ ID NO 7
<211> LENGTH: 25
<212> TYPE: DNA
<213> ORGANISM: Artificial Sequence
<220> FEATURE:
<223> OTHER INFORMATION: Synthetic construct

<400> SEQUENCE: 7
cctggcccac tttggtgacc accct                                           25

<210> SEQ ID NO 8
<211> LENGTH: 42
<212> TYPE: DNA
<213> ORGANISM: Artificial Sequence
<220> FEATURE:
<223> OTHER INFORMATION: Synthetic construct

<400> SEQUENCE: 8
acggcgtgca gtgcttcagc cgctatcccg acgctatccc ga                        42

<210> SEQ ID NO 9
<211> LENGTH: 13
<212> TYPE: DNA
<213> ORGANISM: Artificial Sequence
<220> FEATURE:
<223> OTHER INFORMATION: Synthetic construct

<400> SEQUENCE: 9
ccacatgaag cag                                                        13

<210> SEQ ID NO 10
<211> LENGTH: 93
<212> TYPE: DNA
<213> ORGANISM: Artificial Sequence
<220> FEATURE:
```

```
<223> OTHER INFORMATION: Synthetic construct

<400> SEQUENCE: 10
atacggcaag ctgaccctga agttcatctg caccaccggc aaactgcccg tgccctggcc    60
cactttggtg accaccctga cagccggcgt gca                                 93

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
ggcgagggcg atgccaccta                                                20

<210> SEQ ID NO 12
<211> LENGTH: 76
<212> TYPE: DNA
<213> ORGANISM: Artificial Sequence
<220> FEATURE:
<223> OTHER INFORMATION: Synthetic construct

<400> SEQUENCE: 12
gttttagagc tagaaatagc aagttaaaat aaggctagtc cgttatcaac ttgaaaaagt    60
gggaccgagt cggtcc                                                    76

<210> SEQ ID NO 13
<211> LENGTH: 78
<212> TYPE: DNA
<213> ORGANISM: Artificial Sequence
<220> FEATURE:
<223> OTHER INFORMATION: Synthetic construct

<400> SEQUENCE: 13
agggtggtca ccaaagtggg ccagggcacg ggcagtttgc cggtggtgca gatgaacttc    60
agggtcagct tgccgtat                                                  78

<210> SEQ ID NO 14
<211> LENGTH: 13
<212> TYPE: DNA
<213> ORGANISM: Artificial Sequence
<220> FEATURE:
<223> OTHER INFORMATION: Synthetic construct

<400> SEQUENCE: 14
gtggcatcgc cct                                                       13

<210> SEQ ID NO 15
<211> LENGTH: 77
<212> TYPE: DNA
<213> ORGANISM: Artificial Sequence
<220> FEATURE:
<223> OTHER INFORMATION: Synthetic construct

<400> SEQUENCE: 15
tggcagactt gaagaagtcg tgctgcttca tgtggtcggg gtagcggctg aagcactgca    60
cgccggctgt cagggtg                                                   77

<210> SEQ ID NO 16
<211> LENGTH: 20
<212> TYPE: DNA
<213> ORGANISM: Artificial Sequence
```

```
<220> FEATURE:
<223> OTHER INFORMATION: Synthetic construct

<400> SEQUENCE: 16
gacgtagcct tcgggcatgg                                                    20

<210> SEQ ID NO 17
<211> LENGTH: 76
<212> TYPE: DNA
<213> ORGANISM: Artificial Sequence
<220> FEATURE:
<223> OTHER INFORMATION: Synthetic construct

<400> SEQUENCE: 17
gttttagagc tagaaatagc aagttaaaat aaggctagtc cgttatcaac ttgaaaaagt        60
gggaccgagt cggtcc                                                        76

<210> SEQ ID NO 18
<211> LENGTH: 66
<212> TYPE: DNA
<213> ORGANISM: Artificial Sequence
<220> FEATURE:
<223> OTHER INFORMATION: Synthetic construct

<400> SEQUENCE: 18
acggcgtgca gtgcttcagc cgctaccccg accacatgaa gcagcacgac ttcttcaagt        60
ctgcca                                                                   66

<210> SEQ ID NO 19
<211> LENGTH: 13
<212> TYPE: DNA
<213> ORGANISM: Artificial Sequence
<220> FEATURE:
<223> OTHER INFORMATION: Synthetic construct

<400> SEQUENCE: 19
tgcccgaagg cta                                                           13
```